United States Patent
Lally et al.

(10) Patent No.: US 9,522,943 B2
(45) Date of Patent: Dec. 20, 2016

(54) TREATING HUMAN IMMUNODEFICIENCY VIRUS INFECTIONS

(71) Applicant: Rhode Island Hospital, A Lifespan-Partner, Providence, RI (US)

(72) Inventors: Michelle Lally, Cumberland, RI (US); Bharat Ramratnam, Tiverton, RI (US); Ming Li, Cranston, RI (US)

(73) Assignee: Rhode Island Hospital, A Lifespan-Partner, Providence, RI (US)

( * ) Notice: Subject to any disclaimer, the term of this patent is extended or adjusted under 35 U.S.C. 154(b) by 0 days.

(21) Appl. No.: 14/378,715

(22) PCT Filed: Jan. 18, 2013

(86) PCT No.: PCT/US2013/022142
§ 371 (c)(1),
(2) Date: Aug. 14, 2014

(87) PCT Pub. No.: WO2013/130188
PCT Pub. Date: Sep. 6, 2013

(65) Prior Publication Data
US 2016/0002304 A1    Jan. 7, 2016

Related U.S. Application Data

(60) Provisional application No. 61/606,173, filed on Mar. 2, 2012.

(51) Int. Cl.
*A61K 38/17*  (2006.01)
*A61K 45/06*  (2006.01)
*C07K 14/47*  (2006.01)
*G01N 33/569* (2006.01)

(52) U.S. Cl.
CPC ........... *C07K 14/47* (2013.01); *A61K 38/1709* (2013.01); *A61K 45/06* (2013.01); *G01N 33/56988* (2013.01); *C07K 2319/85* (2013.01); *G01N 2333/4703* (2013.01)

(58) Field of Classification Search
CPC .... A61K 38/1709; A61K 45/06; C07K 14/47; C07K 2319/85; G01N 2333/4703; G01N 33/56988
USPC ............................ 514/3.8; 530/350; 436/501
See application file for complete search history.

(56) References Cited

U.S. PATENT DOCUMENTS

| | | |
|---|---|---|
| 2004/0253606 A1* | 12/2004 | Aziz ................. C07H 21/04 435/6.12 |
| 2005/0255114 A1 | 11/2005 | Labat et al. |
| 2007/0185017 A1 | 8/2007 | Aggarwal et al. |
| 2009/0215178 A1 | 8/2009 | Tang |
| 2009/0232802 A1 | 9/2009 | Fong et al. |
| 2010/0273859 A1 | 10/2010 | Elledge et al. |

FOREIGN PATENT DOCUMENTS

JP    2003-000270    7/2003

OTHER PUBLICATIONS

SEQ ID No. 694 from U.S. Appl. No. 10/723,869, same as US 2004/0253606, Dec. 2004.*
Brass, et al., "Identification of Host Proteins Required for HIV Infection Through a Functional Genomic Screen", *Science*, vol. 319, Feb. 15, 2008, pp. 921-926.
Erkmann, et al., "Nuclear Import of the Stem-Loop Binding Protein and Localization during the Cell Cycle", *Molecular Biology of the Cell*, vol. 16, pp. 2960-2971, Jun. 2005.
Gorgoni et al., "The stem-loop binding protein stimulates histone translation at an early step in the initiation pathway", RNA 2005, 11; pp. 1030-1042.
International Search Report for PCT/US/2013/022142, dated Jun. 17, 2013. 6 pages.
Li et al., "Proteomics of HIV-1 Control", Mar. 7, 2012, [Retrieved from the Internet May 17, 2013: http://www.retroconference.org/2012b/PDFs/296.pdf], 1 page.
Liu, et al., "MicroRNA-dependent localization of targeted mRNAs to mammalian P-bodies", *National Cell Biol.*, Apr. 24, 2007, 11 pages.
Ohba etla., "Follicular Dendritic Cells Activate HIV-1 Replication in Monocytes/Macrophages through a Juxtacrine Mechanism Medicated by P-Selectin Glycoprotein Ligand 1", *The Journal of Immunology*, 2009, 183, pp. 524-532.
Sanchez, et al. "The stem-loop binding protein is required for efficient translation of histone mRNA in vivo and in vitro", *Molecular and Cellular Biology*, vol. 22, No. 20, Oct. 2002, pp. 7093-7104.
Schweitzer, "Identification of Novel Cellular Components Associated with HIV-1 Early Nucleoprotein Complexes", [Retrieved from the Internet May 18, 2013: http://dspace.creighton.edu:8080/xmlui/bitstream/handle/10504/28620/Schweitzer_Cameron_Dissertation.pdf?sequence=1]; p. 140, para 4.3.6; p. 132; table 4.6.
Sullivan, et al., "Knockdown of SLBP results in nuclear retention of histone mRNA", *RNA* (2009), 15; pp. 459-472.
UniProtKB/Swiss-Prot: Q14493. "RecName: Full=Histone RNA hairpin-binding protein; AltName: Full=Histone stem-loop-binding protein", Feb. 22, 2012, [Retrieved from the Internet May 17, 2013: http://www.ncbi.nlm.nlm.nih.gov/protein/9789785?sat=15 &satkey=6374100], 8 pages.
Zhao, et al., "The human histone gene expression regulator HBP/SLBP is required for histone and DNA synthesis, cell cycle progression and cell proliferation in mitotic cells", Journal of Cell Science 117 (25), pp. 6043-6051 (2004).
International Search Report for PCT/US/2013/022142, dated Jun. 17, 2013. 14 pages.

* cited by examiner

*Primary Examiner* — Julie Ha
(74) *Attorney, Agent, or Firm* — Fish & Richardson P.C.

(57) ABSTRACT

Methods and compositions for determining a prognosis for a subject infected with HIV, reducing a risk of an HIV infection, and treating or reducing a risk of developing AIDS are described.

6 Claims, 27 Drawing Sheets

| Group | ID | CD4 Count | Viral Load | Category |
|---|---|---|---|---|
| Set1 | HAPP-01 | 86 | 139,620 | progressor |
| | HAPP-02 | 406 | 651 | controller |
| | HAPP-03 | 509 | 26,627 | progressor |
| | HAPP-04 | 508 | 15,249 | progressor |
| | HAPP-05 | 583 | 354 | controller |
| | HAPP-06 | 560 | 147 | controller |
| | HAPP-07 | 503 | 11,094 | progressor |
| | HAPP-08 | 1,397 | <50 | controller |
| | HAPP-09 | 816 | 25,210 | progressor |
| | HAPP-10 | 1,140 | 1,167 | controller |
| Set2 | HAPP-14 | 523 | 21,700 | progressor |
| | HAPP-15 | 304 | 61 | controller |
| | HAPP-18 | 1,277 | 10,365 | progressor |
| | HAPP-20 | 302 | 55,800 | progressor |
| | HAPP-21 | 447 | 158,780 | progressor |
| | HAPP-22 | 255 | 12,828 | progressor |
| | HAPP-23 | 906 | 792 | controller |
| | HAPP-24 | 645 | 90 | controller |
| | HAPP-25 | 950 | <50 | controller |
| | HAPP-26 | 979 | 201 | controller |

| ID | CD4 Count | Viral Load | Category | Avg. CD4 | Avg. Viral Load |
|---|---|---|---|---|---|
| HAPP-08 | 1,397 | <50 | controller | | |
| HAPP-25 | 950 | <50 | controller | | |
| HAPP-15 | 304 | 61 | controller | | |
| HAPP-24 | 645 | 90 | controller | | |
| HAPP-06 | 560 | 147 | controller | | |
| HAPP-26 | 979 | 201 | controller | | |
| HAPP-05 | 583 | 354 | controller | | |
| HAPP-02 | 406 | 651 | controller | | |
| HAPP-23 | 906 | 792 | controller | | |
| HAPP-10 | 1,140 | 1,167 | controller | 787 | 356 |
| HAPP-18 | 1,277 | 10,365 | progressor | | |
| HAPP-07 | 503 | 11,094 | progressor | | |
| HAPP-22 | 255 | 12,828 | progressor | | |
| HAPP-04 | 508 | 15,249 | progressor | | |
| HAPP-14 | 523 | 21,700 | progressor | | |
| HAPP-09 | 816 | 25,210 | progressor | | |
| HAPP-03 | 509 | 26,627 | progressor | | |
| HAPP-20 | 302 | 55,800 | progressor | | |
| HAPP-01 | 86 | 139,620 | progressor | | |
| HAPP-21 | 447 | 158,780 | progressor | 523 | 47,725 |

FIG. 1

| Functions | Protein Names | Uniprot Name | Silac Ratio 1st set | Silac Ratio 2nd set |
|---|---|---|---|---|
| Vpr (host virus interaction) | Importin subunit alpha-2 | IPA2_HUMAN | 2.75 | 1.68 |
| Nucleotide biosynthesis | Thymidylate synthase | TYSY_HUMAN | 2.34 | 1.54 |
| PHA stimulation | 4F2 cell-surface antigen heavy chain | 4F2_HUMAN | 1.84 | 1.51 |
| Tumorgenesis | Thiosulfate sulfurtransferase/rhodanese-like domain-containing protein 1 | TSTD1_HUMAN | 0.49 | 0.42 |
| Tca cycle | NAD(P) transhydrogenase, mitochondrial | NNTM_HUMAN | 0.39 | 0.48 |
| Homooligomerization | Erythrocyte band 7 integral membrane protein | STOM_HUMAN | 0.39 | 0.49 |
| Electron transport | NADH dehydrogenase [ubiquinone] 1 beta subcomplex subunit 8, mitochondrial | NDUB8_HUMAN | 0.36 | 0.45 |
|  | Histone H2A.Z | H2AZ_HUMAN | 0.31 | 0.37 |
| Antiviral | Protein S100-A4 | S10A4_HUMAN | 0.30 | 0.41 |
|  | SAM domain and HD domain-containing protein 1 | SAMH1_HUMAN | 0.30 | 0.4 |
|  | Histone H1x | H1X_HUMAN | 0.25 | 0.39 |
| Carbohydrate metabolism | Phosphoglucomutase-2 | PGM2_HUMAN | 0.21 | 0.42 |
|  | Histone H1.2 | H12_HUMAN | 0.20 | 0.48 |
|  | Histone H2B | H2B2F_HUMAN | 0.17 | 0.31 |
|  | Histone H1.3 | H13_HUMAN | 0.16 | 0.47 |
|  | Histone H4 | H4_HUMAN | 0.12 | 0.23 |
| Inflammatory response | Protein S100-A9 | S10A9_HUMAN | 0.06 | 0.05 |
| Cell adhesion | Vinculin | VINC_HUMAN | 0.06 | 0.39 |
| Inflammatory response | Protein S100-A8 | S10A8_HUMAN | 0.05 | 0.03 |

FIG. 5

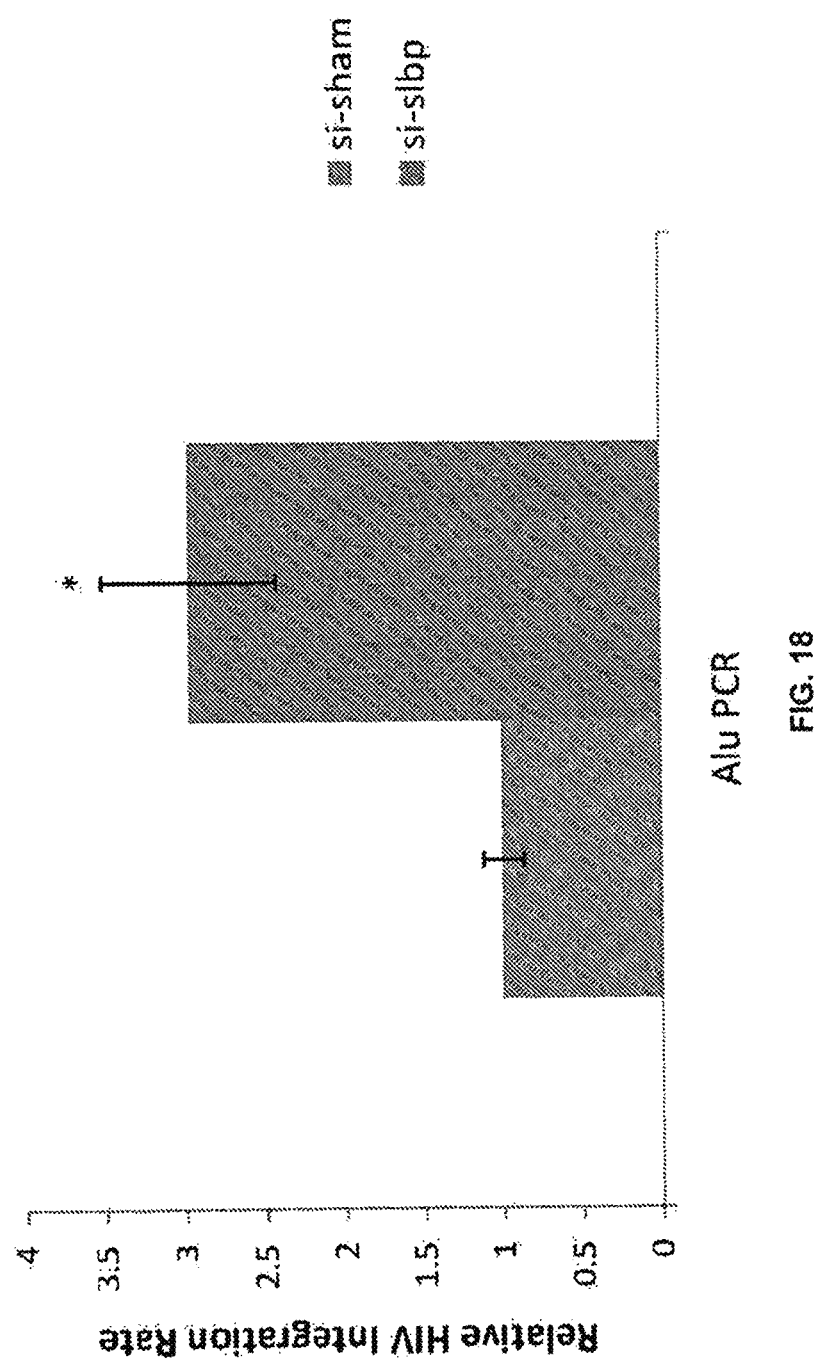

TREATING HUMAN IMMUNODEFICIENCY VIRUS INFECTIONS

CROSS REFERENCE TO RELATED APPLICATIONS

This application is the U.S. National Phase Application under 35 U.S.C. §371 of International Patent Application No. PCT/US2013/022142, filed Jan. 18, 2013, which claims the benefit of U.S. Application No. 61/606,173, filed on Mar. 2, 2012, the entire contents of which are hereby incorporated by reference in its entirety.

FEDERALLY SPONSORED RESEARCH OR DEVELOPMENT

This invention was made with U.S. Government support under Grant Number 3P30AI042853-13S1 awarded by the National Institutes of Health. The Government has certain rights in the invention.

TECHNICAL FIELD

The claimed methods and compositions relate to markers of human immunodeficiency virus infection and acquired immunodeficiency syndrome development.

BACKGROUND

Human immunodeficiency virus (HIV) is a lentivirus that causes acquired immunodeficiency syndrome (AIDS), a condition in humans in which progressive failure of the immune system allows life-threatening opportunistic infections and cancers to thrive. Infection with HIV occurs by the transfer of blood, semen, vaginal fluid, pre-ejaculate, or breast milk. Within these bodily fluids, HIV is present as both free virus particles and virus within infected immune cells. The four major routes of transmission are unsafe sex, contaminated needles, breast milk, and perinatal transmission. Screening of blood products for HIV has largely eliminated transmission through blood transfusions or infected blood products in the developed world.

HIV infection in humans is considered pandemic by the World Health Organization. HIV infects vital cells in the human immune system such as helper T cells (specifically CD4+ T cells), macrophages, and dendritic cells. HIV infection leads to low levels of CD4+ T cells through three main mechanisms: direct viral killing of infected cells; increased rates of apoptosis in infected cells; and killing of infected CD4+ T cells by CD8+ cytotoxic lymphocytes that recognize infected cells. When CD4+ T cell numbers decline below a critical level, cell-mediated immunity is lost, and the body becomes progressively more susceptible to opportunistic infections.

Most untreated people infected with HIV eventually develop AIDS. These individuals usually die from opportunistic infections or malignancies associated with the progressive failure of the immune system. HIV progresses to AIDS at a variable rate affected by viral, host, and environmental factors; most will progress to AIDS within 10 years of HIV infection; some will progress much sooner, and some will take much longer.

A small percentage of HIV-infected individuals retain high levels of CD4+ T-cells without anti-retroviral therapy. However, most have detectable viral load and will eventually progress to AIDS without treatment, albeit more slowly than others. These individuals are classified as HIV controllers or long-term non-progressors. Subjects who maintain CD4+ T cell counts and also have low or clinically undetectable viral load without anti-retroviral treatment are known as elite controllers.

Treatment with anti-retroviral drugs can reduce both the mortality and the morbidity of HIV infection. Although numerous medications are available to inhibit development of AIDS and slow progression of the disease, there is no cure for HIV/AIDS. These drugs have reduced AIDS deaths in many developed nations, but HIV continues to decimate populations in Africa, Haiti, and parts of Asia. Therefore, effective methods and compositions for determining a prognosis for a subject infected with HIV, reducing a risk of an HIV infection, and treating or reducing a risk of developing AIDS are desirable.

SUMMARY

The present invention is based, in part, on the discovery that stem loop binding protein (SLBP) and histones H1X, H1.2, H1.3, H2A.Z, H2B, and H4 are under-expressed in HIV-infected subjects that develop AIDS. The present specification provides methods and compositions to treat human immunodeficiency virus infection and acquired immunodeficiency syndrome.

Accordingly, in one aspect, the present specification provides polypeptides, e.g., recombinant polypeptides, comprising a SLBP. For example, in one embodiment, the polypeptide comprises an amino acid sequence that is at least 90%, e.g., at least 92%, 95%, 96%, 97%, 98%, 99%, or 100% identical to SEQ ID NO:2. The SLBP can be fused to a second amino acid sequence, e.g., a nuclear localization signal.

In another aspect, pharmaceutical compositions comprising a polypeptide comprising a SLBP, e.g., a recombinant SLBP, e.g., fused to a second amino acid sequence (e.g., an unrelated amino acid sequence) such as a nuclear localization signal, are provided with a pharmaceutically acceptable carrier.

In yet another aspect, nucleic acid molecules encoding a polypeptide comprising a SLBP are described. For example, the SLBP can include an amino acid sequence that is at least 90%, e.g., at least 92%, 95%, 96%, 97%, 98%, 99%, or 100% identical to SEQ ID NO:2. In one embodiment, the nucleic acid sequence encoding for SLBP comprises a nucleic acid sequence that is at least 90%, e.g., at least 92%, 95%, 96%, 97%, 98%, 99%, or 100% identical to SEQ ID NO:1. In some instances, a nucleic acid molecule described herein can encode a polypeptide comprising a SLBP fused to a second amino acid sequence (e.g., a non-SLBP sequence), e.g., a nuclear localization signal.

In still another aspect, vectors comprising a nucleic acid molecule encoding a polypeptide comprising a SLBP, e.g., fused to a second amino sequence (e.g., a non-SLBP sequence), e.g., a nuclear localization signal, are described. Pharmaceutical compositions comprising the vector are also provided. The vector can also be comprised within a cell, e.g., bacterial cell, insect cell, mammalian, e.g., human, cell.

In a further aspect, methods of producing SLBP are described. The method can include providing a cell comprising a nucleic acid molecule encoding a polypeptide comprising a SLBP, optionally fused to a second amino acid sequence (e.g., a non-SLBP sequence), e.g., a nuclear localization signal; and culturing the cell under conditions sufficient to produce SLBP, thereby producing SLBP. In one embodiment, the method includes purifying or isolating SLBP from the cell.

The methods described herein also feature determining a prognosis for a subject, e.g., a human, infected with HIV, e.g., HIV-1, the methods comprising providing a sample, e.g., serum, plasma, or blood, from a subject infected with HIV; assaying the sample to determine a level of SLBP in the sample to obtain a SLBP test value; and comparing the SLBP test value to a SLBP reference value; wherein the SLBP test value compared to the SLBP reference value indicates the prognosis for the subject. The methods can further include treating the subject with an SLBP (e.g., an SLBP fused to a second amino acid sequence), an art-known treatment, e.g., an anti-retroviral therapy (e.g., an entry inhibitor (e.g., enfuvirtide (FUZEON®)), a CCR5 receptor antagonist (e.g., maraviroc (SELZENTRY®)), a reverse-transcriptase inhibitor (e.g., zidovudine (RETROVIR®), a protease inhibitor (e.g., atazanavir (REYATAZ®), darunavir (PREZISTA®), fosamprenavir (LEXIVA®), and ritonavir (NORVIR®)), an integrase inhibitor (e.g., Raltegravir (ISENTRESS®)), a maturation inhibitor (e.g., Bevirimat, Vivecon)), or any combination thereof. In some instances, the level of SLBP is determined, e.g., by Western blot and/or enzyme linked immunosorbent assay using, e.g., an antibody or fragment thereof, e.g., that specifically binds to SLBP (i.e., an anti-SLBP antibody).

In one embodiment, the methods further comprise assaying the sample to determine a level of histone H1X, H1.2, H1.3, H2A.Z, H2B, or H4 to obtain a histone test value; and comparing the histone test value to its respective histone reference value; wherein the histone test value compared to its respective histone reference value indicates the prognosis for the subject. A test value that is less than or about the same as its respective reference value indicates that the subject is at a greater risk of developing AIDS. A test value that is greater than its respective reference value indicates that the subject is at a lower risk of developing AIDS. In some instances, the level of histone is determined, e.g., by Western blot and/or enzyme linked immunosorbent assay using, e.g., an antibody or fragment thereof, e.g., that specifically binds to one or more of the histones (i.e., an anti-histone antibody).

In yet another aspect, methods of reducing a risk of an HIV, e.g., HIV-1, infection in a subject are described. Also provided are methods of treating, or reducing a risk of developing, AIDS in a subject. The methods comprise administering intraperitoneally, intramusclularly, by infusion, vaginally, rectally, or orally to a subject a therapeutically effective amount of SLBP (e.g., SLBP polypeptide that is fused to a second amino acid sequence that is not an SLBP, e.g., a nuclear localization signal (NLS)), to thereby reduce the risk of an HIV infection in the subject or to treat, or reduce the risk of developing, AIDS in the subject.

In one embodiment, the methods further comprise selecting the subject, wherein selecting the subject comprises providing a sample. e.g., serum, plasma, or blood, from the subject; assaying the sample to determine a level of SLBP in the sample to obtain a test value; comparing the test value to a reference value; and selecting the subject (e.g., selecting the subject for treatment) if the test value is less than or in certain instances about the same as the reference value.

The methods can further include treating the subject with an anti-retroviral therapy, e.g., an entry inhibitor, a CCR5 receptor antagonist, a reverse-transcriptase inhibitor, a protease inhibitor, an integrase inhibitor, and a maturation inhibitor.

Also within the invention is the use of a SLBP described herein to manufacture a medicament for reducing a risk of an HIV infection or for treating, or reducing a risk of developing, AIDS.

In yet another aspect, methods of identifying a candidate compound for reducing a risk of an HIV infection or for treating, or reducing a risk of developing, AIDS in a subject are described. The methods comprise providing a sample comprising a living cell; contacting the sample with a test compound, e.g., polypeptides, ribonucleic acids, small molecules (e.g., small organic molecules), and deoxyribonucleic acids; determining a level of SLBP in the sample in the presence of the test compound; and selecting the test compound if the level of SLBP increases, relative to a level of SLBP in the absence of the test compound, wherein a test compound that increases the level of SLBP is a candidate compound for reducing the risk of an HIV infection, or for treating, or reducing the risk of developing, AIDS in a subject. Additionally, candidate compounds identified by these methods can be used to manufacture a medicament for reducing a risk of an HIV infection or for treating, or reducing a risk of developing, AIDS.

In one embodiment, the methods further comprise determining a level of histone H1X, H1.2, H1.3. H2A.Z, H2B, or H4 in the sample in the presence of the test compound; and selecting the test compound if the level of a histone increases, relative to a level of the histone in the absence of the test compound, wherein a test compound that increases the level of the histone is a candidate compound for reducing the risk of an HIV infection, or for treating, or reducing the risk of developing, AIDS in a subject.

Unless otherwise defined, all technical terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1 is a set of two tables with a description of the 20 patients studied in the experiments, 10 of which were classified as controllers and 10 of which were classified as progressors based on their viral load.

FIG. 5 is a table of a list of 19 candidate proteins, three of which are differentially over-expressed and 16 that are differentially under-expressed in progressors.

FIG. 18 is a bar graph depicting that decreased SLBP led to an increased HIV-1 integration rate.

DETAILED DESCRIPTION

Figure 2:
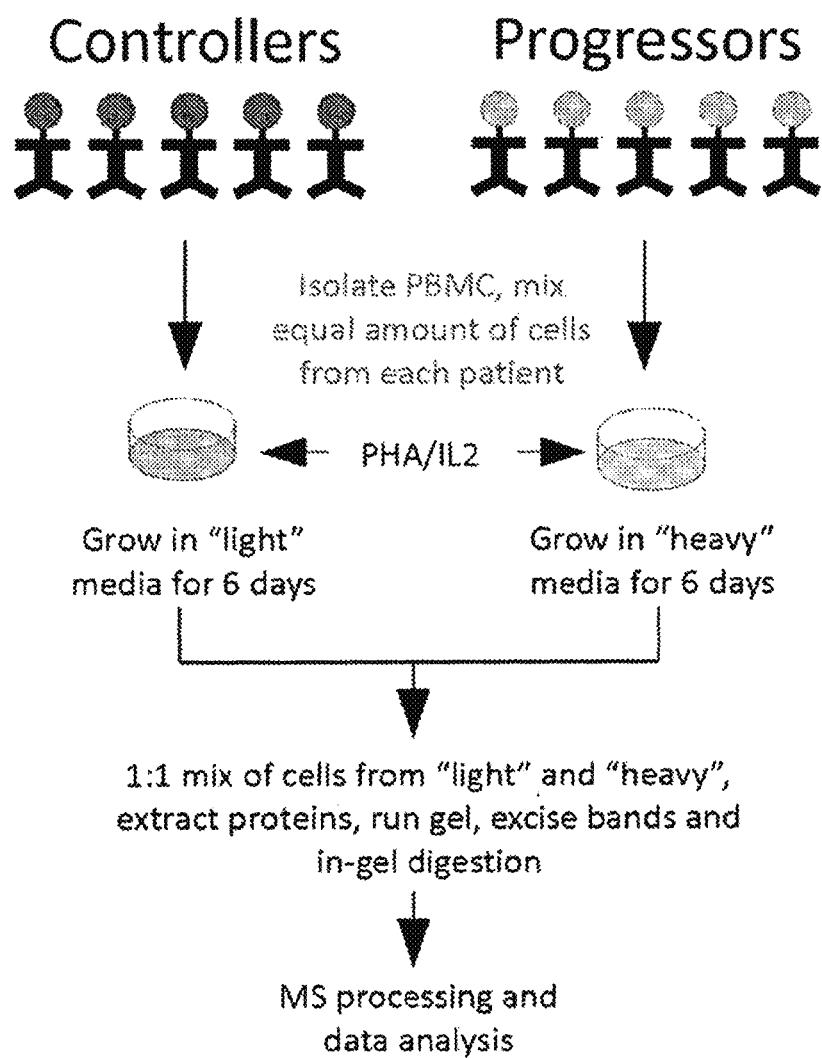
FIG. 2 is a schematic diagram of the experimental setup.

Most patients infected with HIV progress to develop AIDS over time unless treated with effective anti-retroviral medication. A minority of HIV-infected persons progress to AIDS slowly, or not at all, and these non-progressors or elite controllers have low levels of circulating virus. Immunologic factors have been hypothesized to explain the superior viral control in these individuals.

The invention described herein is based in part on identification of reduced levels of all classes of histone proteins in individuals with plasma HIV viral loads (PVL)>10,000 RNA copies/mL. This reduction was found to be related to decreased levels of SLBP, a stabilizer of histone mRNA. These results suggest that lymphocytic cells with decreased SLBP had more open chromatin structures, which in turn were associated with an enhanced ability of HIV, e.g., HIV-1, to integrate into the host genome and higher levels of viral transcriptional activity. These findings demonstrate that upon cellular entry, inter-individual differences in chromatin structure impact cellular viral burden.

A series of histone-related proteins (e.g., SLBP, H1X, H1.2, H1.3, H2A.Z, H2B, and H4) have been identified that are associated with risk of an HIV, e.g., HIV-1, infection and susceptibility to AIDS. The level or relative amount of one or more of these histone-related proteins, e.g., two, three, four, five, six, or seven proteins, can be used to determine a prognosis for a subject infected with HIV. e.g., HIV-1, reduce a risk of an HIV, e.g., HIV-1, infection, and treat or reduce a risk of developing AIDS in a subject. The seven biomarkers are described in Table 1. Further information on the biomarkers is also provided below.

TABLE 1

Biomarkers of HIV and AIDS

| Biomarker | Nucleic Acid | Protein | (GeneID) | Antibody Source |
|---|---|---|---|---|
| Stem Loop Binding Protein (SLBP) | NM_006527.2 | NP_006518.1 | 7884 | Sigma (HPA019254) |
| Histone H1X | NM_006026.3 | NP_006017.1 | 8971 | Sigma (SAB4501366) |
| Histone H1.2 | NM_005319.3 | NP_005310.1 | 3006 | Sigma (SAB4501366) |
| Histone H1.3 | NM_005320.2 | NP_005311.1 | 3007 | Sigma (SAB4501366) |
| Histone H2A.Z | NM_002106.3 | NP_002097.1 | 3015 | Abcam (ab18255) |
| Histone H2B | NM_001024599.3 | NP_001019770.1 | 440689 | Abcam (ab1790) |
| Histone H4 | NM_001034077.4 | NP_001029249.1 | 554313 | Abcam (ab10158) |

SLBP

SLBP is a RNA-binding protein involved in histone pre-mRNA processing. Histone mRNAs do not contain introns or polyadenylation signals, and are processed by endonucleolytic cleavage. SLBP binds the stem-loop structure of replication-dependent histone pre-mRNAs and contributes to efficient 3'-end processing by stabilizing the complex between histone pre-mRNA and U7 small nuclear ribonucleoprotein via the histone downstream element. SLBP plays an important role in targeting mature histone mRNA from the nucleus to the cytoplasm and to the translation machinery. Further, SLBP stabilizes mature histone mRNA and is involved in cell-cycle regulation of histone gene expression.

The human SLBP sequence is known in the art; exemplary reference sequences can be found in the GenBank database at accession number NM_006527.2 (nucleic acid) and NP_006518.1 (amino acid). See also GeneID: 7884. SLBP is encoded by a 813 base pair sequence found on chromosome 4 of the human genome (SEQ ID NO:1). The protein, as shown below, is 270 residues long (SEQ ID NO:2).

SLBP Nucleic Acid Sequence (SEQ ID NO: 1)

atggcctgcc gcccgcgaag cccgccgagg catcagagcc gctgcgacgg tgacgccagc ccgccgtccc ccgcgggatg gagcctggga cggaagcgca gagccgacgg caggcgctgg aggcccgaag acgccgagga ggcagagcac cgcggcgccg agcgcagacc cgagagcttt accactcctg aaggccctaa accccgttcc agatgctctg actgggcaag tgcagttgaa gaagatgaaa tgaggaccag agttaacaaa gaaatggcaa gatataaaag caaactcctc atcaatgact ttggaagaga gagaaaatca tcatcaggaa gttctgattc aaaggagtct atgtctactg tgccggctga cttttgagaca gatgaaagtg tcctaatgag gagacagaag cagatcaact atgggaagaa cacaattggc tacgatcgtt atattaaaga agtcccaaga caccttcgac aacctggcat tcatcccaag accctaata aatttaagaa gtataqtcqa cgttcatggg accaccaaat caaactctgg aaggtggctc tgcatttttg ggatcctcca gcggaagaag gatgtgattt gcaagaaata caccctgtag accttgaatc tgcagaaagc agctccgagc cccagaccag ctctcaggat gactttgatg tgtactatgg cacacccacc aaggtgagac acatggacag tcaagtggag gatgagtttg atttggaagc ttgtttaact gaaccettga gagacttctc agccatgagc taa SLBP Protein Sequence (SEQ ID NO: 2)

1 macrprsppr hqsrcdgdas ppsparwslq rkrradgrrw rpedaceach rgaerrpesf 61 ttpegpkprs rcsdwasave edemrtrvnk emarykrkll indfgrerks ssgssdskes 121 mstvpadfet deuvlmrrqk qinygkntia ydryikevpr hlrqpgihpk tpnkfkkysr 181 rSwdqdiklw kvalhfwdpp aeegedldei hpvdlesaes ssepqtssqd dfdvysgtpt 241 kvrhmdsqve defdleaclt eplrdfsams This 31,286 Da protein localizes predominantly in the nucleus at the G1/G2 phases and the beginning of S phase. Through the S phase, it partially redistributes to the cytoplasm and shuttles back to the nucleus by the Importin alpha/Importin beta receptor. SLBP antibodies are commercially available, e.g., from Abcam plc. (e.g., ab56027 and ab56329); Santa Cruz Biotechnology (e.g., sc-26522); Novus Biologicals (e.g., Cat. No. NBP1-83290); and Sigma-Aldrich Co. (e.g., Cat. No. HPA019254).

Histone H1X

Histone H1X is a 213 amino acid protein that is localized to the nucleus. Histone H1X belongs to the Histone H1/H5 family and is an H1 Histone, which are important in the process of condensing nucleosome chains into structures inside chromosomes. H1 histones also regulate DNA repair and replication as well as gene expression.

The human histone H1X sequence can be found in the GenBank database at accession number NM 006026.3 (nucleic acid) and NP 006017.1 (amino acid). See also GeneID: 8971. Histone H1X is encoded by a 642 base pair sequence found on chromosome 3 of the human genome (SEQ ID NO:3). The protein, as shown below, is 213 residues long (SEQ ID NO:4).

Histone H1X Nucleic Acid Sequence (SEQ ID NO: 3)
ATGTCCGTGGAGCTCGAGGAGGCCCTGCCAGTGACGACCGCCGAGGG

AATGGCCAAGAAGGTGACCAAGGCTGCCGCCTCGGCGGCGTTCTCCC

CATCTAAGAAGACGAAGAATAGCAAGAAGAAGAACCACCCGGGCAAG

TACAGCCAGCTGGTGGTGGAGACCATCCGTAGGCTGGGCGAGCGCAA

CGGCTCGTCGCTGGCCAAGATCTACACCGAGGCCAAGAACGTTCCGT

GGTTCCACCAGCAGAATGGGCGCACCTACCTCAAGTACTCGATCAAG

GCGCTGGTGCAGAACGACACGCTTCTGCAGGTGAAGGGCACCGGCGC

CAACGGTTCCTTCAAGCTCAACCGCAAGAAGCTGGAGGGCGGCGGGG

AGCGGCGCGGAGCCCCGGCGGCCGCCACCGCCCCCGGCCCCACCGCG

CACAAAGCGAAGAAGGCAGCCCCGGGCGCGGCCGGCTCCCGGCGCGC

GGACAAGAAGCCCGCCAGGGGCCAGAAGCCGGAGCAGCGCTCCACAA

GAAGGGCGCTGGCGCCAAGAAGGACGAAAGGCGGCAAGGCCAAGAAG

ACGGCGGCCGCCGGGGGCAAGAAGGTGAAGAAGGCGGCCAAGCCCAG

CGTCCCCAAAGTGCCCAAGGGCCGCAAGTGA

Histone H1x Protein Sequence (SEQ ID NO: 4)
MSVELEEALPVTTAEGMAKKVTKAGGSAALSPSKKRKNSKKKNQPGK

YSOLVVETIRRLGERNGSSLAKIYTEAKKVPWFDQQNGRTYLKYSIK

ALVQNDTLLQVKGTGANGSFKLNRKKLEGGGERRGAPAAATAPAPTA

HKAKKAAPGAAGSRRADKKPARGQKPEQRSHKKGAGAKKDKGGKAKK

TAAAGGKKVKKAAKPSVPKVPKGRK

During interphase, Histone H1X accumulates in nucleoli in the G1 phase and is evenly distributed throughout the nucleus during the S and G2 phases of the cell cycle. Tumors possess large quantities of Histone H1X. Histone H1X antibodies are commercially available, e.g., from Sigma-Aldrich Co. (Cat. No. SAB4501366).

Histone H1.2

Histone H1.2 is a subunit of Histone H1 that is necessary for the condensation of nucleosome chains into higher order structures. The human histone H1.2 sequence can be found in the GenBank database at accession number NM_005319.3 (nucleic acid) and NP_005310.1 (amino acid). See also GeneID: 3006. Histone H1.2 is encoded by a 642 base pair sequence found on chromosome 3 of the human genome (SEQ ID NO:5). The protein, as shown below, is 213 residues long (SEQ ID NO:6).

```
Histone H1.2 Nucleic Acid Sequence
                                        (SEQ ID NO: 5)
ATGTCCGAGACTGCTCCTGCCGCTCCCGCTGCCGCGCCTCCTGCGGA

GAAGGCCCCTGTAAAGAAGAAGGCGGCCAAAAAGGCTGGGGGTACGC

CTCGTAAGGCGTCTGGTCCCCCGGTGTCAGAGCTCATCACCAAGGCT

GTGGCCGCCTCTAAAGAGCGTAGCGGAGTTTCTCTGGCTGCTCTGAA

AAAAAGCGTTGGCGCCGCCGGCTATGATGTGGAGAAAAACAACAGCC

GTATCAAACTTGGTCTCAAGAGCCTGGTGAGCAAGGGCACTCTGGTG

CAAACGAAAGGCACCGGTGCTTCTGGCTCCTTTAAACTCAACAAGAA

GGCAGCCTCCGGGGAAGCCAAGCCCAAGGTTAAAAAGGCGGGCGGAA

CCAAACCTAAGAAGCCAGTTGGGGCAGCCAAGAAGCCCAAGAAGGCG

GCTGGCGGCGCAACTCCGAAGAAGAGCGCTAAGAAAACACCGAAGAA

AGCGAAGAAGCCGGCCGCGGCCACTGTAACCAAGAAAGTGGCTAAGA

GCCCAAAGAAGGCCAAGGTTGCGAAGCCCAAGAAAGCTGCCAAAAGT

GCTGCTAAGGCTGTGAAGCCCAAGGCCGCTAAGCCCAAGGTTGTCAA

GCCTAAGAAGGCGGCGCCCAAGAAGAAATAG
```

Histone H1.2 antibodies are commercially available, e.g., from Sigma-Aldrich Co. (Cat. No. SAB4501366).

Histone H1.3

Histone H1.3 is a subunit of Histone H1 that are necessary for the condensation of nucleosome chains into higher order structures. The human histone H1.3 sequence can be found in the GenBank database at accession number NM_005320.2 (nucleic acid) and NP_005311.1 (amino acid). See also GeneID: 3007. Histone H1.3 is encoded by a 666 base pair sequence found on chromosome 6 of the human genome (SEQ ID NO:7). The protein, as shown below, is 221 residues long (SEQ ID NO:8).

```
Histone H1.3 Nucleic Acid Sequence
                                        (SEQ ID NO: 7)
ATGTCGCAGACTGCTCCACTTGCTCCTACCATTCCTGCACCCGCAGA

AAAAACACCTGTGAAGAAAAAGGCGAAGAAGGCAGGCGCAACTGCTG

GGAAACGCAAAGCATCCGGACCCCCAGTATCTGAGCTTATCACCAAG

GCAGTGGCAGCTTCTAAGGAGCGCAGCGGCGTTTCTCTGGCCGCGCT

TAAGAAAGCGCTTGCGGCTGCTGGCTACGATGTAGAAAAAAACAACA

GCCGTATCAAGCTTGGCCTCAAGAGCTTGGTGAGCAAAGGTACTCTG

GTGCAGACCAAAGGTACCGGTGCTTCTGGCTCCTTCAAACTCAACAA
```

```
GAAAGCGGCTTCCGGGGAAGGCAAACCCAAGGCCAAAAAGGCTGGCG

CAGCCAAGCCTAGGAAGCCTGCTGGGGCAGCCAAGAAGCCCAAGAAG

GTGGCTGGCGCCGCTACCCCGAAGAAAAGCATCAAAAAGACTCCTAA

GAAGGTAAAGAAGCCAGCAACCGCTGCTGGGACCAAGAAAGTGGCCA

AGAGTGCGAAAAAGGTGAAAACACCTCAGCCAAAAAAAGCTGCCAAG

AGTCCAGCTAAGGCCAAAGCCCCTAAGCCCAAGGCGGCCAAGCCTAA

GTCGGGGAAGCCGAAGGTTACAAGGCAAAGAAGGCAGCTCCGAAGAA

AAAAGTGA
```

Histone H1.3 Protein Sequence
                                        (SEQ ID NO: 8)
MSETAPLAPTIPAPAEKTPVKKKAKKAGATAGKRKASGPPVSELITK

AVAASKERSGVSLAALKKALAAAGYDVEKNNSRIKLGLKSLVSKGTL

VQTKGTGASGSFKLNKKAASGEGKPKAKKAGAAKPRKPAGAAKKPKK

VAGAATPKKSIKKTPKKVKKPATAAGTKKVAKSAKKVKTPQPKKAAK

SPAKAKAPKPKAAKPKSGKPKVTKAKKAAPKKK

Histone H1.3 antibodies are commercially available, e.g., from Sigma-Aldrich Co. (Cat. No. SAB4501366).

Histone H2A.Z

Histone H2A.Z is a variant of histone H2A, one of the 5 main histone proteins involved in the structure of chromatin in eukaryotic cells. It plays roles in transcription regulation, DNA repair, DNA replication and chromosomal stability. The human histone H2A.Z sequence can be found in the GenBank database at accession number NM_002106.3 (nucleic acid) and NP_002097.1 (amino acid). See also GeneID: 3015. Histone H2A.Z is encoded by a 387 base pair sequence found on chromosome 4 of the human genome (SEQ ID NO:9). The protein, as shown below, is 128 residues long (SEQ ID NO:10).

```
Histone H2A.Z Nucleic Acid Sequence
                                        (SEQ ID NO: 9)
ATGGCTGGCGGTAAGGCTGGAAAGGACTCCGGAAAGGCCAAGACAAA

GGCGGTTTCCCGCTCGCAGAGAGCCGGCTTGCAGTTCCCAGTGGGCC

GTATTCATCGACACCTAAAATCTAGGACGACCAGTCATGGACGTGTG

GGCGCGACTGCCGCTGTGTACAGCGCAGCCATCCTCGAGTACCTCAC

CGCAGAGGTACTTGAACTGGCAGGAAATGCATCAAAAGACTTAAAGG

TAAAGCGTATTACCCCTCGTCACTTGCAACTTGCTATTCGTGGAGAT

GAAGAATTGGATTCTCTCATCAAGGCTACAATTGCTGGTGGTGGTGT

CATTCCACACATCCACAAATCTCTGATTGGGAAGAAAGGACAACAGA

AGACTGTCTAA
```

Histone H2A.Z Protein Sequence
                                        (SEQ ID NO: 10)
MAGGKAGKDSGKAKTKAVSRSQRAGLQFPVGRIHRHLKSRTTSHGRV

GATAAVYSAAILEYLTAEVLELAGNASKDLKVKRITPRHLQLAIRGD

EELDSLIKATIAGGGVIPHIHKSLIGKKGQQKTV

Histone H2A.Z antibodies are commercially available, e.g., from Abcam (Cat. No. ab18255).

Histone H2B

Histone H2B is one of the five main histone proteins involved in the structure of chromatin in eukaryotic cells.

H2B is involved with the structure of the nucleosomes. The human histone H2B sequence can be found in the GenBank database at accession number NM_001024599.3 (nucleic acid) and NP_001019770.1 (amino acid). See also GeneID: 440689. Histone H2B is encoded by a 381 base pair sequence found on chromosome 1 of the human genome (SEQ ID NO:11). The protein, as shown below, is 126 residues long (SEQ ID NO:12).

Histone H2B Nucleic Acid Sequence
(SEQ ID NO: 11)
ATGCCGGATCCAGCGAAATCCGCTCCTCCTCCCAAGAAGGGCTCCAA

AAAGGCTGTTACCAAAGTGCAGAAGAAGGACGGCAAGAAGCGCAAGC

GCAGCCGCAAGGAGAGCTACTCCGTTTACGTGTACAAGGTGCTGAAG

CAGGTCCACCCCGACACCGGCATCTCGTCCAAGGCCATGGGCATCAT

GAACTCCTTCGTCAACGACATCTTCGAGCGCATCGCGCGAGAGGCGT

CCCGCCTGGCGCACTACAACAAGCGCTCCACCATCACATCCCGCGAG

ATCCAGACGGCCGTGCGCCTGCTGCTGCCCGGCGAGCTGGCCAAGCA

CGCCGTGTCCCAGGGCACCAAGGCGGTCACCAAGTACACCAGCTCGA

AGTAA

Histone H2B Protein Sequence
(SEQ ID NO: 12)
MPDPAKSAPAPKKGSKKAVTKVQKKDGKNRKRSRKESYSVYVYKVLK

QVHPDTGISSKAMGIMNSEVNDIFERIAGEASRLAHYNKRSTITSRE

IQTAVLLLPGELAKHAVSEGTKAVTKYTSSK

Histone H2B antibodies are commercially available, e.g., from Abcam (Cat. No. ab1790).

Histone H4

Histone H4 is a core component of nucleosome. Featuring a main globular domain and a long N terminal tail, H4 is subject to covalent modification, including acetylation and methylation, which may alter expression of genes located on DNA associated with its parent histone octamer. The human histone H4 sequence can be found in the GenBank database at accession number NM_001034077.4 (nucleic acid) and NP_001029249.1 (amino acid). See also GeneID: 554313. Histone H4 is encoded by a 312 base pair sequence found on chromosome 1 of the human genome (SEQ ID NO:13). The protein, as shown below, is 103 residues long (SEQ ID NO:14).

Histone H4 Nucleic Acid Sequence
(SEQ ID NO: 13)
ATGTCCGGCAGAGGAAAGGGCGGAAAAGGCTTAGGCAAAGGGGCGC

TAAGCGCCACCGCAAGGTCTTGAGAGACAACATTCAGGGCATCACCA

AGCCTGCCATTCGGCGTCTAGCTCGGCGTGGCGGCGTTAAGCGGATC

TCTGGCCTCATTTACGAGGAGACCCGCGGTGTGCTGAAGGTGTTCCT

GGAGAATGTGATTCGGGACGCAGTCACCTACACCGAGCACGCCAAGC

GCAAGACCGTCACAGCCATGGATGTGGTGTACGCGCTCAAGCGCCAG

GGGCGCACCCTGTACGGCTTCGGAGGCTAG

Histone H4 Protein Sequence
(SEQ ID NO: 14)
MSGRGKGGKGLGKGGAKRHRKVLRDNIQGITKPAIRRLARRGGVKRI

SGLIYEETRGVLKVFLENVIRDAVTYTEHAKRKTVTAMDVVYALKRQ

GRTLYGFGG

Histone H4 antibodies are commercially available, e.g., from abcam Co. (Cat. No. ab10158).

Nucleic Acids, Proteins, Vectors, and Host Cells

In one aspect, the invention includes nucleic acids encoding SLBP fusion polypeptides, fragments, and variants thereof. A nucleic acid sequence encoding an exemplary SLBP polypeptide is provided in SEQ ID NO:1. The amino acid sequence encoded by SEQ ID NO:1 is provided in SEQ ID NO:2. In one aspect, the SLBP polypeptide is fused to a nuclear localization signal (NLS).

SLBP nucleic acids described herein include both RNA and DNA, including genomic DNA and synthetic (e.g., chemically synthesized) DNA. Nucleic acids can be double-stranded or single-stranded. Where single-stranded, the nucleic acid can be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The term "isolated nucleic acid" means a nucleic acid, e.g., DNA or RNA, that is not immediately contiguous with both of the coding sequences with which it is immediately contiguous (one on the 5' end and one on the 3' end) in the naturally occurring genome of the organism from which it is derived. Thus, in one embodiment, an isolated SLBP nucleic acid includes some or all of the 5' non-coding (e.g., promoter) sequences that are immediately contiguous to the SLBP nucleic acid coding sequence. The term includes, for example, recombinant DNA that is incorporated into a vector, into an autonomously replicating plasmid or virus, or into the genomic DNA of a prokaryote or eukaryote, or which exists as a separate molecule (e.g., a genomic DNA fragment produced by PCR or restriction endonuclease treatment) independent of other sequences. It also includes a recombinant DNA that is part of a hybrid gene encoding an additional polypeptide sequence.

The invention includes vectors, preferably expression vectors, containing a nucleic acid that encodes the fusion proteins described herein. As used herein, the term "vector" refers to a nucleic acid molecule capable of transporting another nucleic acid to which it has been linked and can include, e.g., a plasmid, cosmid, or viral vector. The vector can autonomously replicate or it can integrate into a host cell's DNA. Viral vectors include, e.g., replication-defective retroviruses, adenoviruses, and adeno-associated viruses.

A vector can include a NLS-SLBP nucleic acid in a form suitable for expression of the nucleic acid in a host cell. Preferably a recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce NLS-SLBP polypeptides encoded by nucleic acids as described herein.

The recombinant expression vectors of the invention can be designed for expression of NLS-SLBP polypeptides in prokaryotic or eukaryotic cells. For example, polypeptides of the invention can be expressed in E. coli, insect cells (e.g., using baculovirus expression vectors), yeast cells, or mammalian cells (e.g., CHO or COS cells). Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, Gene 67:31-40, 1988), pMAL (New England Biolabs, Beverly, Mass.) and pRIT5 (Pharmacia. Piscataway, N.J.) that fuse glutathione S-transferase (GST), maltose E binding protein, or protein A, respectively, to the target recombinant protein.

One can maximize recombinant protein expression in E. coli by expressing the protein in host bacteria with an impaired capacity to proteolytically cleave the recombinant protein (Gottesman (1990) Gene Expression Technology: Methods in Enzymology 185:119-128, Academic Press, San Diego, Calif.). Another strategy is to alter the nucleic acid sequence of the nucleic acid to be inserted into an expression vector so that the individual codons for each amino acid are those preferentially utilized in E. coli (Wada et al., Nucleic Acids Res 20:2111-2118, 1992). Such alteration of nucleic acid sequences of the invention can be carried out by standard DNA synthesis techniques.

Modified versions of peptides disclosed herein are referred to as "peptide derivatives," and they can also be used in the new methods. For example, peptide derivatives of a peptide can be used instead of that peptide in therapeutic methods described herein. Peptides disclosed herein can be modified according to the methods known in the art for producing peptidomimetics. See, e.g., Kazmierski, W. M., ed., *Peptidomimetics Protocols*, Human Press (Totowa N.J. 1998); Goodman et al., eds., *Houben-Weyl Methods of Organic Chemistry: Synthesis of Peptides and Peptidomimetics*, Thiele Verlag (New York 2003); and Mayo et al., J. Biol. Chem. 278:45746, 2003. In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N-terminus to the C-terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetics include replacing one or more amino acid residues in a peptide with a chemically distinct but recognized functional analog of the amino acid, i.e., an artificial amino acid analog. Artificial amino acid analogs include β-amino acids, β-substituted β-amino acids ("β$^3$-amino acids"), phosphorous analogs of amino acids, such as α-amino phosphonic acids and α-amino phosphinic acids, and amino acids having non-peptide linkages. Artificial amino acids can be used to create peptidomimetics, such as peptoid oligomers (e.g., peptoid amide or ester analogues), β-peptides, cyclic peptides, oligourea or oligocarbamate peptides; or heterocyclic ring molecules.

Nucleic acids disclosed herein also include both RNA and DNA, including genomic DNA and synthetic (e.g., chemically synthesized) DNA. Nucleic acids can be double-stranded or single-stranded. Nucleic acids can be synthesized using oligonucleotide analogs or derivatives (e.g., inosine or phosphorothioate nucleotides). Such oligonucleotides can be used, for example, to prepare nucleic acids with increased resistance to nucleases.

The term "purified" refers to a nucleic acid or polypeptide (e.g., an SLBP nucleic acid or SLBP polypeptide) that is substantially free of cellular or viral material with which it is naturally associated, or culture medium (when produced by recombinant DNA techniques), or chemical precursors or other chemicals (when chemically synthesized). Moreover, an isolated nucleic acid fragment is a nucleic acid fragment that is not naturally occurring as a fragment and would not be found in the natural state.

In some embodiments, the invention includes nucleic acid sequences that are substantially identical to an SLBP nucleic acid. A nucleic acid sequence that is "substantially identical" to an SLBP nucleic acid is at least 90% identical (e.g., at least about 95%, 96%, 97%, 98%, 99%, or identical) to the SLBP nucleic acid sequences represented by SEQ ID NO:1. For purposes of comparison of nucleic acids, the length of the reference nucleic acid sequence will be at least 50 nucleotides, but can be longer, e.g., at least 60 or more nucleotides.

To determine the percent identity of two amino acid or nucleic acid sequences, the sequences are aligned for optimal comparison purposes (i.e., gaps can be introduced as required in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences (i.e., % identity=# of identical positions/total # of overlapping positions×100). The two sequences may be of the same length.

The percent identity or homology between two sequences can be determined using a mathematical algorithm. A non-limiting example of a mathematical algorithm utilized for the comparison of two sequences is the algorithm of Karlin and Altschul, Proc. Natl. Acad. Sci. USA 87:2264-2268, 1990, modified as in Karlin and Altschul, Proc. Natl. Acad. Sci. USA 90:5873-5877, 1993. Such an algorithm is incorporated into the NBLAST and XBLAST programs of Altschul et al., J Mol Biol 215:403-410, 1990. BLAST nucleotide searches can be performed with the NBLAST program, score=100, wordlength=12 to obtain nucleotide sequences homologous to SLBP nucleic acid molecules of the invention. BLAST protein searches can be performed with the XBLAST program, score=50, wordlength=3 to obtain amino acid sequences homologous to SLBP protein molecules of the invention. To obtain gapped alignments for comparison purposes, Gapped BLAST can be utilized as described in Altschul et al., Nucleic Acids Res. 25:3389-3402, 1997. When utilizing BLAST and Gapped BLAST programs, the default parameters of the respective programs (e.g., XBLAST and NBLAST) can be used. See online at ncbi.nlm.nih.gov.

In other embodiments, the invention includes variants, homologs, and/or fragments of certain SLBP nucleic acids, e.g., variants, homologs, and/or fragments of the SLBP nucleic acid sequences represented by SEQ ID NO:1. The terms "variant" or "homolog" in relation to SLBP nucleic acids include any substitution, variation, modification, replacement, deletion, or addition of one (or more) nucleotides from or to the sequence of an SLBP nucleic acid. The resultant nucleotide sequence may encode an SLBP polypeptide that has at least 50% of a biological activity (e.g., binding to histone mRNAs) of the referenced SLBP polypeptides (e.g., SEQ ID NO:2). In particular, the term "homolog" covers homology with respect to structure and/or function as long as the resultant nucleotide sequence encodes or is capable of encoding an SLBP polypeptide that has at least 50% of the biological activity of SLBP encoded by a sequence shown herein as SEQ ID NO:1. With respect to sequence homology, there is at least 75% (e.g., 85%, 90%, 95%, 96%, 97%, 98%, 99%, or 100%) homology to the sequence shown as SEQ ID NO:1. The term "homology" as used herein can be equated with the term "identity."

"Substantial homology" or "substantially homologous," where homology indicates sequence identity, means at least 90% identical (e.g., at least about 92%, 95%, 96%, 97%, 98%, or 99%) sequence identity, as judged by direct sequence alignment and comparison. "Substantial homology" when assessed by the BLAST algorithm equates to sequences which match with an EXPECT value of at least about 7, e.g., at least about 9, 10, or more. The default threshold for EXPECT in BLAST searching is usually 10.

Also included within the scope of the present invention are certain alleles of certain SLBP genes. As used herein, an "allele" or "allelic sequence" is an alternative form of SLBP. Alleles can result from changes in the nucleotide sequence, and generally produce altered mRNAs or polypeptides whose structure or function may or may not be altered. Any given gene can have none, one, or more than one allelic form. Common changes that give rise to alleles are generally ascribed to deletions, additions, or substitutions of amino acids. Each of these types of changes can occur alone, or in combination with the others, one or more times in a given sequence.

The invention also includes nucleic acids that hybridize, e.g., under stringent hybridization conditions (as defined herein) to all or a portion of the nucleotide sequences represented by SEQ ID NO:1, or a complement thereof. The hybridizing portion of the hybridizing nucleic acids is typically at least 15 (e.g., 20, 30, or 50) nucleotides in length. The hybridizing portion of the hybridizing nucleic acid is at least about 75%, e.g., at least about 80%, 95%, 96%, 97%, 98%, 99%, or 100%, identical to the sequence of a portion or all of a nucleic acid encoding an SLBP polypeptide, or to its complement. Hybridizing nucleic acids of the type described herein can be used as a cloning probe, a primer (e.g., a PCR primer), or a diagnostic probe. Nucleic acids that hybridize to the nucleotide sequence represented by SEQ ID NO:1, are considered "antisense oligonucleotides."

High stringency conditions are hybridizing at 68° C. in 5×SSC/5×Denhardt's solution/1.0% SDS, or in 0.5 M $NaHPO_4$ (pH 7.2)/1 mM EDTA/7% SDS, or in 50% formamide/0.25 M $NaHPO_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM $NaHPO_4$ (pH 7.2)/1 mM EDTA/5% SDS at 50° C., or in 40 mM $NaHPO_4$ (pH 7.2) 1 mM EDTA/1% SDS at 50° C. Stringent conditions include washing in 3×SSC at 42° C. The parameters of salt concentration and temperature can be varied to achieve the optimal level of identity between the probe and the target nucleic acid. Additional guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

Also included in the invention are genetic constructs (e.g., vectors and plasmids) that include an SLBP nucleic acid described herein, operably linked to a transcription and/or translation sequence to enable expression, e.g., expression vectors. A selected nucleic acid, e.g., a DNA molecule encoding an SLBP polypeptide, is "operably linked" to another nucleic acid molecule, e.g., a promoter, when it is positioned either adjacent to the other molecule or in the same or other location such that the other molecule can control transcription and/or translation of the selected nucleic acid.

Also included in the invention are various engineered cells, e.g., transformed host cells, which contain an SLBP nucleic acid described herein. A transformed cell is a cell into which (or into an ancestor of which) has been introduced, by means of recombinant DNA techniques, a nucleic acid encoding an SLBP polypeptide. Both prokaryotic and eukaryotic cells are included. Mammalian cells transformed with an SLBP nucleic acid can include host cells for an attaching enteric organism, e.g., intestinal cells, HeLa cells, and mouse embryonic fibroblasts. Prokaryotic cells can include bacteria, e.g., *Escherichia coli*. An engineered cell exemplary of the type included in the invention is an *E. coli* strain that expresses SLBP.

Certain SLBP polypeptides are also included within the present invention. Examples of such SLBP polypeptides are SLBP polypeptides and fragments, such as the one shown as SEQ ID NO:2. Also included within the present invention are certain fragments of SLBP polypeptides, e.g., fragments of SLBP polypeptides may include at least one mRNA binding domain, or other useful portion of a full-length SLBP polypeptide. For example, useful fragments of SLBP polypeptides include, but are not limited to, fragments having mRNA binding activity, and portions of such fragments.

The terms "protein" and "polypeptide" both refer to any chain of amino acids, regardless of length or post-translational modification (e.g., glycosylation or phosphorylation). Thus, the terms "SLBP protein," and "SLBP polypeptide," include full-length naturally occurring isolated proteins, as well as recombinantly or synthetically produced polypeptides that correspond to the full-length naturally occurring proteins, or to a fragment of the full-length naturally occurring or synthetic polypeptide.

As discussed above, the term "SLBP polypeptide" includes biologically active fragments of naturally occurring or synthetic SLBP polypeptides. Fragments of a protein can be produced by any of a variety of methods known to those skilled in the art, e.g., recombinantly, by proteolytic digestion, and/or by chemical synthesis. Internal or terminal fragments of a polypeptide can be generated by removing one or more nucleotides from one end (for a terminal fragment) or both ends (for an internal fragment) of a nucleic acid that encodes the polypeptide. Expression of such mutagenized DNA can produce polypeptide fragments. Digestion with "end-nibbling" endonucleases can thus generate DNAs that encode an array of fragments. DNAs that encode fragments of a protein can also be generated, e.g., by random shearing, restriction digestion, chemical synthesis of oligonucleotides, amplification of DNA using the polymerase chain reaction, or a combination of the above-discussed methods. Fragments can also be chemically synthesized using techniques known in the art, e.g., conventional Merrifield solid phase FMOC or t-Boc chemistry. For example, peptides of the present invention can be arbitrarily divided into fragments of desired length with no overlap of the fragments, or divided into overlapping fragments of a desired length.

A purified or isolated compound is a composition that is at least 75% by weight the compound of interest, e.g., an SLBP polypeptide. In general, the preparation is at least 80% (e.g., at least 90%, 95%, 96%, 97%, 98%, 99%, or 100%) by weight the compound of interest. Purity can be measured by any appropriate standard method, e.g., column chromatography, polyacrylamide gel electrophoresis, or HPLC analysis.

In certain embodiments, SLBP polypeptides include sequences substantially identical to all or portions of a naturally occurring SLBP polypeptide. Polypeptides "substantially identical" to the SLBP polypeptide sequences described herein have an amino acid sequence that is at least 75% (e.g., at least 80%, 90%, 95%, 96%, 97%, 98%, 99%, or 100%), identical to the amino acid sequences of the SLBP polypeptides represented by SEQ ID NO:2 (measured as described herein). For purposes of comparison, the length of the reference SLBP polypeptide sequence is at least 50 amino acids, e.g., at least 60 or 80 amino acids.

In the case of polypeptide sequences that are less than 100% identical to a reference sequence, the non-identical positions are preferably, but not necessarily, conservative substitutions for the reference sequence. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Where a particular polypeptide is said to have a specific percent identity to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. It also might be a 100 amino acid long polypeptide that is 50% identical to the reference polypeptide over its entire length.

SLBP polypeptides of the invention include, but are not limited to, recombinant polypeptides and natural polypeptides. Also included are nucleic acid sequences that encode forms of SLBP polypeptides in which naturally occurring amino acid sequences are altered or deleted. Certain nucleic acids of the present invention may encode polypeptides that are soluble under normal physiological conditions.

Also within the invention are nucleic acids encoding fusion proteins in which a portion of an SLBP polypeptide is fused to an unrelated polypeptide to create a fusion protein. For example, the polypeptide can be fused to a hexa-histidine tag or a FLAG tag to facilitate purification of bacterially expressed polypeptides or to a hemagglutinin tag or a FLAG tag to facilitate purification of polypeptides expressed in eukaryotic cells. The invention also includes, for example, isolated polypeptides (and the nucleic acids that encode these polypeptides) that include a first portion and a second portion; the first portion includes, e.g., an SLBP polypeptide, and the second portion includes an immunoglobulin constant (Fc) region or a detectable marker.

In one aspect, SLBP can be fused to a NLS. NLSs are known in the art and can consist of one or more short sequences of positively charged lysines or arginines exposed on the protein surface. For example, classical NLSs can be classified as either monopartite or bipartite. The first NLS to be discovered was the sequence PKKKRKV in the SV40 Large T-antigen (a monopartite NLS) (Kalderon et al., Cell 39:499-509, 1984). The NLS of nucleoplasmin, KR[PAAT-KKAGQA]KKKK, is the prototype of the ubiquitous bipartite signal: two clusters of basic amino acids, separated by a spacer of about 10 amino acids (Dingwall et al., J Cell Biol 107:841-9, 1988). Both signals are recognized by importin α. Importin α contains a bipartite NLS itself, which is specifically recognized by importin β. The latter can be considered the actual import mediator. There are many other non-classical NLSs such as the acidic M9 domain of hnRNP A1, the sequence KIPIK in yeast transcription repressor Matα2, and the complex signals of U snRNPs. Most of these NLSs appear to be recognized directly by specific receptors of the importin β family without the intervention of an importin α-like protein (Mattaj et al., Annu Rev Biochem 67:265-306, 1998).

The fusion partner can be, for example, a polypeptide that facilitates secretion, e.g., a secretory sequence. Such a fused polypeptide is typically referred to as a preprotein. The secretory sequence can be cleaved by the host cell to form the mature protein. Also within the invention are nucleic acids that encode an SLBP polypeptide fused to a polypeptide sequence to produce an inactive preprotein. Preproteins can be converted into the active form of the protein by removal of the inactivating sequence. SLBP may also be targeted to an epithelial surface, e.g., by fusing SLBP to polypeptides that are targeted to the epithelial surface or by modifying the protein with a glycosylphosphatidylinositol anchor.

Pharmaceutical Compositions

Also described herein are pharmaceutical compositions, which include compounds identified as active ingredients by a method described herein. Exemplary pharmaceutical compositions include, e.g., SLBP fused to a NLS, e.g., where the SLBP comprises a polypeptide that has at least 90, 92, 95, 96, 97, 98, or 99% identity to the amino acid sequence of SEQ ID NO:2, and vectors encoding a SLBP or a SLBP fused to a NLS, e.g., wherein the nucleic acid sequence encoding for SLBP comprises a nucleic acid sequence that is at least 90% identical to SEQ ID NO:1.

The compounds and agents, e.g., small molecules, nucleic acids, polypeptides, and antibodies (all of which can be referred to herein as "active compounds"), can be incorporated into pharmaceutical compositions. Such compositions typically include the active compound and a pharmaceutically acceptable carrier. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions. The pharmaceutical compositions can be included in a container, pack, or dispenser together with instructions for administration.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, a polyol (for example, glycerol, propylene glycol, and liquid polyethylene glycol, and the like), or a suitable mixture thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be achieved by including an agent that delays absorption, e.g., aluminum monostearate or gelatin, in the composition.

Sterile injectable solutions can be prepared by incorporating the active compound in the required amount in an appropriate solvent with one or a combination of ingredients enumerated above, as required, followed by filtered sterilization. Typically, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Injectable compositions may contain various carriers such as vegetable oils, dimethylacetamide, dimethylformamide, ethyl lactate, ethyl carbonate, isopropyl myristate, ethanol, and polyols (glycerol, propylene glycol, liquid polyethylene glycol, and the like). For intravenous injections, the compounds may be administered by the drip method, whereby a pharmaceutical composition containing the active compound(s) and a physiologically acceptable excipient is infused. Physiologically acceptable excipients may include, for example, 5% dextrose, 0.9% saline, Ringer's solution or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil.

Oral compositions typically include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Alternatively, the pharmaceutical composition can be formulated as a chewing gum, lollipop, or the like.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the patient to be treated.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

In all of the methods described herein, appropriate dosages of SLBP can readily be determined by those of ordinary skill in the art of medicine, e.g., by monitoring the patient for signs of disease amelioration or inhibition, and increasing or decreasing the dosage and/or frequency of treatment as desired. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue, e.g., bone or cartilage, in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

For the compounds described herein, an effective amount, e.g., of a protein or polypeptide (i.e., an effective dosage), ranges from about 0.001 to 30 mg/kg body weight, e.g., about 0.01 to 25 mg/kg body weight, e.g., about 0.1 to 20 mg/kg body weight. The protein or polypeptide can be administered one time per day, twice per day, one time per week, twice per week, for between about 1 to 52 weeks per year, e.g., between 2 to 50 weeks, about 6 to 40 weeks, or for about 4, 5, or 6 weeks. The skilled artisan will appreciate that certain factors influence the dosage and timing required to effectively treat a patient, including but not limited to the type of patient to be treated, the severity of the disease or disorder, previous treatments, the general health and/or age of the patient, and other diseases present. Moreover, treatment of a patient with a therapeutically effective amount of a protein, polypeptide, antibody, nucleic acid, or other compound can include a single treatment or, preferably, can include a series of treatments.

For antibodies, a useful dosage is 5 mg/kg of body weight (typically 3 mg/kg to 20 mg/kg). Typically, partially human antibodies and fully human antibodies have a longer half-life within the human body than other antibodies. Accordingly, lower dosages and less frequent administration are possible. Modifications such as lipidation can be used to stabilize antibodies or other therapeutic proteins and to enhance uptake and tissue penetration. A method for lipidation of antibodies is described by Cruikshank et al. (J. Acquir. Immune Defic. Syndr. Hum. Retrovirol. 14:193, 1997). Alternatively, an antibody or a fragment thereof may be joined to a protein transduction domain, e.g., an HIV Tat-1 activator domain or the homeodomain of Antennapedia transcription factor (for review, see Heng and Cao, Medical Hypotheses 64:1105-8, 2005). Fusion proteins thus generated have been found to transduce into the cells of tissues in a mouse model system (Schwarze et al., Science 285:1569-1572, 1999).

If the compound is a small molecule, exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Nucleic acid molecules (e.g., encoding SLBP, e.g., a fusion NLS-SLBP) of the invention can be inserted into vectors and used as gene therapy vectors. Gene therapy vectors can be delivered to a subject by, for example, intravenous injection, local administration (see. e.g., U.S. Pat. No. 5,328,470) or by stereotactic injection (see. e.g., Chen et al., Proc. Natl. Acad. Sci. USA 91:3054-3057, 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Inhibitory Nucleic Acids

Nucleic acid molecules (e.g., RNA molecules) can be used to increase SLBP expression or activity by inhibiting expression or activity of a SLBP repressor. A siRNA, antisense RNA, a ribozyme, or aptamer, which can specifically inhibit expression of a SLBP repressor or inhibit activity of a SLBP repressor will induce expression of SLBP. In some aspects, a cell or subject can be treated with a compound that increases expression of SLBP. Such approaches include oligonucleotide-based therapies such as RNA interference, antisense, ribozymes, and aptamers.

i. siRNA Molecules

RNA interference (RNAi) is a process whereby double-stranded RNA (dsRNA, also referred to herein as siRNAs or ds siRNAs, for double-stranded small interfering RNAs) induces the sequence-specific degradation of homologous mRNA in animals and plant cells (Hutvagner and Zamore, Curr Opin Genet Dev 12:225-232, 2002; Sharp, Genes Dev 15:485-490, 2001). In mammalian cells, RNAi can be triggered by 21-nucleotide (nt) duplexes of small interfering RNA (siRNA) (Chiu et al., Mol Cell 10:549-561, 2002; Elbashir et al., Nature 411:494-498, 2001), or by micro-RNAs (miRNA), functional small-hairpin RNA (shRNA), or other dsRNAs which are expressed in vivo using DNA templates with RNA polymerase III promoters (Zeng et al., Mol Cell 9:1327-1333, 2002; Paddison et al., Genes Dev 16:948-958, 2002; Lee et al., Nature Biotechnol 20:500-505, 2002; Paul et al., Nature Biotechnol 20:505-508, 2002; Tuschl, Nature Biotechnol 20:440-448, 2002; Yu et al., Proc Natl Acad Sci USA 99:6047-6052, 2002; McManus et al., RNA 8:842-850, 2002; Sui et al., Proc Natl Acad Sci USA 99:5515-5520, 2002).

The nucleic acid molecules or constructs can include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can transcribed in vitro from a DNA template, or in vivo from, e.g., shRNA. The dsRNA molecules can be designed using any method known in the art; a number of algorithms are known, and are commercially available. Gene walk methods can be used to optimize the inhibitory activity of the siRNA.

The nucleic acid compositions can include both siRNA and modified siRNA derivatives, e.g., siRNAs modified to alter a property such as the pharmacokinetics of the composition, for example, to increase half-life in the body, as well as engineered RNAi precursors.

siRNAs can be delivered into cells by methods known in the art, e.g., cationic liposome transfection and electroporation. siRNA duplexes can be expressed within cells from engineered RNAi precursors, e.g., recombinant DNA constructs using mammalian Pol III promoter systems (e.g., H1 or U6/snRNA promoter systems (Tuschl 2002, supra) capable of expressing functional double-stranded siRNAs; (Bagella et al., J Cell Physiol 177:206 213, 1998; Lee et al., 2002, supra; Miyagishi et al., 2002, supra; Paul et al., 2002, supra; Yu et al., 2002, supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998, supra; Lee et al., 2002, supra; Miyagishi et al., 2002, supra; Paul et al., 2002, supra; Yu et al., 2002, supra; Sui et al., 2002, supra). Constructs containing siRNA sequence under the control of T7 promoter also make functional siRNAs when co-transfected into the cells with a vector expression T7 RNA polymerase (Jacque, 2002, supra).

ii. Antisense Nucleic Acids

An "antisense" nucleic acid can include a nucleotide sequence that is complementary to a "sense" nucleic acid encoding a protein, e.g., complementary to the coding strand of a double-stranded cDNA molecule or complementary to a SLBP repressor mRNA sequence. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence (e.g., the 5' and 3' untranslated regions).

An antisense nucleic acid can be designed such that it is complementary to the entire coding region of a target mRNA, but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

In some embodiments, the antisense nucleic acid molecule is an α-anomeric nucleic acid molecule. An α-anomeric nucleic acid molecule forms specific double-stranded hybrids with complementary RNA in which, contrary to the usual β-units, the strands run parallel to each other (Gaultier et al., Nucleic Acids Res 15:6625-6641, 1987). The antisense nucleic acid molecule can also comprise a 2'-o-methylribonucleotide (Inoue et al., Nucleic Acids Res 15:6131-6148, 1987) or a chimeric RNA-DNA analogue (Inoue et al., FEBS Lett 215:327-330, 1987).

In some embodiments, the antisense nucleic acid is a morpholino oligonucleotide (see, e.g., Heasman, Dev Biol 243:209-14, 2002; Iversen, Curr Opin Mol Ther 3:235-8, 2001; Summerton, Biochim Biophys Acta 1489:141-58, 1999).

Target gene expression can be inhibited by targeting nucleotide sequences complementary to a regulatory region (e.g., promoters and/or enhancers) to form triple helical structures that prevent transcription of the Spt5 gene in target cells. See generally, Helene, Anticancer Drug Des 6:569-84, 1991; Helene, Ann NY Acad Sci 660:27-36, 1992; and Maher, Bioassays 14:807-15, 1992. The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

iii. Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target nucleic acid can include one or more sequences complementary to a nucleotide sequence of a cDNA of a SLBP repressor, and a sequence having known catalytic sequence responsible for mRNA cleavage (see U.S. Pat. No. 5,093,246 or Haselhoff and Gerlach, Nature 334:585-591, 1988). For example, a derivative of a Tetrahymena L-19 IVS RNA can be constructed in which the nucleotide sequence of the active site is complementary to the nucleotide sequence to be cleaved in a target mRNA. See, e.g., Cech et al., U.S. Pat. No. 4,987,071; and Cech et al., U.S. Pat. No. 5,116,742. Alternatively, a target mRNA can be used to select a catalytic RNA having a specific ribonuclease activity from a pool of RNA molecules. See, e.g., Bartel and Szostak, Science 261:1411-1418, 1993.

iv. Aptamers

Aptamers are short oligonucleotide sequences which can specifically bind specific proteins. It has been demonstrated that different aptameric sequences can bind specifically to different proteins, for example, the sequence GGNNGG where N=guanosine (G), cytosine (C), adenosine (A) or thymidine (T) binds specifically to thrombin (Bock et al., Nature 355:564-566, 1992; and U.S. Pat. No. 5,582,981, Toole et al., 1996). Methods for selection and preparation of such RNA aptamers are known in the art (see, e.g., Famulok, Curr Opin Struct Biol 9:324, 1999; Herman and Patel, J Sci 287:820-825, 2000; Kelly et al., J Mol Biol 256:417, 1996; and Feigon et al., Chem Biol 3:611, 1996).

Administration of Inhibitory Nucleic Acid Molecules

The inhibitory nucleic acid molecules described herein can be administered to a subject (e.g., by direct injection at a tissue site), or generated in situ such that they hybridize with or bind to cellular mRNA and/or genomic DNA encoding a target protein to thereby inhibit expression of the protein, e.g., by inhibiting transcription and/or translation. Alternatively, inhibitory nucleic acid molecules can be modified to target selected cells and then administered systemically. For systemic administration, inhibitory nucleic acid molecules can be modified such that they specifically bind to receptors or antigens expressed on a selected cell surface, e.g., by linking the inhibitory nucleic acid molecules to peptides or antibodies that bind to cell surface receptors or antigens. The inhibitory nucleic acid molecules can also be delivered to cells using the vectors described herein. To achieve sufficient intracellular concentrations of the inhibitory nucleic acid molecules, vector constructs in which the inhibitory nucleic acid molecule is placed under the control of a strong promoter can be used.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

Methods of Determining a Prognosis for a Subject Infected with HIV

Described herein are a variety of methods of determining a prognosis for a subject infected with HIV. An increased susceptibility to develop AIDS exists if a subject has a level of one or more histone-related protein (e.g., SLBP, H1X, H1.2, H1.3, H2A.Z, H2B, and H4) that is less than or about the same as its respective reference value. Determining, ascertaining, or assaying the level of the histone-related protein is included in the concept of determining susceptibility to AIDS. Such determination is useful, for example, for purposes of diagnosis, treatment selection (e.g., of the same, new, or different treatments), and genetic counseling. Thus, the methods described herein can include detecting a level of one or more of SLBP, H1X, H1.2, H1.3, H2A.Z, H2B, and H4, as described herein for the subject.

Described herein are a variety of methods of reducing a risk of an HIV infection, or treating, or reducing a risk of developing, AIDS in a subject, e.g., a subject diagnosed as being infected with HIV, e.g., HIV-1. For example, the subject can be treated with a therapeutically effective amount of SLBP to increase the level of SLBP in a subject and thereby, reducing the risk of an HIV infection or reducing the risk of developing AIDS.

The methods described herein include determining a level of one or more histone-related protein (e.g., SLBP, H1X, H1.2, H1.3, H2A.Z, H2B, and H4) in a subject, e.g., a human. In some embodiments, an association between a prognosis for a subject infected with HIV, e.g., HIV-1, is determined by the relative level of the one or more histone-related protein (e.g., SLBP, H1X, H1.2, H1.3, H2A.Z, H2B, and H4) in a sample from the subject and an uninfected reference individual, i.e., a reference value. Thus the methods can include obtaining and analyzing a sample from a suitable reference individual.

Samples that are suitable for use in the methods described herein contain protein or genetic material, e.g., RNA. Non-limiting examples of sources of samples include blood, plasma, serum, saliva, sputum, mucus, semen, cerebral spinal fluid. A sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of samples from a subject such as a combination of a tissue and fluid sample. The sample itself will typically consist of nucleated cells (e.g., blood or buccal cells), tissue, etc., removed from the subject. The subject can be an adult, child, fetus, or embryo. In some embodiments, the sample is obtained prenatally, either from a fetus or embryo or from the mother (e.g., from fetal or embryonic cells in the maternal circulation). Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a saliva sample.

The sample may be processed before the detecting step. For example, protein or RNA in a cell or tissue sample can be separated from other components of the sample. The sample can be concentrated and/or purified to isolate protein or RNA. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract protein or RNA. See, e.g., *Current Protocols in Molecular Biology*, Ausubel et al., Eds., John Wiley & Sons, 2003). All samples obtained from a subject, including those subjected to any sort of further processing, are considered to be obtained from the subject. For example, amplification of nucleic acids from a sample from a subject, where desirable, can be accomplished using methods known in the art, e.g., PCR, and are considered to be obtained from the subject.

Detecting a protein or RNA can also include or consist of reviewing a subject's medical history, where the medical history includes information regarding the identity, presence or absence of one or more genetic markers in the subject, e.g., results of a genetic test.

In some embodiments, to determine the level of a histone-related protein, a biological sample that includes nucleated cells (such as blood, a cheek swab, or saliva) is prepared and analyzed for the presence or absence of preselected markers.

Such diagnoses may be performed by diagnostic laboratories. Alternatively, diagnostic kits containing probes or nucleic acid arrays useful in, e.g., determining the presence of one or more protein or RNA levels can be manufactured and sold to health care providers or to private individuals for self-diagnosis. Diagnostic or prognostic tests can be performed as described herein or using well known techniques, such as described in U.S. Pat. No. 5,800,998.

Results of these tests, and optionally interpretive information, can be returned to the subject, the health care provider, medical caregiver, physician, nurse, or to a third party payor. The results can be used in a number of ways. The information can be, e.g., communicated to the tested subject, e.g., with a prognosis and optionally interpretive materials that help the subject understand the test results and prognosis. The information can be used, e.g., by a health care provider, to determine whether to administer a specific drug, or whether a subject should be assigned to a specific category, e.g., a category associated with a specific disease phenotype, or with drug response or non-response. The information can be used, e.g., by a third party payor such as a healthcare payor (e.g., insurance company or HMO) or other agency, to determine whether or not to reimburse a health care provider for services to the subject, or whether to approve the provision of services to the subject. As another example, a drug or treatment may be indicated for individuals with a certain level of biomarker, and the insurance company would only reimburse the health care provider (or the insured individual) for prescription or purchase of the drug if the insured individual has a certain level of biomarker, e.g., a level below that is less than or about the same as a reference value. The level of the biomarker in a subject may be ascertained by using any of the methods described herein.

Information gleaned from the methods described herein can also be used to select or stratify subjects for a clinical trial. For example, the presence of a selected haplotype described herein can be used to select a subject for a trial. The information can optionally be correlated with clinical information about the patient, e.g., diagnostic or prognostic information.

Skilled practitioners will appreciate that a patient can be identified as at risk for HIV or AIDS by any method known in the art, e.g., by a physician or other medical personnel. In some embodiments, the methods described herein are performed in conjunction with a standard HIV/AIDS workup, e.g., including laboratory tests (e.g., complete blood count (CBC); CD4 cell count; measurement of HIV RNA level; and cervical and anal Pap smears).

Methods for determining prognosis can include, e.g., determining a level of one or more (e.g., two, three, four, five, six, or seven) of SLBP, H1X, H1.2, H1.3, H2A.Z, H2B, and H4 to provide a test value, and comparing the test value to an its respective reference value, e.g., a value that represents a threshold level, below which the subject can be diagnosed with a greater risk of developing AIDS. The reference can also be a range of values, e.g., that indicate severity of AIDS in the subject. A suitable reference value can be determined by methods known in the art, e.g., reference cohort of normal subjects or subjects with AIDS. A reference value can be a mean or median level of a biomarker of HIV/AIDS as described herein, or any other statistically significant cutoff.

Therefore, included herein are methods for predicting the severity of HIV infection or time to development of AIDS in a subject. The methods include obtaining a sample from a subject, and evaluating the presence and/or level of one or more of SLBP, H1X, H1.2, H1.3, H2A.Z, H2B, and H4 in the sample, and comparing the presence and/or level with one or more references, e.g., a control reference that represents a threshold level of SLBP, H1X, H1.2, H1.3, H2A.Z, H2B, and H4, e.g., a level in an uninfected subject, and/or a disease reference that represents a level of SLBP, H1X, H1.2, H1.3, H2A.Z, H2B, and H4 associated with HIV or AIDS, e.g., a level in a subject infected with HIV or suffering from AIDS. The presence and/or level of a protein or RNA can be evaluated using methods known in the art, e.g., using quantitative immunoassay methods such as enzyme linked immunosorbent assays (ELISAs), immunoprecipitation, immunofluorescence, enzyme immunoassay (EIA), radioimmunoassay (RIA), Western blot analysis, PCR, and Northern blot analysis. In some embodiments, the methods include contacting an agent that selectively binds to the SLBP, H1X, H1.2, H1.3, H2A.Z, H2B, and H4 protein (such as an antibody or antigen-binding portion thereof) with a sample, to evaluate the level of protein in the sample. In some embodiments, the antibody bears a detectable label. Antibodies can be polyclonal, or more preferably, monoclonal. An intact antibody, or an antigen-binding fragment thereof (e.g., Fab or F(ab')2) can be used. The term "labeled," with regard to an antibody encompasses direct labeling of the antibody by coupling (i.e., physically linking) a detectable substance to the antibody, as well as indirect labeling of the antibody by reactivity with a detectable substance. Examples of detectable substances are known in the art and include chemiluminescent, fluorescent, radioactive, or colorimetric labels. For example, detectable substances can include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, or $^{3}H$.

In some embodiments, high throughput methods, e.g., protein or gene chips as are known in the art (see. e.g., Ch. 12, "Genomics," in Griffiths et al., Eds. *Modern Genetic Analysis*, 1999, W. H. Freeman and Company; Ekins and Chu, Trends in Biotechnology 1999; 17:217-218; MacBeath and Schreiber, Science 289(5485):1760-1763, 2000; Simpson, Proteins and Proteomics: A Laboratory Manual, Cold Spring Harbor Laboratory Press; 2002; Hardiman, Microarrays Methods and Applications: Nuts & Bolts, DNA Press, 2003), can be used to detect the presence and/or level of SLBP, H1X, H1.2, H1.3, H2A.Z, H2B, and H4.

In some embodiments, microfluidic (e.g., "lab-on-a-chip") devices can be used in the present methods for detection and quantification of biomarkers of HIV and AIDS as described herein in a sample. Such devices have been successfully used for microfluidic flow cytometry, continuous size-based separation, and chromatographic separation. In particular, such devices can be used for the isolation of specific biological particles such as specific proteins (e.g., a biomarker of HIV and AIDS as described herein) from complex mixtures such as serum, plasma, or whole blood. A variety of approaches may be used to separate the biomarker proteins from a heterogeneous sample. For example, some techniques can use functionalized materials to capture the proteins using functionalized surfaces that bind to the target cell population. The functionalized materials can include surface-bound capture moieties such as antibodies or other specific binding molecules, such as aptamers, as are known in the art. Accordingly, such microfluidic chip technology may be used in diagnostic and prognostic devices for use in the methods described herein. For examples, see, e.g., Lion et al., Electrophoresis 24:3533-3562, 2003; Fortier et al., Anal. Chem. 77:1631-1640, 2005; U.S. Patent Publication No. 2009/0082552; and U.S. Pat. No. 7,611,834. Also included in the present application are microfluidic devices comprising binding moieties, e.g., antibodies or antigen-binding fragments thereof that bind specifically to the biomarkers of HIV and AIDS as described herein.

In some embodiments, the presence and/or level of the biomarker proteins is comparable to the presence and/or level of the protein(s) in a disease reference, and the subject has one or more symptoms associated with HIV or AIDS, then the subject has HIV or AIDS. In some embodiments, the subject has no overt signs or symptoms of HIV or AIDS, but the presence and/or level of one or more of the proteins evaluated is lower than or about the same as the reference value, then the subject has an increased risk of being infected with HIV and developing AIDS. In some embodiments of the present methods, the sample is or includes blood, plasma, and/or serum, or a portion or subfraction thereof. In some embodiments, once it has been determined that a person has HIV or AIDS, or has an increased risk of developing HIV or AIDS, then a treatment, e.g., as known in the art or as described herein, can be administered. The efficacy of the treatment can be monitored using the methods described herein.

Kits

Also within the scope of the invention are kits for detecting the presence of one or more of SLBP, H1X, H1.2, H1.3, H2A.Z, H2B, and H4 in a biological sample. For example, the kit can include a compound or agent capable of detecting one or more of SLBP, H1X, H1.2, H1.3, H2A.Z, H2B, and H4 protein or mRNA in a biological sample; and a standard. The compound or agent can be packaged in a suitable container. The kit can further comprise instructions for using the kit to detect one or more of SLBP, H1X, H1.2, H1.3, H2A.Z, H2B, and H4 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also include a buffering agent, a preservative, or a protein stabilizing agent. The kit can also include components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a HIV or AIDS involving one or more of SLBP, H1X, H1.2, H1.3, H2A.Z, H2B, and H4 genes.

Kits for use in self-testing can also be provided. For example, such test kits can include devices and instructions that a subject can use to obtain a sample, e.g., of blood, without the aid of a health care provider.

Kits as provided herein can also include a mailer, e.g., a postage paid envelope or mailing pack, that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms, e.g., the test requisition form, and the container holding the sample, can be coded, e.g., with a bar code, for identifying the subject who provided the sample.

In some embodiments, the kits can include one or more reagents for processing a biological sample. For example, a kit can include reagents for isolating protein or mRNA from a biological sample and/or reagents for amplifying isolated mRNA (e.g., reverse transcriptase, primers for reverse transcription or PCR amplification, or dNTPs). The kits can also, optionally, contain one or more reagents for detectably-labeling an mRNA, mRNA amplicon, which reagents can include, e.g., an enzyme such as a Klenow fragment of DNA polymerase, T4 polynucleotide kinase, one or more detectably-labeled dNTPs, or detectably-labeled gamma phosphate ATP (e.g., $^{33}$P-ATP).

In some embodiments, the kits can include a software package for analyzing the results of, e.g., a microarray analysis or expression profile.

A subject can be selected on the basis that they have, or are at risk of developing AIDS. It is well within the skills of an ordinary practitioner to recognize a subject that has, or is at risk of developing, an HIV infection. A subject that has, or is at risk of developing. AIDS is one infected with HIV, e.g., HIV-1, and having one or more symptoms of the condition or one or more risk factors for developing the condition. Symptoms of HIV infection and AIDS are known to those of skill in the art and include, without limitation, influenza or mononucleosis-like illness called acute HIV infection, the most common symptoms of which may include fever, lymphadenopathy, pharyngitis, rash, myalgia, malaise, mouth and esophageal sores, headache, nausea, vomiting, enlarged liver/spleen, weight loss, thrush, neurological symptoms, moderate and unexplained weight loss, recurring respiratory tract infections (such as sinusitis, bronchitis, otitis media, pharyngitis), prostatitis, skin rashes, oral ulcerations, oral candidiasis (thrush), tuberculosis, recurrences of herpes simplex eruptions, shingles, Epstein-Barr virus-induced B-cell lymphomas, Kaposi's sarcoma, pneumonia caused by *Pneumocystis jirovecii*, and infection with cytomegalovirus or *Mycobacterium avium* complex.

The subjects can also be those undergoing any of a variety of anti-retroviral therapy treatments. Thus, for example, subjects can be those being treated with one or more of an entry inhibitor (e.g., enfuvirtide (FUZEON®)), a CCR5 receptor antagonist (e.g., maraviroc (SELZENTRY®)), a reverse-transcriptase inhibitor (e.g., zidovudine (RETROVIR®), a protease inhibitor (e.g., atazanavir (REYATAZ®), darunavir (PREZISTA®), fosamprenavir (LEXIVA®), and ritonavir (NORVIR®)), an integrase inhibitor (e.g., Raltegravir (ISENTRESS®)), and a maturation inhibitor (e.g., Bevirimat, Vivecon).

Methods of Screening Test Compounds

Included herein are methods for screening test compounds, e.g., polypeptides, polynucleotides (including inhibitory nucleic acids), inorganic or organic large or small molecule test compounds, to identify agents useful to increase expression of SLBP.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-66, 1997). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known inducer of SLBP expression, or a first small molecule identified as capable of inducing SLBP expression, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell, and one or more effects of the test compound is evaluated. In some embodiments, a cultured or primary cell for example, the ability of the test compound to increase SLBP expression can be evaluated. In other embodiments, a cultured or primary cell for example, the ability of the test compound to increase SLBP expression can be evaluated, e.g., assay SLBP mRNA or protein levels. Methods for evaluating these effects are known in the art. For example, ability to modulate expression of a protein can be evaluated at the gene or protein level, e.g., using quantitative PCR or immunoassay methods. In some embodiments, high throughput methods (as described above) can be used to detect an effect on SLBP.

A test compound that has been screened by a method described herein and determined to increase SLBP expression can be considered a candidate compound. A candidate compound that has been screened, e.g., in an in vivo model of a disorder, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that increase SLBP expression) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds useful in reducing a risk of an HIV infection, or in treating, or reducing a risk of developing, AIDS. A variety of techniques useful for determining the structures of "hits" can be used in the methods described herein, e.g., NMR, mass spectrometry, gas chromatography equipped with electron capture detectors, and fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model. The animal can be monitored for a change in the disorder, e.g., for an improvement in a parameter of the disorder, e.g., a parameter related to clinical outcome. In some embodiments, the parameter is level of SLBP. In some embodiments, the subject is a human.

EXAMPLES

The invention is further described in the following examples, which do not limit the scope of the invention described in the claims.

Example 1

Cell Culture and SILAC Labeling

Cells were cultured either in SILAC® RPMI-1640 labeling medium, designated as "Heavy" medium (containing 10% dialyzed FBS and supplemented with 100 mg/L [U-13C6]-L-Lysine (K+6), 100 mg/L [U-13C6, 15N4]-L-Arginine (R+10) and 1× L-Glutamine (Invitrogen, Carlsbad, Calif.)) or in RPMI-1640 medium (Invitrogen), designated as "Light" medium (containing 10% dialyzed FBS and supplemented with 100 mg/L L-Lysine, 100 mg/L L-Arginine, 1× L-Glutamine).

Protein Extraction and Preparation

Protein pellets were mixed with CELLYTIC® M reagent (Sigma, St. Louis, Mo.) for 15 minutes on a shaker before 10 minutes of centrifugation at 12,800 g to separate lysed exosomal protein from supernatant. Micro BCA Protein Assay Kit (Thermo Fisher Scientific, Rockford, Ill.) was used to determine protein concentration. Both heavy and light exosomal protein samples were mixed 1:1 before running on NUPAGE® 4-12% Bis-Tris precast Gel (Invitrogen) by using XCell SURELOCK® Mini-Cell (Invitrogen). The gel was stained by SIMPLYBLUE® SafeStain (Invitrogen). The entire sample lane from the destained gel was cut into ten equal gel pieces for fractionation. Each piece was washed three times with 50% acetonitrile/50% HPLC grade water prior to mass spectrometric analysis.

Mass Spectrometry and Quantitative Analysis

Gel pieces were washed, reduced with DTT and alkylated with iodoacetamide. Gels were then digested with modified trypsin (Promega, Madison, Wis.) at pH 8.3 overnight at 37° C. with shaking. The resulting peptide mixtures from each gel piece were analyzed separately by data dependent microcapillary reversed phase liquid chromatography tandem mass spectrometry (LC/MS/MS). LC/MS/MS was performed using an EASY-nLC nanoflow HPLC (Thermo Fisher Scientific, Waltham, Mass.) with a self-packed 75 µm id×15 cm $C_{18}$ column coupled to a LTQ-Orbitrap XL mass spectrometer (Thermo Fisher Scientific) using a MS-FT target value of 5.0E5 and a MS/MS-IT target value of 3.0E4 in data dependent acquisition (DDA)/positive ion mode. Generated MS/MS spectra were searched against the reversed and concatenated non-redundant Human IPI database (version 3.68) by using Mascot (Matrix Science, London, U.K.; version 2.2). Protein quantitation was achieved by employing MaxQuant software (version 1.0.13.13) (maxquant.org) requiring at least two peptides per protein (one razor and one unique) for quantitation. Normalized SILAC ratios were used for all subsequent interpretation.

Western Blotting

Cellular protein was harvested, quantified by micro BCA assay and run on NUPAGE® 4-12% Bis-Tris precast Gel (Invitrogen) by using XCell SURELOCK® Mini-Cell (Invitrogen). After electrophoresis, the resolved proteins were transferred onto PVDF membrane by using XCell II® Blot Module. Upon the completion of transfer, membranes were blocked for 1 hour before adding anti-ACTB (BD Biosciences. San Diego, Calif.), anti-CD82, anti-CD38, anti-ANXA5 and anti-LDH8 (Epitomics) and incubating overnight at 4° C. Finally, proteins were detected and analyzed by ODYSSEY® CLx Infrared Imaging System (LI-COR, Lincoln, Nebr.) after incubation with IRDye® 680LT or 800CW conjugated secondary antibodies for 30 minutes followed by four PBST washes.

Data Analysis

1. Protein Quantitation:

Two prerequisites were applied to ensure greater confidence in the accuracy of the MS derived peptide ratios: 1.) Two or more quantifiable peptides were required to be associated with a given protein; 2.) In order to determine significantly up- and down-regulated protein candidates, conservative cut-off values were calculated as follows:

median (average of Normalized H/L Ratios of all quantified proteins)±2× standard deviation (average of H/L Variability of all quantified proteins).

2. Histogram of SILAC Ratio Distribution:

Normalized H/L Ratios of all quantified proteins were $\log_2$ transformed, and plotted by using SigmaPlot (version 10.0).

3. DAVID Analysis:

To find statistically significant overrepresented gene ontology (GO) terms, the Database for Annotation, Visualization and Integrated Discovery (DAVID, david.abcc.ncifcrf.gov, version 6.7) was employed (Huang et al., Nat Protoc 4:44-57, 2009; Huang et al., Nucleic Acids Res 37:1-13, 2009) and Functional Annotation Charts were created with default settings.

Real-Time PCR

Total RNA was extracted using TRizol® (Invitrogen) and then purified by RNeasy® Mini Kit (Qiagen. Valencia, Calif.). The concentrations of all RNA samples were determined by spectrophotometry. Equal amount of total RNA were used for reverse transcription and PCR, which was carried out on a thermocycler gradient (Eppendorf, Westbury, N.Y.) by using $RT^2$ First Strand Kit (SuperArray, Frederick, Md.) following standard protocols. Primers were designed by using Real-time PCR (TaqMan). Primer Design online tools available at genscript.com/ssl-bin/app/primer. Primer sequences are provided in Table 2. Real-time PCR was performed on MASTERCYCLER® ep realplex (Eppendorf). All reactions were performed in 96-well plates with the following reagents in a final volume of 25 μl:1 μl of primers (5 μM each for forward and reverse) and 2× MAXIMA® SYBR Green qPCR Master Mix from Fermentas (Glen Burnie, Md.). 10 ng of cDNA was added to this mixture. Triplicate reactions of the target and housekeeping genes were performed simultaneously for each cDNA template analyzed. The PCR reaction consisted of an initial enzyme activation step at 95° C. for 10 minutes, followed by 40 cycles of 95° C. for 15 seconds and 60° C. for one minute. A cycle threshold value (Ct) value was obtained for each sample and triplicate sample values were averaged. The 2-ΔΔCt method was used to calculate relative expression of each target gene. Data were analyzed using Student's t-test. Results were considered to be statistically significant when $p<0.05$ (two-sided). Real-time PCR products were also verified by running on 1.5% agarose gel, stained in 1×TAE with added GelStar® (Lonza, Basel, Switzerland) then visualized under UV transilluminator.

TABLE 2

Real-time PCR Primers

| Protein Name | Forward Primer | Reverse Primer |
|---|---|---|
| Importin subunit alpha-2 | TCAATGTGGAGCTGAGGAAAG (SEQ ID NO: 15) | CAACAGACCAATTTACAGTGCC (SEQ ID NO: 16) |
| Thymidylate synthase | CCCTCTGCCAGTTCTATGTG (SEQ ID NO: 17) | GTAGCTGGCGATGTTGAAAG (SEQ ID NO: 18) |
| 4F2 cell-surface antigen heavy chain | CTGGGCCTGGACTCTTC (SEQ ID NO: 19) | CACATCCCAAAGTTAAGCAC (SEQ ID NO: 20) |
| Thiosulfate sulfurtransferase/ rhodanese-like domain-containing protein 1 | TTCTGTCAGATGGGCAAGC (SEQ ID NO: 21) | CCAACCATTCTCTATAGGCTCC (SEQ ID NO: 22) |
| NAD(P) transhydrogenase, mitochondrial | TTGAAACCACTAAGCCAGGAG (SEQ ID NO: 23) | TGTTGGAATATAGGGTGCTGG (SEQ ID NO: 24) |
| Erythrocyte band 7 integral membrane protein | CGTGGATGGTGTGGTCTATTAC (SEQ ID NO: 25) | CCCAGAACATTCCTCAGAGTAG (SEQ ID NO: 26) |
| NADH dehydrogenase [ubiquinone] 1 beta subcomplex subunit 8, mitochondrial | GACAGCCTCCCACATGAC (SEQ ID NO: 27) | GTAGTCGCCATACCCCATG (SEQ ID NO: 28) |
| Histone H2A.Z | GGTAAGGCTGGAAAGGACTC (SEQ ID NO: 29) | TTAGGTGTCGATGAATACGGC (SEQ ID NO: 30) |
| Protein S100-A4 | GAAAAGGACAGATGAAGCTGC (SEQ ID NO: 31) | GACACAGTACTCTTGGAAGTCC (SEQ ID NO: 32) |
| SAM domain and HD domain-containing protein 1 | TTGTGCTAGAGATAAGGAAGTTGG (SEQ ID NO: 33) | TGTGTTGATAAGCTCTACGGTG (SEQ ID NO: 34) |
| Histone H1x | AAGTACTCGATCAAGGCGC (SEQ ID NO: 35) | TGAGCTTGAAGGAACCGTTG (SEQ ID NO: 36) |
| PhoSbhoglucomutase-2 | AACAGGGAGACAAAGGTGAAG (SEQ ID NO: 37) | GAGGAACAAGGTCAAAGCC (SEQ ID NO: 38) |
| Histone H1.2 | GCGCTAAGAAAACACCGAAG (SEQ ID NO: 39) | CTTTTGGCAGCTTTCTTGGG (SEQ ID NO: 40) |
| Histone H2B | AAAGTGCAGAAGAAGGACGGCAAG (SEQ ID NO: 41) | TGACGAAGGAGTTCATGATGCCCA (SEQ ID NO: 42) |

TABLE 2-continued

Real-time PCR Primers

| Protein Name | Forward Primer | Reverse Primer |
|---|---|---|
| Histone H1.3 | CTGCCAAGAGTCCAGCTAAG (SEQ ID NO: 43) | CTTTGCCTTTGTAACCTTCGG (SEQ ID NO: 44) |
| Histone H4 | TGGTGTTCTGAAGGTGTTCC (SEQ ID NO: 45) | GTAAAGAGTGCGTCCCTGTC (SEQ ID NO: 46) |
| Protein S100-A9 | TTGCAAAATGTCGCAGCTG (SEQ ID NO: 47) | CCCCAGCTTCACAGAGTATTG (SEQ ID NO: 48) |
| Vinculin | TGAGCGAATCCCAACCATAAG (SEQ ID NO: 49) | AAATCCTGTCCACAGTGAAGGCCA (SEQ ID NO: 50) |
| Protein S100-A8 | AGAAATTGCTAGAGACCGAGTG (SEQ ID NO: 51) | ACGCCCATCTTTATCACCAG (SEQ ID NO: 52) |
| Histone RNA hairpin-binding protein | GCGAGCTTAATTGCGTAATCC (SEQ ID NO: 53) | CTGAAGATGCCTGTGGAAAAC (SEQ ID NO: 54) |

Beta-Gal Assay

The Thermo Scientific Mammalian β-Galactosidase Assay Kit was used according to the manufacturer's instructions. Luminescence was measured by TopCount NXT® Microplate Scintillation and Luminescence Counter (PerkinElmer, Waltham, Mass.).

Alu-PCR

Two-step, Alu-gag PCR assay was used to detect and quantify integrated HIV. After isolating total DNA from HIV-infected cells, the first PCR is performed with one primer that anneals to Alu, and the other that anneals to gag. The second PCR detects HIV-specific products by using primers to the R and U5 regions within the HIV long terminal repeat (LTR).

Chromatin Immunoprecipitation (ChIP)

ChIP assay was performed according to protocols supplied by Millipore EZ-ChIP® Kit. Anti-NFκB, SP1, pol II, HDAC1, and NFAT were used as the capture antibody. Normal rabbit IgG (Cell Signaling, Danvers, Mass.) was used as negative control. Anti-RNA Polymerase II included in this kit was used as positive control antibody.

Chromatin DNA Digestion Assay

EZ Nucleosomal DNA Prep Kit from Zymo Research was used to isolate nucleosome-associated DNA and perform digestion.

HIV, e.g., HIV-1, upon integration into the human genome, becomes a newly acquired genetic locus. In a minority of infected individuals, viral transcription from this locus is low to absent, even in activated CD4+ T lymphocytes that have the capacity to harbor productive infection. A transcriptionally quiescent HIV-1 genetic locus was associated with a distinct proteomic signature in these non-progressors and elite controllers.

Stable isotope labeling of amino acids in cell culture (SILAC) was used to compare the proteomes of peripheral blood mononuclear cells (PBMCs) isolated from individuals with chronic HIV-1 infection with PVL>10,000 RNA copies/mL (n=10) and <1000 RNA copies/mL (n=10). Mass spectrometry-based differential protein expression patterns, validated by traditional Western blot, were used to identify greater than 3000 proteins that are differentially expressed in individuals with PVL>10,000 RNA copies/mL. Three of these candidate proteins were reproducibly over-expressed and 16 were reproducibly under-expressed in progressors. Six of the 16 under-expressed proteins were histone proteins. The over-representation of histone proteins in this study was surprising, and the under-expression of histone proteins was traced to the under-expression of histone-related SLBP.

Using HIV-1-infected HeLa T4 and CEM cells, depletion of SLBP led to a 3-fold increase in HIV-1 DNA integration, as determined by Alu-PCR and a 4-fold increase in HIV-1 multiple-spliced/unspliced RNA, as quantified by RT-PCR. SLBP depletion also led to increased retention of known LTR-associated transcription factors such as Sp1 (4-fold), NFκB (2-fold), and p300 (6-fold), as determined by ChIP assays using TZM cells with a stably integrated LTR. SLBP depletion also led to a more open chromatin structure as identified by nuclease digestion assays.

In a minority of HIV-1 infected individuals, viral transcription is low to absent even in activated CD4+ T lymphocytes that have the capacity to harbor productive infection. A distinct proteomic signature was associated with a transcriptionally quiescent HIV-1 genetic locus. Twenty HIV-1 infected patients were used in this study (FIG. 1). Ten of the patients were "HIV controllers," while ten were "HIV progressors." HIV controllers, present in one out of about every 300 infected subjects, maintain long term control of the virus to undetectable or nearly undetectable levels (below 2000 RNA copies/mL of blood). "Elite controllers," with less than 50 RNA copies/mL, are at the limit of detection of currently available commercial assays. The lower viral loads in controllers translate to slower AIDS progression and is also associated with a lower rate of transmission.

Stable isotope labeling with amino acids in cell culture labeling protocol is outlined in FIG. 2. Briefly, PBMCs were isolated from each subject, and equal amounts of PBMCs from each patient were mixed together. PBMCs from controllers were grown in "light" media for six days, while PBMCs from progressors were grown in "heavy" media for six days. Cells were mixed in a 1:1 ratio from "light" and "heavy" media, and proteins were extracted, gel electrophoresis was performed, bands were excised, and digested in-gel. Mass spectrometry was performed and data was analyzed.

1st Set Experiment:

Mix 5 million cells from each controller patient (2, 5, 6, 8, and 10), total 25 million cells serve as controller group, culture in "light" medium for 6 days with PHA-IL2 added.

Mix 5 million cells from each progressor patient (1, 3, 4, 7, and 9), total 25 million cells serve as progressor group, culture in "heavy" (with both heavy Arg and Lys added) medium for 6 days with PHA-IL2 added.

Figure 3:
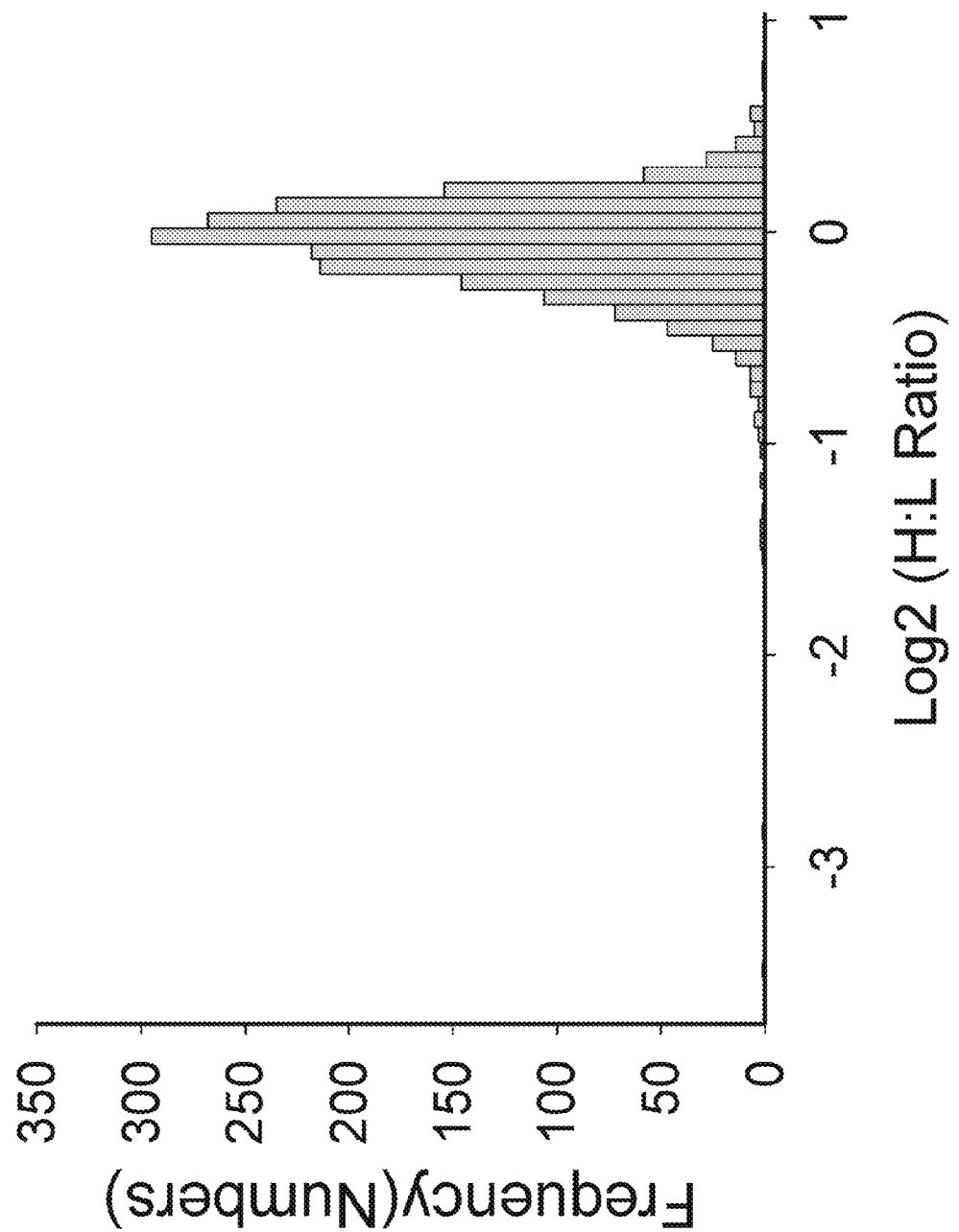
FIG. 3 is a bar graph showing the ratio distribution of first data set.

1:1 mix of cells from "light" and "heavy", follow procedures from above schematic map. A ratio distribution of 1st data set I shown in FIG. 3.

2nd Set Experiment:

Mix 5 million cells from each controller patient (15, 23, 24, 25, and 26), total 25 million cells serve as controller group, culture in "light" medium for 6 days with PHA-IL2 added.

Mix 5 million cells from each progressor patient (14, 18, 20-22), total 25 million cells serve as progressor group, culture in "heavy" (with both heavy Arg and Lys added) medium for 6 days with PHA-IL2 added.

Figure 4:
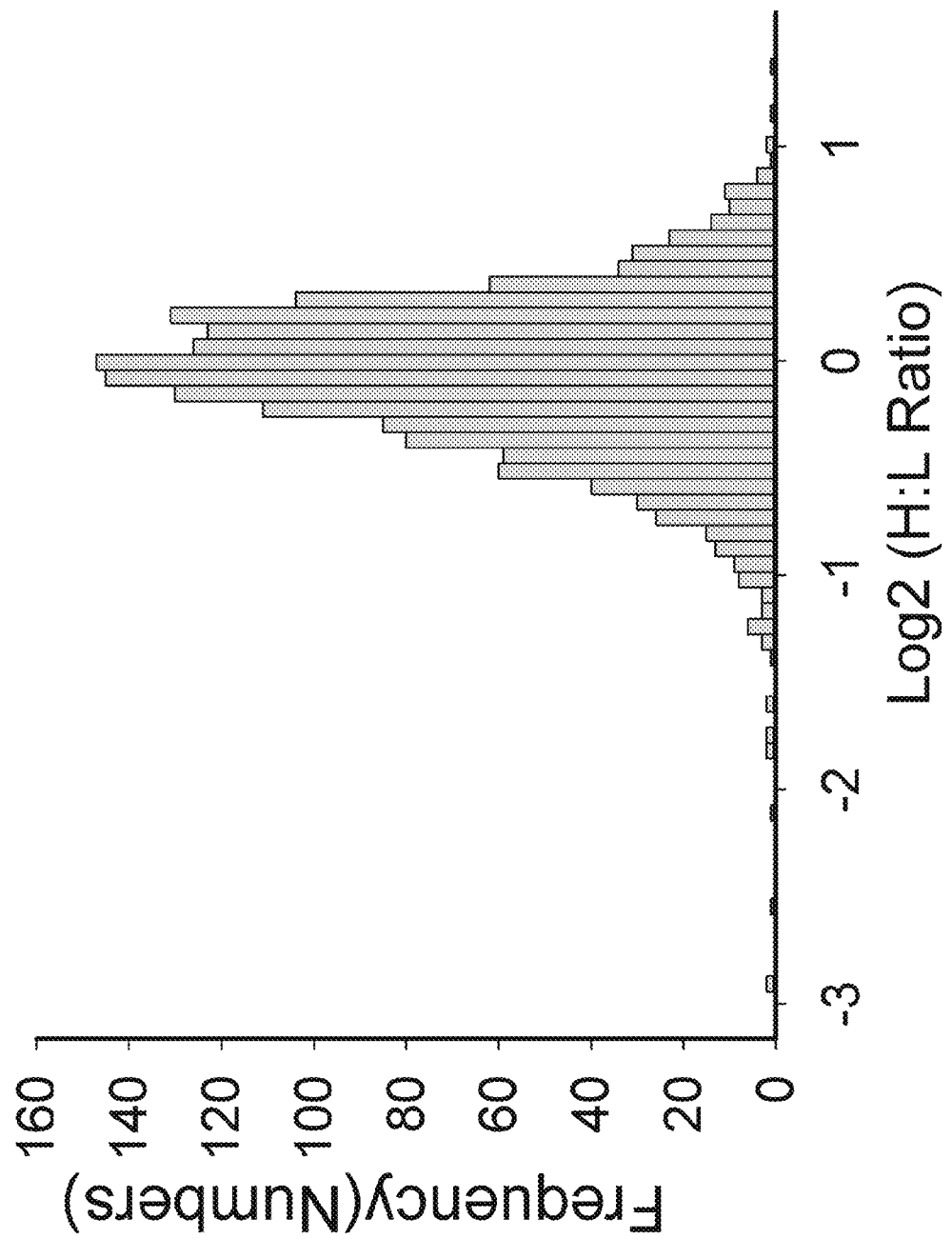
FIG. 4 is a bar graph depicting the ratio distribution of second data set.

1:1 mix of cells from "light" and "heavy", follow procedures front above schematic map. A ratio distribution of 1st data set I shown in FIG. 4.

More than 3000 proteins were identified, about 2000 proteins of which were quantified. After applying a few filters (e.g., manual inspection of peaks and ratios, removal of redundant identification), 19 candidates were chosen from the two different sets of SILAC patient samples (FIG. 5). Variation of SILAC ratios for 1st dataset is 18%, while for 2nd dataset is 22%, and a conservative value of 1±0.5 was selected.

Figure 6:
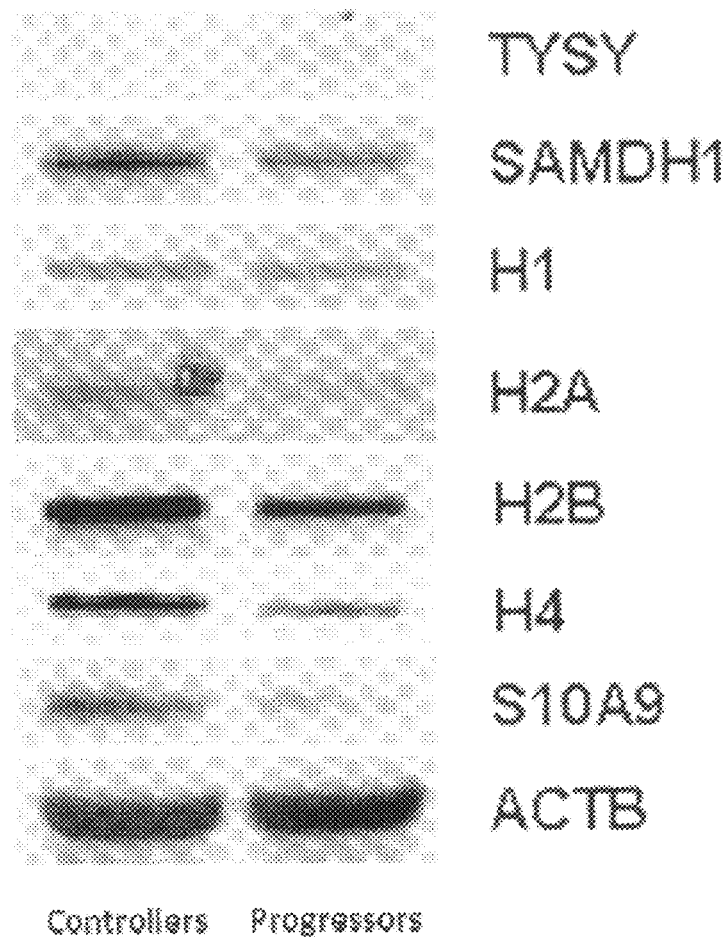
FIG. 6 is a set of photomicrographs of Western blots verifying some representative candidates from mass spectrometry data.
Figure 7:
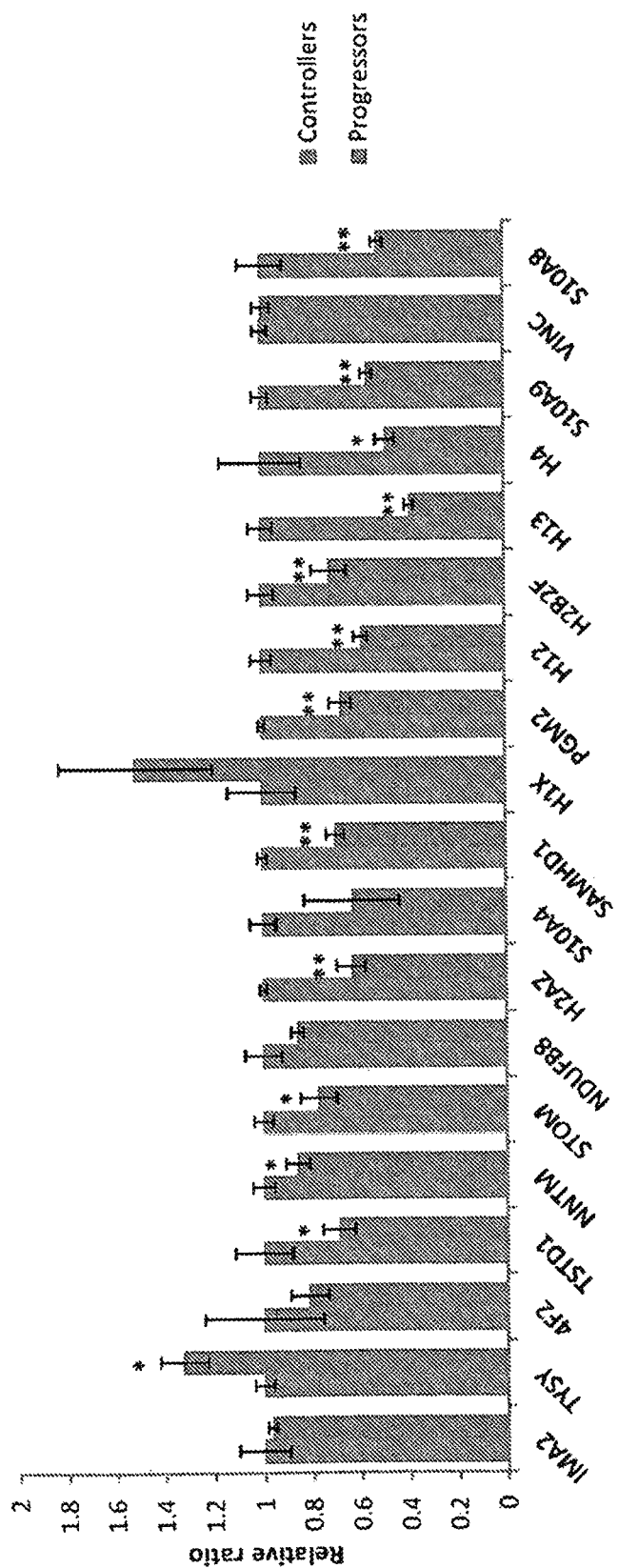
FIG. 7 is a bar graph showing that the RNA level expression of 13 (out of 19) candidates correlated with its protein level expression in patient samples.
Figure 8:
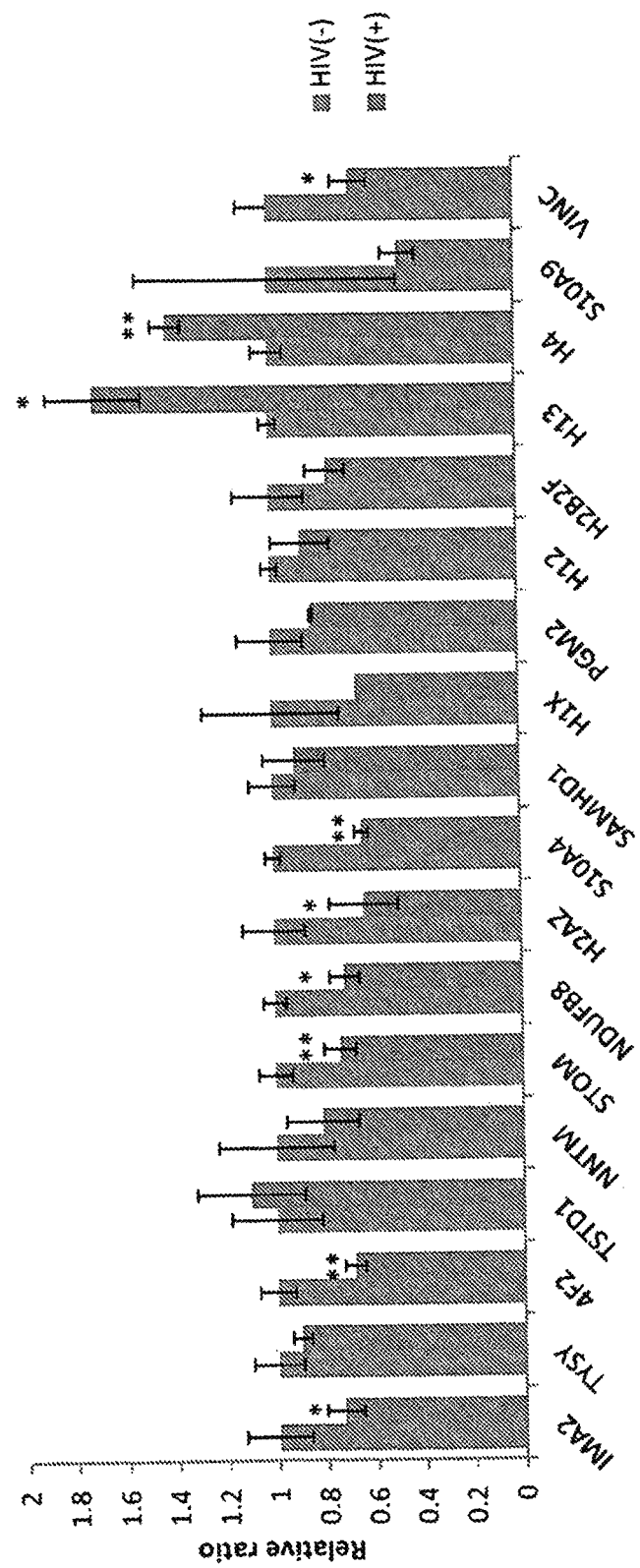
FIG. 8 is a bar graph depicting RNA expression profile of HIV-1 infection itself from H9 cells didn't correlated well with the profile from patient samples.
Figure 9:
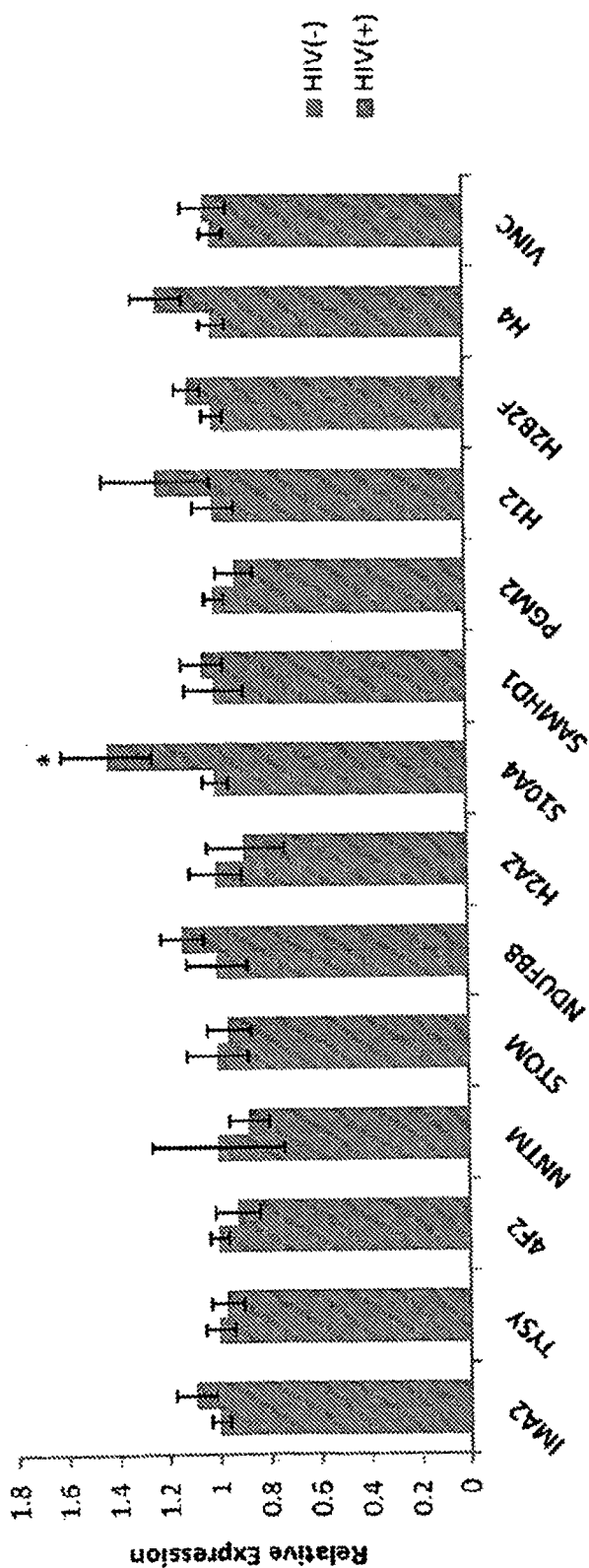
FIG. 9 is a bar graph showing RNA expression profile of HIV-1 infection itself from TZM-b1 cells has no correlation with the profile from patient samples.

Western blots were performed to verify some representative candidates from mass spectrometry (FIG. 6). The RNA level expression of 13 (out of 19) candidates correlated with its protein level expression in patient samples (FIG. 7). Compared to overall down-regulated profiles in progressors/controllers, HIV-1 infection itself had variable effect on the RNA expression of the 19 candidate in H9 cells, suggesting an existence of unique molecular responses of controllers (FIG. 8). Compared to overall down-regulated profiles in progressors/controllers, HIV-1 infection itself had no effect on the RNA expression of the 19 candidate in TZM-bl cells (FIG. 9). Accordingly. TZM-bl was selected as an ideal cell line for studying the functions of those 19 candidates.

Figure 10:
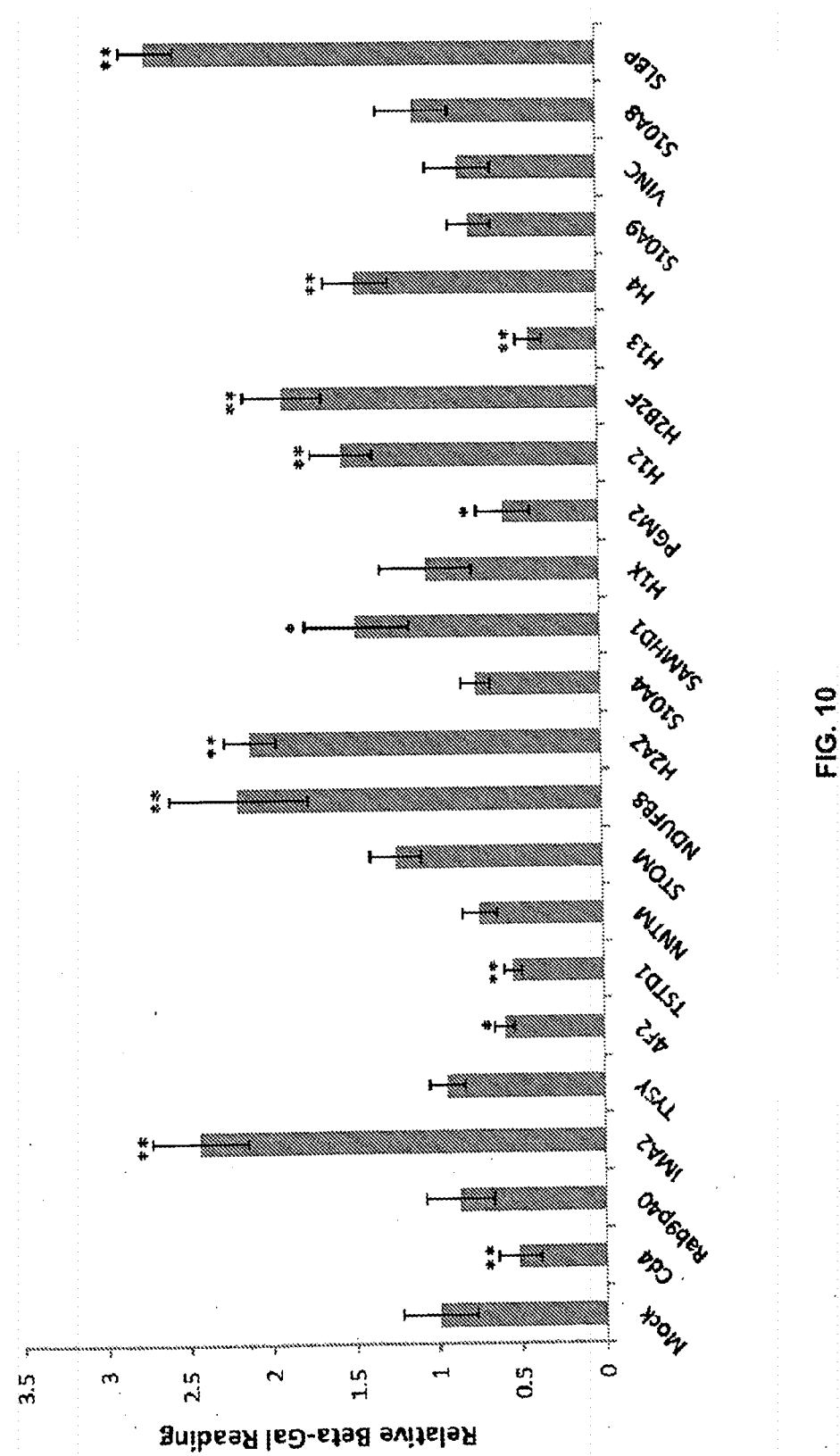
FIG. 10 is a bar graph depicting beta-gal readings of each candidate on HIV-1 biogenesis, primarily for integration and transcription stages.
Figure 11:
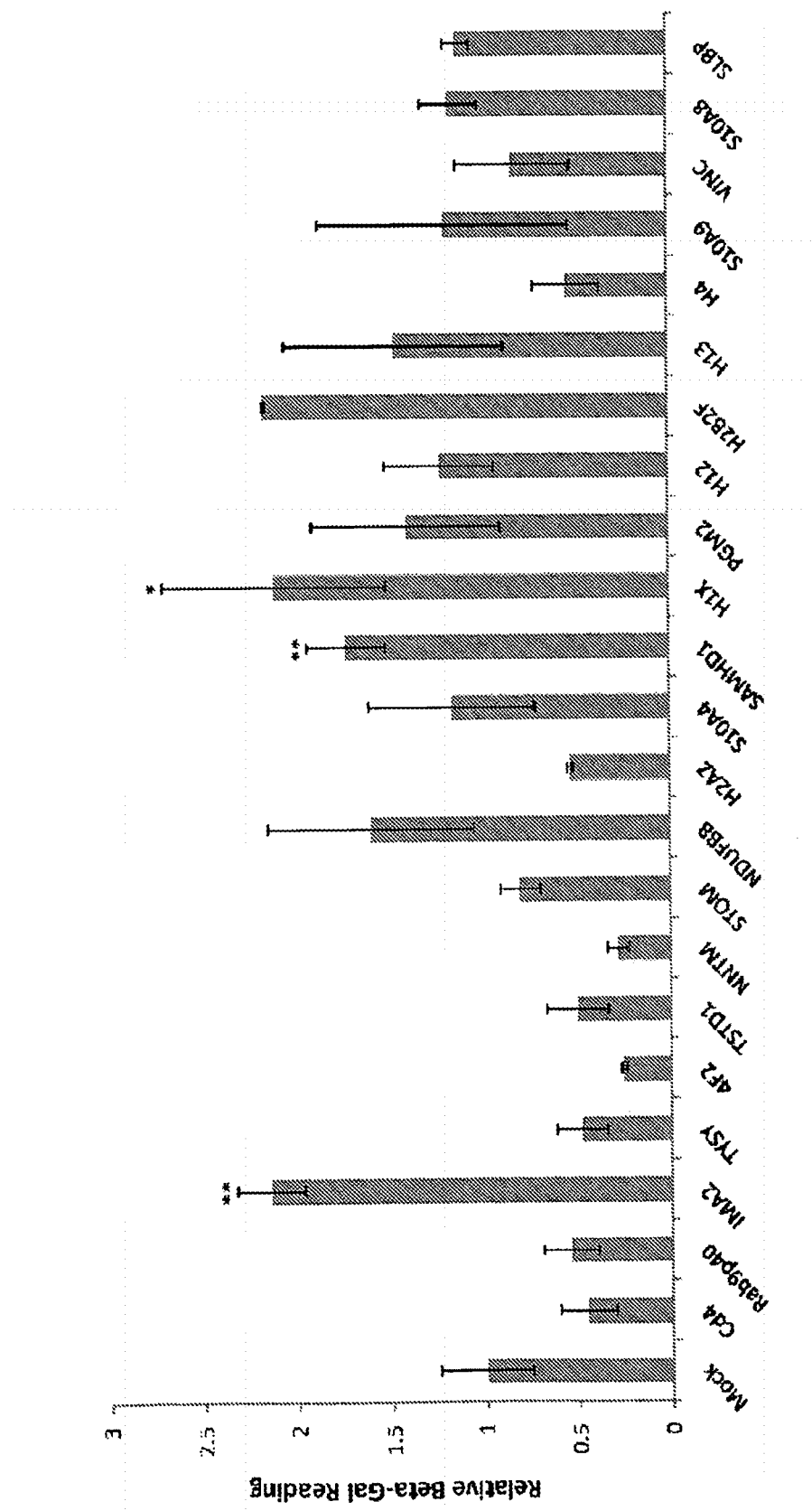
FIG. 11 is a bar graph showing beta-gal readings of each candidate for HIV-1 infectiousness.

Beta-gal readings of each candidate on HIV-1 biogenesis, primarily for integration and transcription stages. TZM-bl cells were transfected with siRNAs against each of 19 candidates respectively for 48 hours followed by HIV-1 infection for 24 hours (FIG. 10). Beta-gal readings of each candidate for HIV-1 infectiousness. Supernatants from above TZM-bl cells (transfected with siRNAs for 48 hours followed by HIV-1 infection for 24 hours) were transferred to freshly prepared TZM-bl cells and cultured for 48 hours (FIG. 11). These results demonstrate that many of candidates potentially affect HIV integration and transcription, but not infectiousness while differential expression of histones plays a role in HIV-1 biogenesis.

Figure 12:
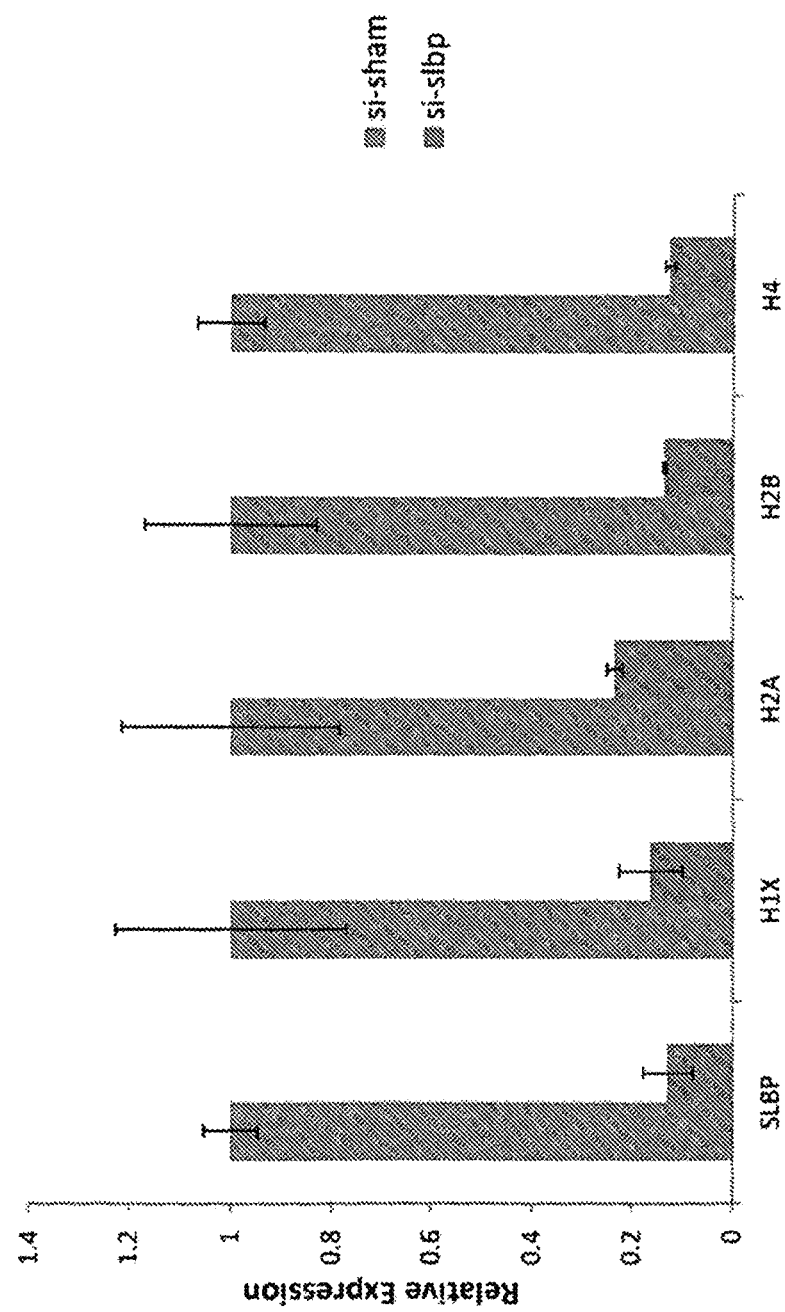
FIG. 12 is a bar graph depicting the relationship between SLBP and histones at the RNA level.
Figure 13:
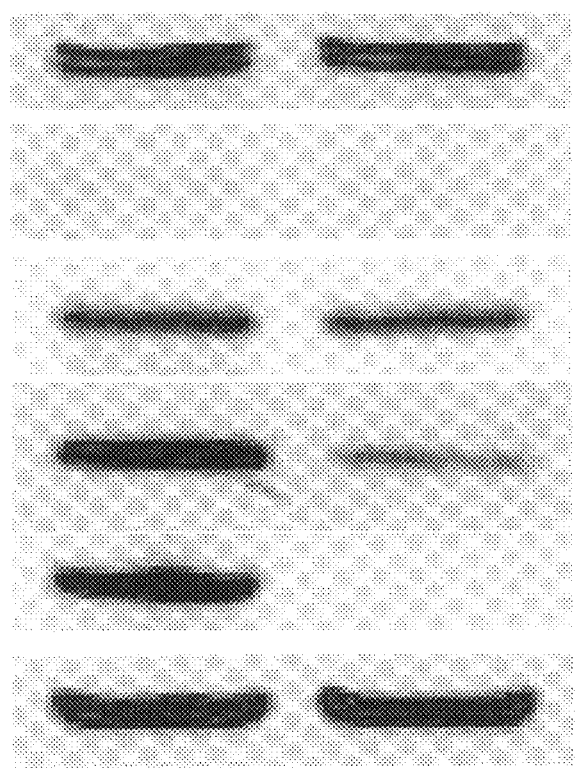
FIG. 13 is a set of photomicrographs showing the relationship between SLBP and histones at the protein level.
Figure 14:
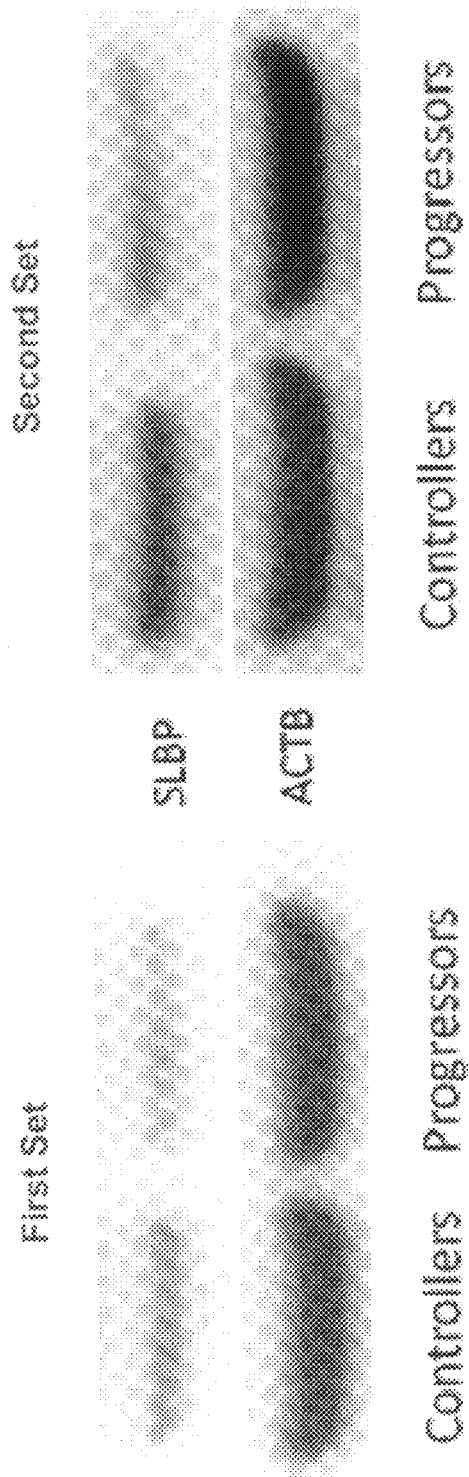
FIG. 14 is a set of photomicrographs depicting SLBP expression level in progressors/controllers at the protein level.
Figure 15:
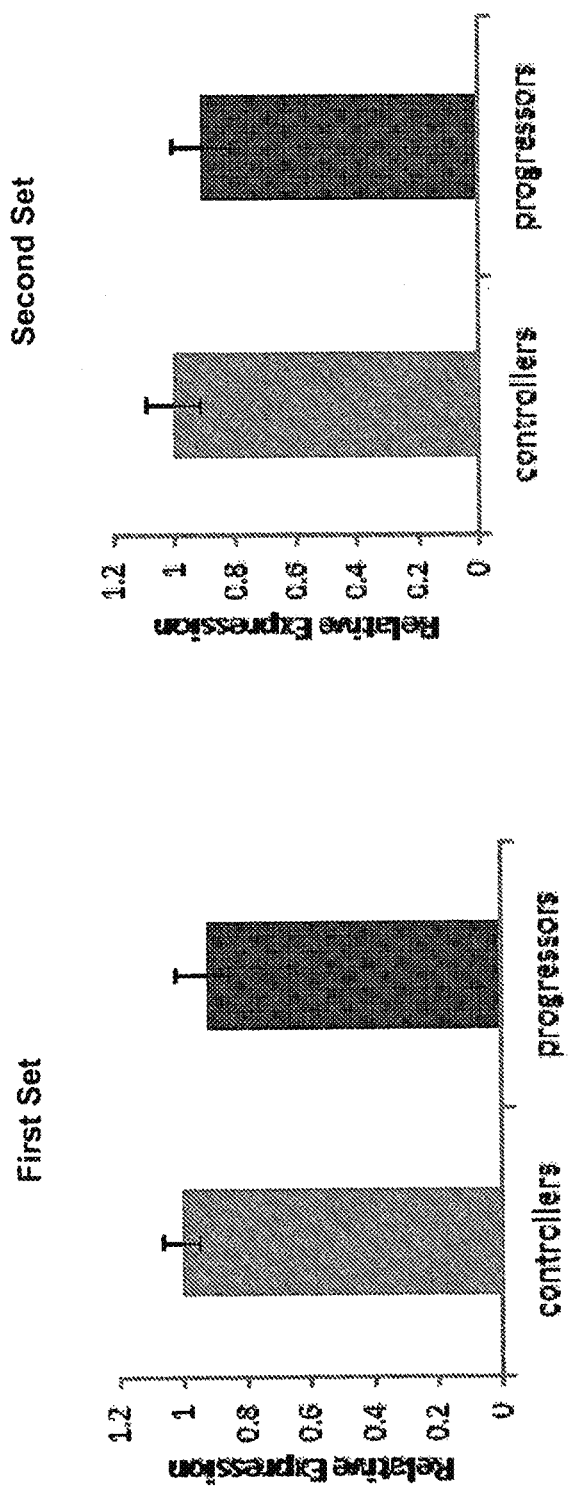
FIG. 15 is a bar graph showing SLBP expression level in progressors/controllers at the RNA level.

SLBP, a master regulator of histones, was shown to regulate histones (FIGS. 12 and 13). At an RNA level, decreased SLBP resulted lower level of histones (FIG. 12). At a protein level, only H4 and to less extent, H2A correlated with SLBP levels (FIG. 13). SLBP was expressed at lower levels in progressors than controllers at both an RNA and protein level (FIGS. 14 and 15).

Figure 16:
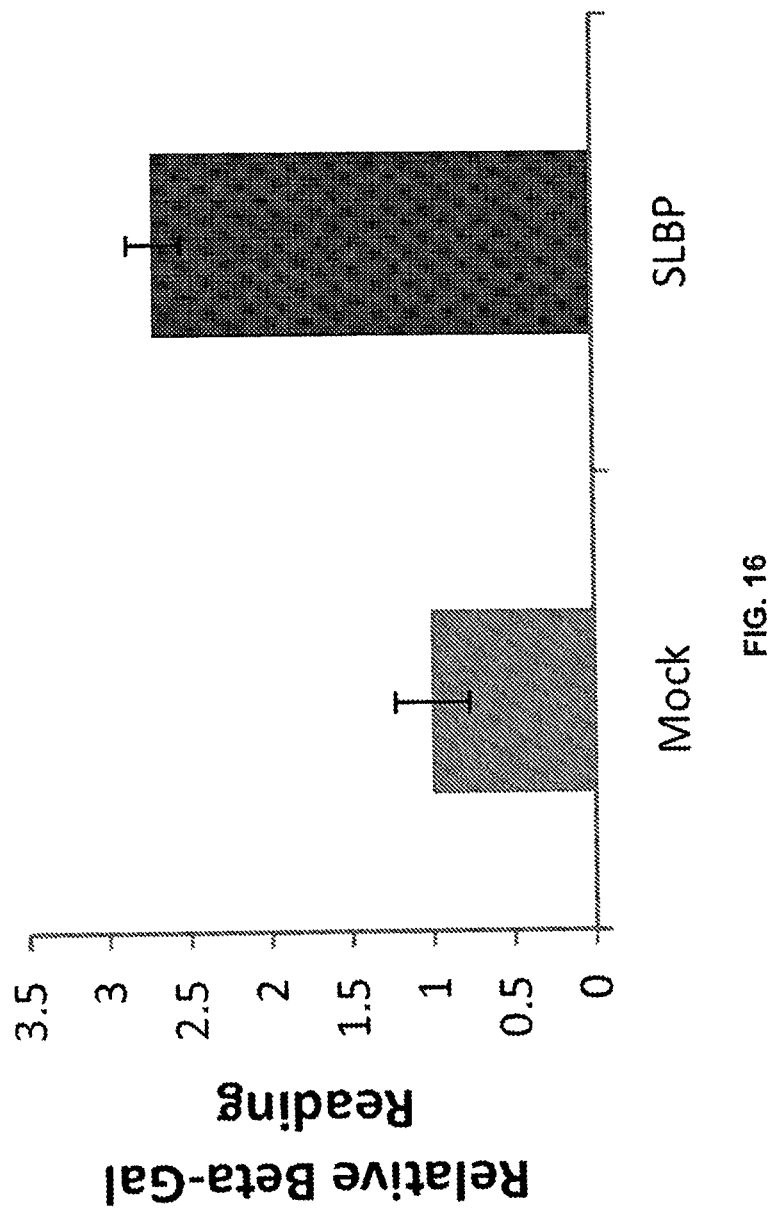
FIG. 16 is a bar graph depicting beta-gal readings when SLBP was knocked down by siRNA, at the integration and transcription stages.
Figure 17:
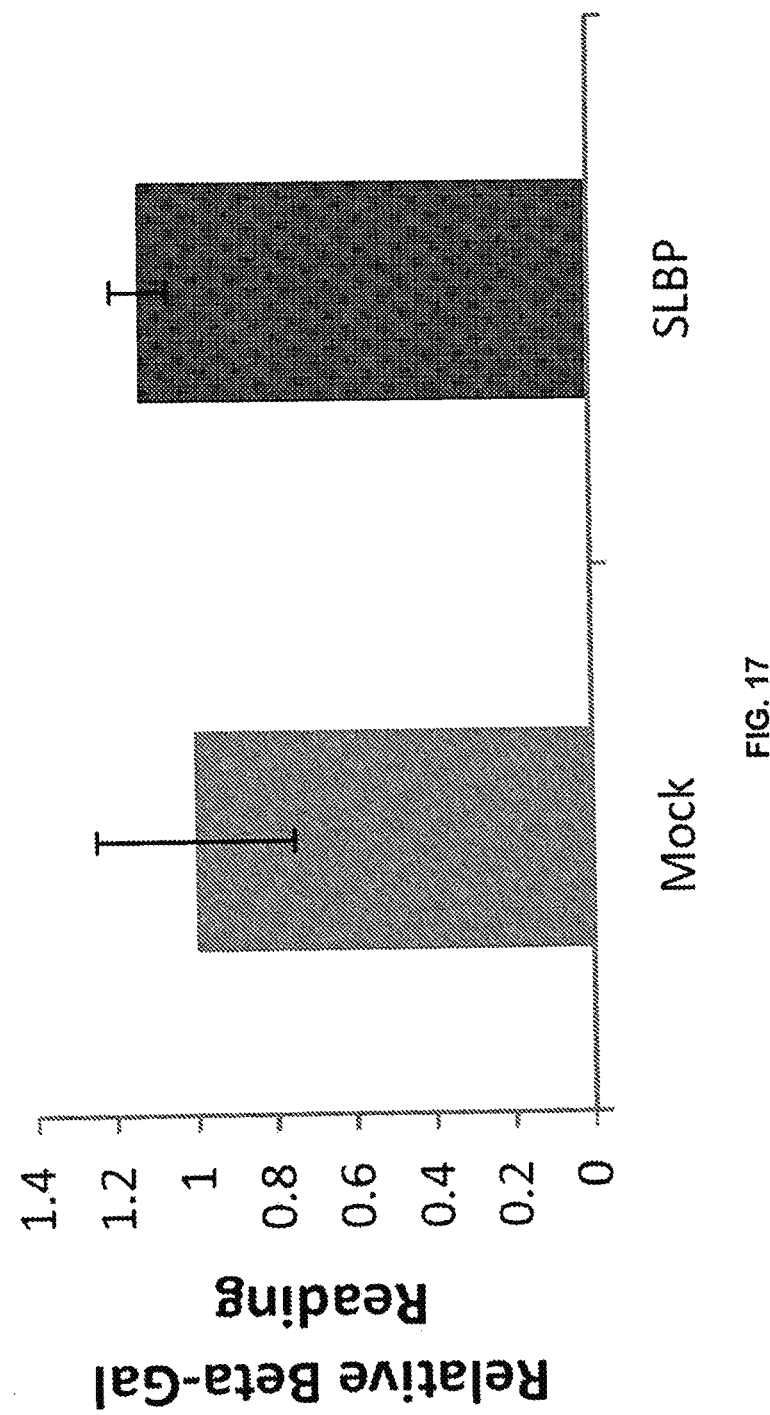
FIG. 17 is a bar graph showing beta-gal readings when SLBP was knocked down by siRNA, at the infectious stage.
Figure 19A:
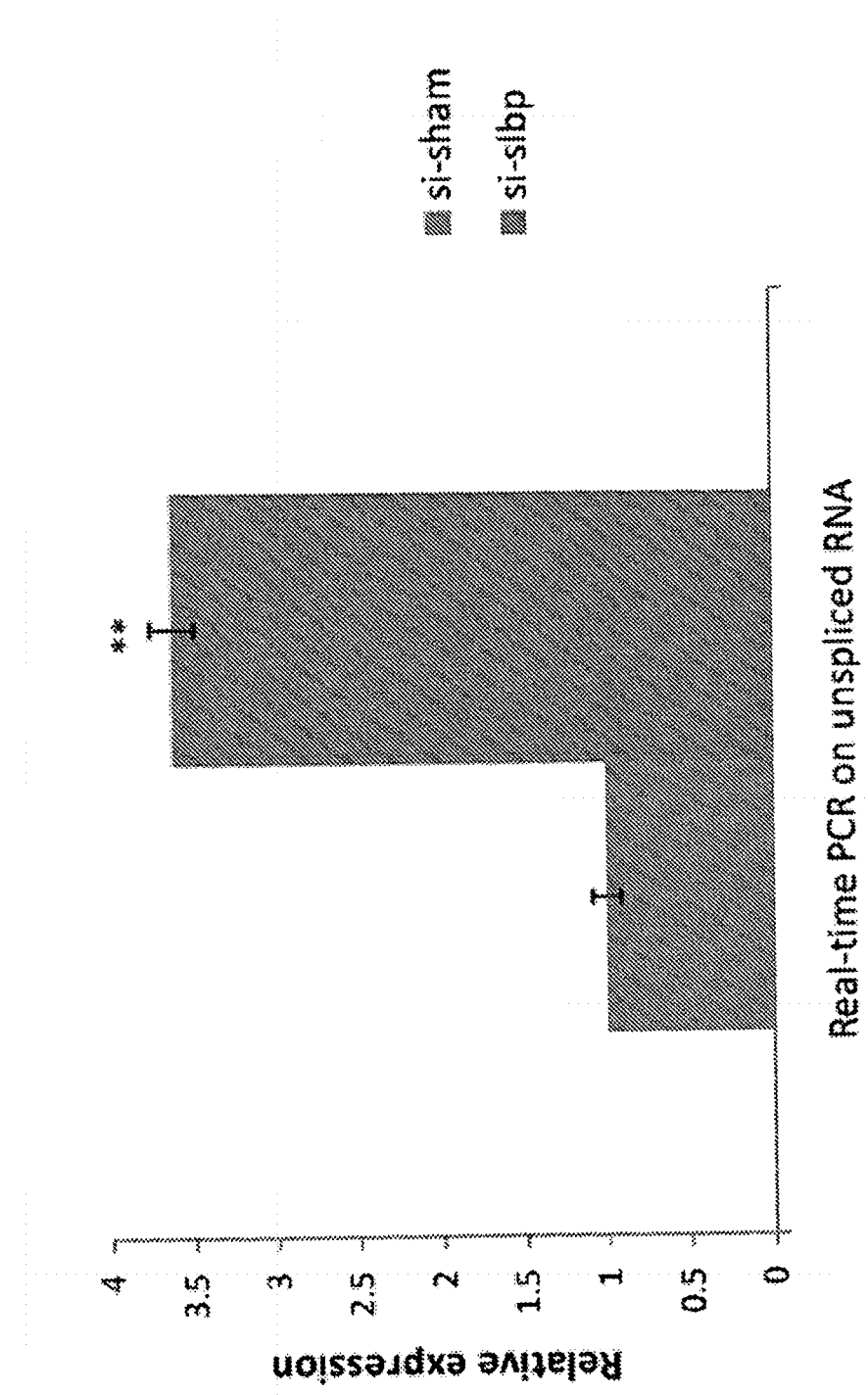
FIGS. 19A and 19B are a set of bar graphs showing that under-expressed SLBP led to increased production of HIV-1 unspliced/multiple spliced RNA.
Figure 19B:
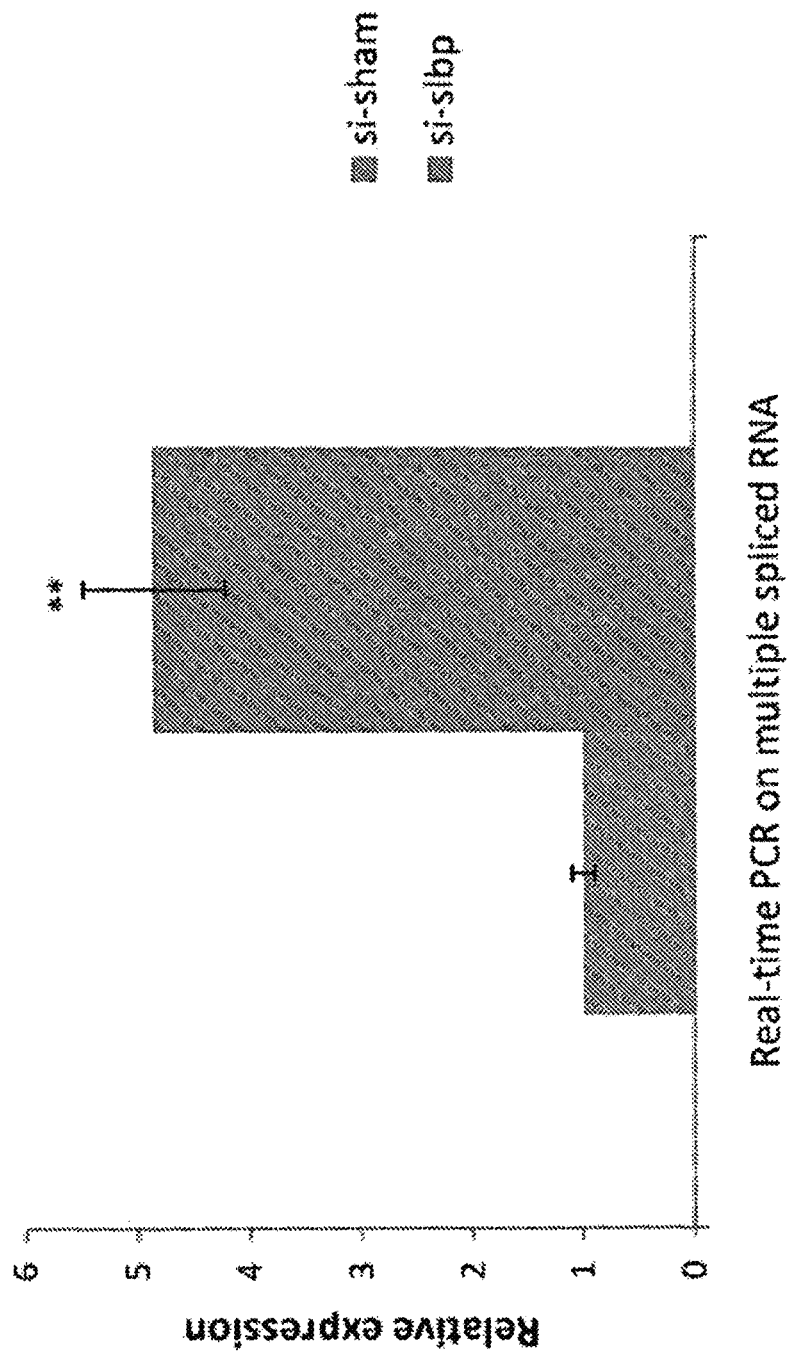

Beta-gal reading when SLBP was knocked down by siRNA. Check the roles at integration and transcription stages. SLBP likely impacts HIV-1 biogenesis (FIG. 16), but does not appear to influence HIV-1 infectiousness (FIG. 17). Lower levels of SLBP facilitate HIV-1 integration as chromatin structures are looser (FIG. 18). Under-expressed SLBP led to increased production of HIV-1 unspliced/multiple spliced RNA (FIGS. 19A and 19B).

Figure 20:
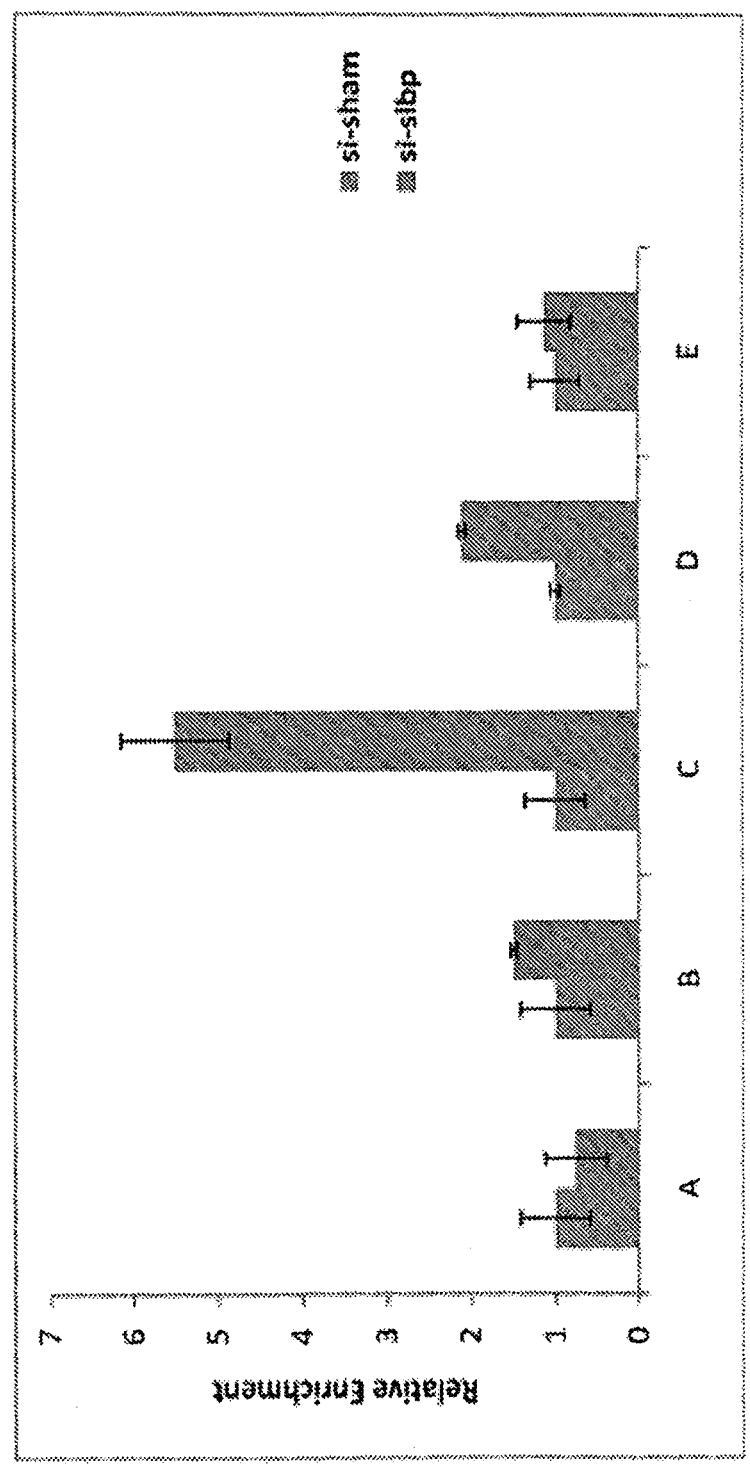
FIG. 20 is a bar graph depicting that SLBP depletion led to increased retention of NFκB.
Figure 21:
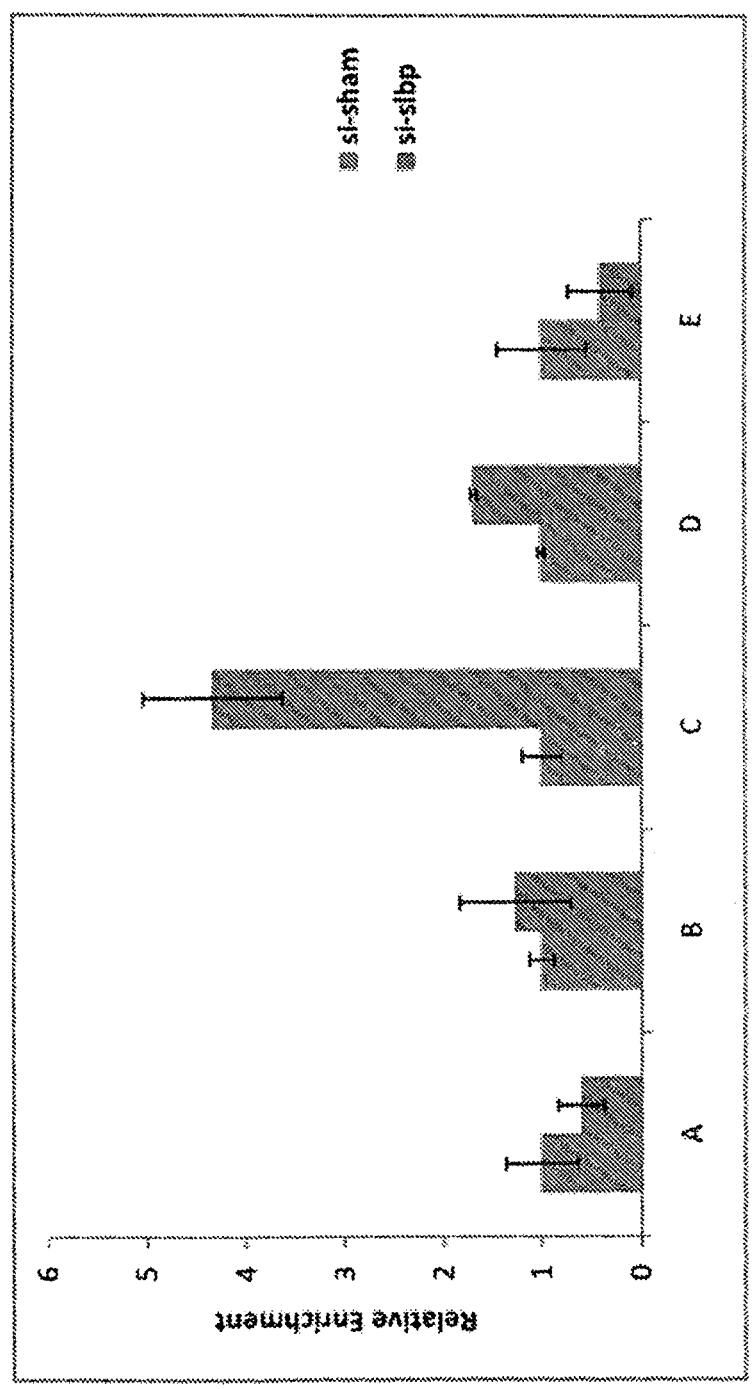
FIG. 21 is a bar graph showing that SLBP depletion led to increased retention of Sp1.
Figure 22:
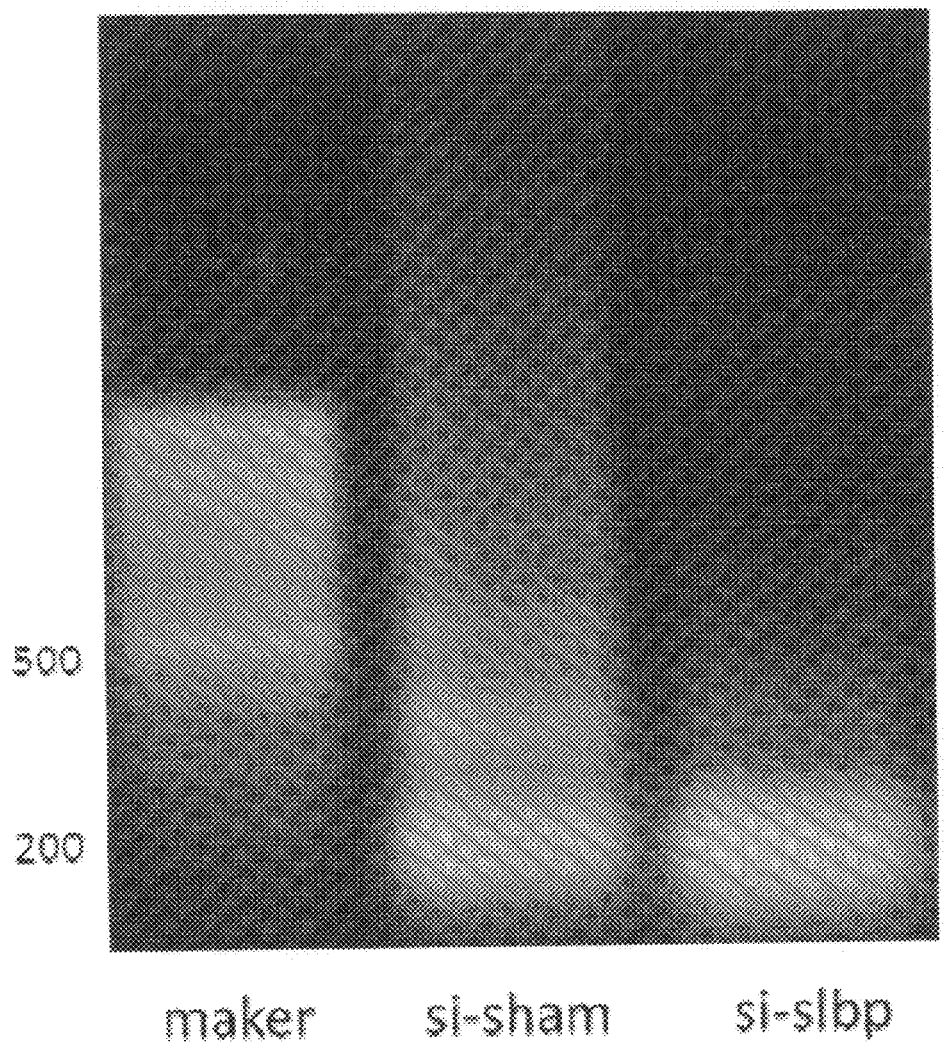
FIG. 22 is a photomicrograph showing nuclease digestion of chromatin.

ChIP assay on HIV-1 LTR when SLBP was knockdown for NFκB (5-fold; FIG. 20) and Sp1 (4-fold; FIG. 21). SLBP depletion also led to a more open chromatin structure (FIG. 22). Chromatin was readily digested by nuclease in experiments with siRNA.

Figure 23A:
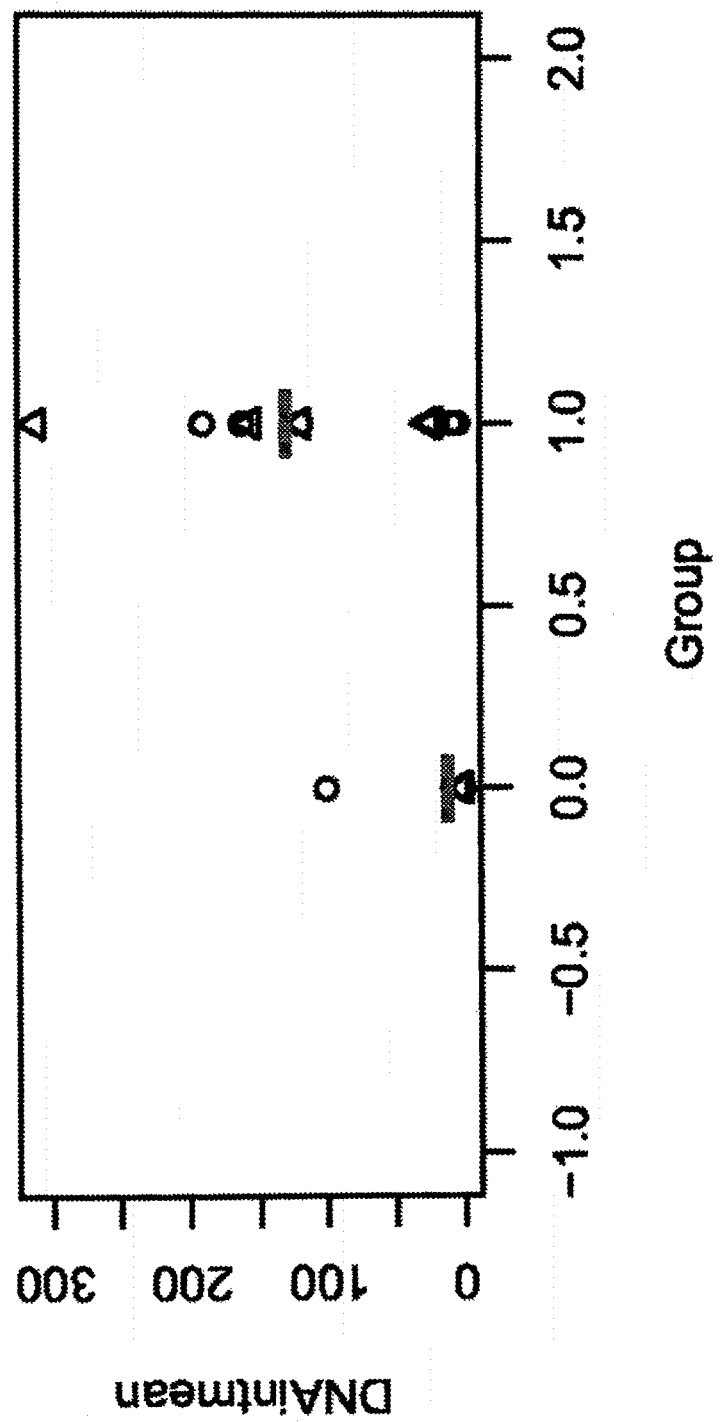
FIG. 23A is a scatter plot showing HIV-1 integration level in individual patients.
Figure 23B:
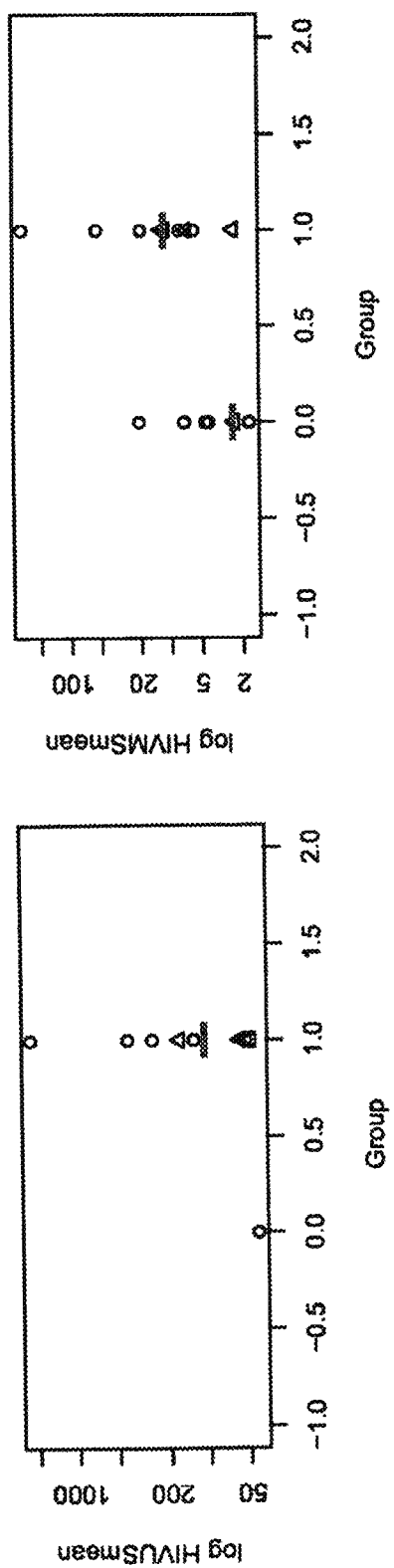
FIG. 23B is a set of two scatter plots depicting HIV-1 unspliced/multiple spliced RNA in individual patients.
Figure 23C:
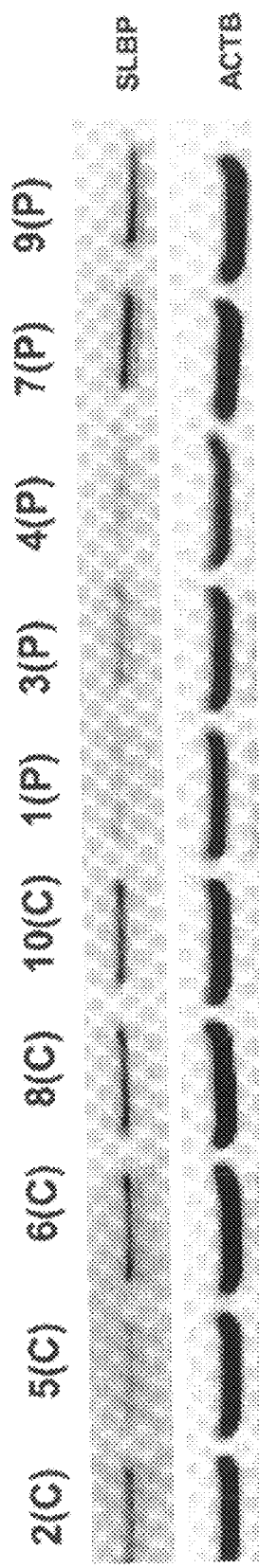
FIG. 23C is a photomicrograph showing protein levels of SLBP in individual patients.

SLBP level in individual patients was studied and HIV-1 integration level (FIG. 23A), ms/us RNA level (FIG. 23B), and protein levels (FIG. 23C) were examined.

Example 2

CD4 Cells Isolation

By following manufacturer's instructions, DYNABEADS® CD4 Positive Isolation Kit (Life Technologies) was used to isolate CD4+ cells from clinical controllers and progressors. CD4+ purity (99.2%) was confirmed by cell cytometry.

Western Blotting

CD4 cellular protein was harvested, quantified by micro BCA assay and run on NuPAGE® 4-12% Bis-Tris precast Gel (Invitrogen) by using XCell SureLock® Mini-Cell (Life Technologies). After electrophoresis, the resolved proteins were transferred onto PVDF membrane by using XCell II® Blot Module. Upon the completion of transfer, membranes were blocked for one hour before adding anti-ACTB (1/10000 dilution, BD Biosciences, San Diego, Calif.), anti-SLBP (1/2000 dilution, Sigma) and incubating overnight at 4° C. Finally, proteins were detected and analyzed by Odyssey® CLx Infrared Imaging System (LI-COR, Lincoln, Nebr.) after incubation with IRDye® 680LT or 800CW conjugated secondary antibodies for 30 minutes followed by four PBST washes.

Figure 24:
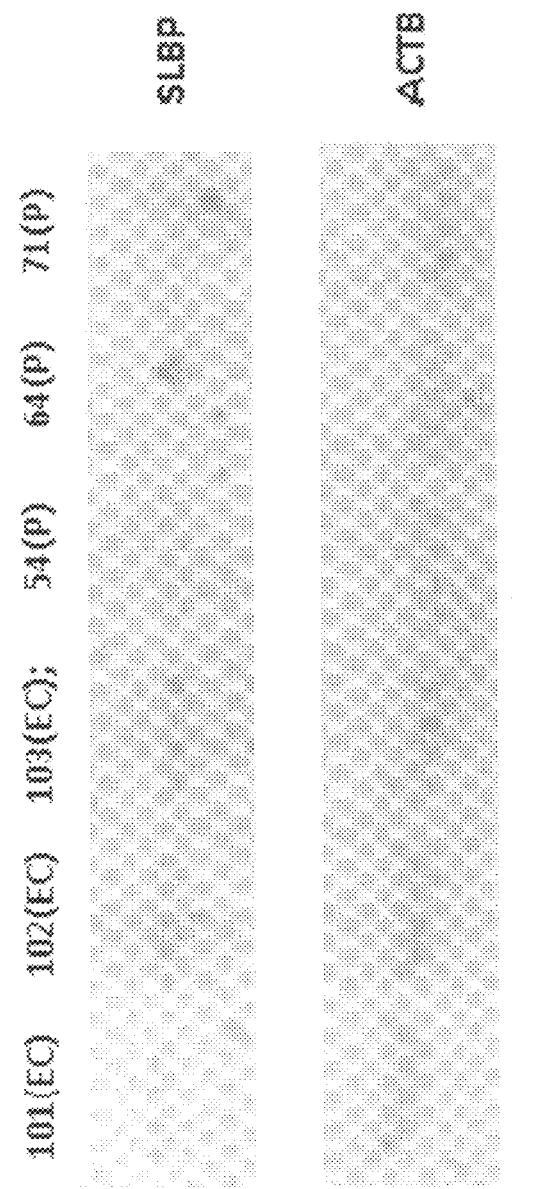
FIG. 24 is a photomicrograph of a Western blot showing SLBP levels in Elite Controllers (101, 102, and 103) and in HIV progressors (54, 64, and 71).

Given that HIV-1 infection is restricted to CD4+ T cells and monocytes, SLBP levels were profiled in highly purified CD4+ T lymphocytes. As shown in FIG. 24, SLBP levels were uniformly increased in CD4+ T lymphocytes isolated from individuals with autonomous control of virus (viral load less than 50 copies/ml-denoted as "EC" for "Elite Controller") compared to individuals with high viral load ("P" for "HIV progressors").

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating AIDS in a subject or reducing a risk of developing AIDS in a HIV-infected subject, the method comprising administering to the subject a therapeutically effective amount of step loop binding protein (SLBP), thereby treating AIDS in the subject, or reducing the risk of developing AIDS in the HIV-infected subject.

2. The method of claim 1, the method further comprising selecting the subject for administration of a therapeutically effective amount of SLBP, wherein selecting the subject comprises:
   providing a sample from the subject;
   assaying the sample to determine a level of SLBP in the sample to obtain a test value;
   comparing the test value to a reference value; and
   selecting the subject if the test value is less than or about the same as the reference value.

3. The method of claim 1, wherein the SLBP is administered to the patient intraperitoneally, intramuscluarly, by infusion, vaginally, rectally, or orally.

4. The method of claim 1, the method further comprising treating the subject with an anti-retroviral therapy.

5. The method of claim 4, wherein the anti-retroviral therapy is selected from the group consisting of an entry inhibitor, a CCR5 receptor antagonist, a reverse-transcriptase inhibitor, a protease inhibitor, an integrase inhibitor, and a maturation inhibitor.

6. The method of claim 2, wherein the sample comprises serum, plasma, or blood.

* * * * *

UNITED STATES PATENT AND TRADEMARK OFFICE
CERTIFICATE OF CORRECTION

| | | |
|---|---|---|
| PATENT NO. | : 9,522,943 B2 | Page 1 of 1 |
| APPLICATION NO. | : 14/378715 | |
| DATED | : December 20, 2016 | |
| INVENTOR(S) | : Michelle Lally, Bharat Ramratnam and Ming Li | |

It is certified that error appears in the above-identified patent and that said Letters Patent is hereby corrected as shown below:

On the Title Page

Column 2 (Other Publications), Line 20, delete "etla.," and insert -- et al., --;

In the Claims

In Column 66, Line 52 (approx.), in Claim 3, delete "intramusclularly," and insert -- intramuscularly, --.

Signed and Sealed this
Fourteenth Day of March, 2017

Michelle K. Lee
*Director of the United States Patent and Trademark Office*

SEQUENCE LISTING

<160> NUMBER OF SEQ ID NOS: 54

<210> SEQ ID NO 1
<211> LENGTH: 813
<212> TYPE: DNA
<213> ORGANISM: Homo sapiens
<220> FEATURE:
<223> OTHER INFORMATION: stem loop binding protein

<400> SEQUENCE: 1

| | | |
|---|---|---|
| atggcctgcc gcccgcgaag cccgccgagg catcagagcc gctgcgacgg tgacgccagc | 60 |
| ccgccgtccc ccgcgcgatg gagcctggga cggaagcgca gagccgacgg caggcgctgg | 120 |
| aggcccgaag acgccgagga ggcagagcac cgcggcgccg agcgcagacc cgagagcttt | 180 |
| accactcctg aaggccctaa accccgttcc agatgctctg actgggcaag tgcagttgaa | 240 |
| gaagatgaaa tgaggaccag agttaacaaa gaaatggcaa gatataaaag gaaactcctc | 300 |
| atcaatgact ttggaagaga gagaaaatca tcatcaggaa gttctgattc aaaggagtct | 360 |
| atgtctactg tgccggctga ctttgagaca gatgaaagtg tcctaatgag gagacagaag | 420 |
| cagatcaact atgggaagaa cacaattgcc tacgatcgtt atattaaaga agtcccaaga | 480 |
| caccttcgac aacctggcat tcatcccaag accccta ata aatttaagaa gtatagtcga | 540 |
| cgttcatggg accagcaaat caaactctgg aaggtggctc tgcatttttg ggatcctcca | 600 |
| gcggaagaag gatgtgattt gcaagaaata caccctgtag accttgaatc tgcagaaagc | 660 |
| agctccgagc cccagaccag ctctcaggat gactttgatg tgtactctgg cacacccacc | 720 |
| aaggtgagac acatggacag tcaagtggag gatgagtttg atttggaagc ttgtttaact | 780 |
| gaacccttga gagacttctc agccatgagc taa | 813 |

<210> SEQ ID NO 2
<211> LENGTH: 270
<212> TYPE: PRT
<213> ORGANISM: Homo sapiens
<220> FEATURE:
<223> OTHER INFORMATION: stem loop binding protein

<400> SEQUENCE: 2

Met Ala Cys Arg Pro Arg Ser Pro Pro Arg His Gln Ser Arg Cys Asp
 1               5                   10                  15

Gly Asp Ala Ser Pro Pro Ser Pro Ala Arg Trp Ser Leu Gly Arg Lys
            20                  25                  30

Arg Arg Ala Asp Gly Arg Arg Trp Arg Pro Glu Asp Ala Glu Glu Ala
        35                  40                  45

Glu His Arg Gly Ala Glu Arg Arg Pro Glu Ser Phe Thr Thr Pro Glu
    50                  55                  60

Gly Pro Lys Pro Arg Ser Arg Cys Ser Asp Trp Ala Ser Ala Val Glu
65                  70                  75                  80

Glu Asp Glu Met Arg Thr Arg Val Asn Lys Glu Met Ala Arg Tyr Lys
                85                  90                  95

Arg Lys Leu Leu Ile Asn Asp Phe Gly Arg Glu Arg Lys Ser Ser Ser
            100                 105                 110

Gly Ser Ser Asp Ser Lys Glu Ser Met Ser Thr Val Pro Ala Asp Phe
        115                 120                 125

Glu Thr Asp Glu Ser Val Leu Met Arg Arg Gln Lys Gln Ile Asn Tyr
    130                 135                 140

Gly Lys Asn Thr Ile Ala Tyr Asp Arg Tyr Ile Lys Glu Val Pro Arg
145                 150                 155                 160

```
His Leu Arg Gln Pro Gly Ile His Pro Lys Thr Pro Asn Lys Phe Lys
                165                 170                 175

Lys Tyr Ser Arg Arg Ser Trp Asp Gln Gln Ile Lys Leu Trp Lys Val
            180                 185                 190

Ala Leu His Phe Trp Asp Pro Pro Ala Glu Glu Gly Cys Asp Leu Gln
        195                 200                 205

Glu Ile His Pro Val Asp Leu Glu Ser Ala Glu Ser Ser Ser Glu Pro
    210                 215                 220

Gln Thr Ser Ser Gln Asp Asp Phe Asp Val Tyr Ser Gly Thr Pro Thr
225                 230                 235                 240

Lys Val Arg His Met Asp Ser Gln Val Glu Asp Glu Phe Asp Leu Glu
                245                 250                 255

Ala Cys Leu Thr Glu Pro Leu Arg Asp Phe Ser Ala Met Ser
            260                 265                 270
```

<210> SEQ ID NO 3
<211> LENGTH: 642
<212> TYPE: DNA
<213> ORGANISM: Homo sapiens
<220> FEATURE:
<223> OTHER INFORMATION: histone H1X

<400> SEQUENCE: 3

```
atgtccgtgg agctcgagga ggccctgcca gtgacgaccg ccgagggaat ggccaagaag    60
gtgaccaagg ctggcggctc ggcggcgttg tccccatcta agaagaggaa gaatagcaag   120
aagaagaacc agccgggcaa gtacagccag ctggtggtgg agaccatccg taggctgggc   180
gagcgcaacg gctcgtcgct ggccaagatc tacaccgagg ccaagaaggt tccgtggttc   240
gaccagcaga tgggcgcac  ctacctcaag tactcgatca aggcgctggt gcagaacgac   300
acgcttctgc aggtgaaggg caccggcgcc aacggttcct tcaagctcaa ccgcaagaag   360
ctggagggcg cggggagcg  cgcggagccc cggcggccg  ccaccgcccc ggcccccacc   420
gcgcacaaag cgaagaaggc agccccgggc gcggccggct cccggcgcgc ggacaagaag   480
cccgccaggg gccagaagcc ggagcagcgc tcgcacaaga agggcgctgg cgccaagaag   540
gacaaaggcg gcaaggccaa aagacggcg  gccgccgggg gcaagaaggt gaagaaggcg   600
gccaagccca gcgtccccaa agtgcccaag ggccgcaagt ga                      642
```

<210> SEQ ID NO 4
<211> LENGTH: 213
<212> TYPE: PRT
<213> ORGANISM: Homo sapiens
<220> FEATURE:
<223> OTHER INFORMATION: histone H1X

<400> SEQUENCE: 4

```
Met Ser Val Glu Leu Glu Glu Ala Leu Pro Val Thr Thr Ala Glu Gly
1               5                   10                  15

Met Ala Lys Lys Val Thr Lys Ala Gly Gly Ser Ala Ala Leu Ser Pro
            20                  25                  30

Ser Lys Lys Arg Lys Asn Ser Lys Lys Asn Gln Pro Gly Lys Tyr
            35                  40                  45

Ser Gln Leu Val Val Glu Thr Ile Arg Arg Leu Gly Glu Arg Asn Gly
        50                  55                  60

Ser Ser Leu Ala Lys Ile Tyr Thr Glu Ala Lys Lys Val Pro Trp Phe
65                  70                  75                  80
```

-continued

```
Asp Gln Gln Asn Gly Arg Thr Tyr Leu Lys Tyr Ser Ile Lys Ala Leu
                85                  90                  95

Val Gln Asn Asp Thr Leu Leu Gln Val Lys Gly Thr Gly Ala Asn Gly
            100                 105                 110

Ser Phe Lys Leu Asn Arg Lys Lys Leu Glu Gly Gly Glu Arg Arg
        115                 120                 125

Gly Ala Pro Ala Ala Thr Ala Pro Ala Pro Thr Ala His Lys Ala
    130                 135                 140

Lys Lys Ala Ala Pro Gly Ala Ala Gly Ser Arg Ala Asp Lys Lys
145                 150                 155                 160

Pro Ala Arg Gly Gln Lys Pro Glu Gln Arg Ser His Lys Lys Gly Ala
                165                 170                 175

Gly Ala Lys Lys Asp Lys Gly Gly Lys Ala Lys Lys Thr Ala Ala Ala
            180                 185                 190

Gly Gly Lys Lys Val Lys Lys Ala Ala Lys Pro Ser Val Pro Lys Val
        195                 200                 205

Pro Lys Gly Arg Lys
    210
```

<210> SEQ ID NO 5
<211> LENGTH: 642
<212> TYPE: DNA
<213> ORGANISM: Homo sapiens
<220> FEATURE:
<223> OTHER INFORMATION: histone H1.2

<400> SEQUENCE: 5

```
atgtccgaga ctgctcctgc cgctcccgct gccgcgcctc ctgcggagaa ggcccctgta      60
aagaagaagg cggccaaaaa ggctgggggt acgcctcgta aggcgtctgg tccccggtg     120
tcagagctca tcaccaaggc tgtggccgcc tctaaagagc gtagcggagt ttctctggct    180
gctctgaaaa aagcgttggc tgccgccggc tatgatgtgg agaaaaacaa cagccgtatc    240
aaacttggtc tcaagagcct ggtgagcaag ggcactctgg tgcaaacgaa aggcaccggt    300
gcttctggct cctttaaact caacaagaag gcagcctccg gggaagccaa gcccaaggtt    360
aaaaaggcgg gcggaaccaa acctaagaag ccagttgggg cagccaagaa gcccaagaag    420
gcggctggcg gcgcaactcc gaagaagagc gctaagaaaa caccgaagaa agcgaagaag    480
ccggccgcgg ccactgtaac caagaaagtg gctaagagcc caagaaggc caaggttgcg    540
aagcccaaga agctgccaa aagtgctgct aaggctgtga gcccaaggc cgctaagccc      600
aaggttgtca agcctaagaa ggcggcgccc aagaagaaat ag                       642
```

<210> SEQ ID NO 6
<211> LENGTH: 213
<212> TYPE: PRT
<213> ORGANISM: Homo sapiens
<220> FEATURE:
<223> OTHER INFORMATION: histone H1.2

<400> SEQUENCE: 6

```
Met Ser Glu Thr Ala Pro Ala Ala Pro Ala Ala Ala Pro Pro Ala Glu
1               5                   10                  15

Lys Ala Pro Val Lys Lys Lys Ala Ala Lys Lys Ala Gly Gly Thr Pro
            20                  25                  30

Arg Lys Ala Ser Gly Pro Pro Val Ser Glu Leu Ile Thr Lys Ala Val
        35                  40                  45

Ala Ala Ser Lys Glu Arg Ser Gly Val Ser Leu Ala Ala Leu Lys Lys
```

```
                50                  55                  60
Ala Leu Ala Ala Ala Gly Tyr Asp Val Glu Lys Asn Asn Ser Arg Ile
 65                  70                  75                  80

Lys Leu Gly Leu Lys Ser Leu Val Ser Lys Gly Thr Leu Val Gln Thr
                 85                  90                  95

Lys Gly Thr Gly Ala Ser Gly Ser Phe Lys Leu Asn Lys Lys Ala Ala
            100                 105                 110

Ser Gly Glu Ala Lys Pro Lys Val Lys Lys Ala Gly Gly Thr Lys Pro
        115                 120                 125

Lys Lys Pro Val Gly Ala Ala Lys Lys Pro Lys Lys Ala Ala Gly Gly
    130                 135                 140

Ala Thr Pro Lys Lys Ser Ala Lys Lys Thr Pro Lys Lys Ala Lys Lys
145                 150                 155                 160

Pro Ala Ala Ala Thr Val Thr Lys Lys Val Ala Lys Ser Pro Lys Lys
                165                 170                 175

Ala Lys Val Ala Lys Pro Lys Lys Ala Ala Lys Ser Ala Ala Lys Ala
            180                 185                 190

Val Lys Pro Lys Ala Ala Lys Pro Lys Val Val Lys Pro Lys Lys Ala
        195                 200                 205

Ala Pro Lys Lys Lys
    210
```

<210> SEQ ID NO 7
<211> LENGTH: 666
<212> TYPE: DNA
<213> ORGANISM: Homo sapiens
<220> FEATURE:
<223> OTHER INFORMATION: histone H1.3

<400> SEQUENCE: 7

```
atgtcggaga ctgctccact tgctcctacc attcctgcac ccgcagaaaa aacacctgtg      60
aagaaaaagg cgaagaaggc aggcgcaact gctgggaaac gcaaagcatc cggaccccca     120
gtatctgagc ttatcaccaa ggcagtggca gcttctaagg agcgcagcgg cgtttctctg     180
gccgcgctta agaaagcgct tgcggctgct ggctacgatg tagaaaaaaa caacagccgt     240
atcaagcttg gcctcaagag cttggtgagc aaaggtactc tggtgcagac caaaggtacc     300
ggtgcttctg gctccttcaa actcaacaag aaagcggctt ccggggaagg caaacccaag     360
gccaaaaagg ctggcgcagc caagcctagg aagcctgctg ggcagccaa gaagcccaag     420
aaggtggctg cgccgctac cccgaagaaa agcatcaaaa agactcctaa gaaggtaaag     480
aagccagcaa ccgctgctgg gaccaagaaa gtggccaaga gtgcgaaaaa ggtgaaaaca     540
cctcagccaa aaaagctgc caagagtcca gctaaggcca agcccctaa gcccaaggcg     600
gccaagccta agtcggggaa gccgaaggtt acaaaggcaa agaaggcagc tccgaagaaa     660
aagtga                                                                666
```

<210> SEQ ID NO 8
<211> LENGTH: 221
<212> TYPE: PRT
<213> ORGANISM: Homo sapiens
<220> FEATURE:
<223> OTHER INFORMATION: histone H1.3

<400> SEQUENCE: 8

```
Met Ser Glu Thr Ala Pro Leu Ala Pro Thr Ile Pro Ala Pro Ala Glu
 1               5                  10                  15
```

```
Lys Thr Pro Val Lys Lys Ala Lys Ala Gly Ala Thr Ala Gly
            20                  25                  30

Lys Arg Lys Ala Ser Gly Pro Pro Val Ser Glu Leu Ile Thr Lys Ala
        35                  40                  45

Val Ala Ala Ser Lys Glu Arg Ser Gly Val Ser Leu Ala Ala Leu Lys
    50                  55                  60

Lys Ala Leu Ala Ala Ala Gly Tyr Asp Val Glu Lys Asn Asn Ser Arg
65                  70                  75                  80

Ile Lys Leu Gly Leu Lys Ser Leu Val Ser Lys Gly Thr Leu Val Gln
                85                  90                  95

Thr Lys Gly Thr Gly Ala Ser Gly Ser Phe Lys Leu Asn Lys Lys Ala
            100                 105                 110

Ala Ser Gly Glu Gly Lys Pro Lys Ala Lys Lys Ala Gly Ala Ala Lys
        115                 120                 125

Pro Arg Lys Pro Ala Gly Ala Ala Lys Lys Pro Lys Lys Val Ala Gly
    130                 135                 140

Ala Ala Thr Pro Lys Lys Ser Ile Lys Lys Thr Pro Lys Lys Val Lys
145                 150                 155                 160

Lys Pro Ala Thr Ala Ala Gly Thr Lys Lys Val Ala Lys Ser Ala Lys
                165                 170                 175

Lys Val Lys Thr Pro Gln Pro Lys Lys Ala Ala Lys Ser Pro Ala Lys
            180                 185                 190

Ala Lys Ala Pro Lys Pro Lys Ala Ala Lys Pro Lys Ser Gly Lys Pro
        195                 200                 205

Lys Val Thr Lys Ala Lys Lys Ala Ala Pro Lys Lys Lys
    210                 215                 220

<210> SEQ ID NO 9
<211> LENGTH: 387
<212> TYPE: DNA
<213> ORGANISM: Homo sapiens
<220> FEATURE:
<223> OTHER INFORMATION: histone H2A.Z

<400> SEQUENCE: 9
atggctggcg gtaaggctgg aaaggactcc ggaaaggcca agacaaaggc ggtttcccgc    60
tcgcagagag ccggcttgca gttcccagtg ggccgtattc atcgacacct aaaatctagg   120
acgaccagtc atggacgtgt gggcgcgact gccgctgtgt acagcgcagc catcctggag   180
tacctcaccg cagaggtact tgaactggca ggaaatgcat caaaagactt aaaggtaaag   240
cgtattaccc ctcgtcactt gcaacttgct attcgtggag atgaagaatt ggattctctc   300
atcaaggcta caattgctgg tggtggtgtc attccacaca tccacaaatc tctgattggg   360
aagaaaggac aacagaagac tgtctaa                                       387

<210> SEQ ID NO 10
<211> LENGTH: 128
<212> TYPE: PRT
<213> ORGANISM: Homo sapiens
<220> FEATURE:
<223> OTHER INFORMATION: histone H2A.Z

<400> SEQUENCE: 10

Met Ala Gly Gly Lys Ala Gly Lys Asp Ser Gly Lys Ala Lys Thr Lys
1               5                   10                  15

Ala Val Ser Arg Ser Gln Arg Ala Gly Leu Gln Phe Pro Val Gly Arg
            20                  25                  30
```

Ile His Arg His Leu Lys Ser Arg Thr Thr Ser His Gly Arg Val Gly
             35                  40                  45

Ala Thr Ala Ala Val Tyr Ser Ala Ala Ile Leu Glu Tyr Leu Thr Ala
 50                  55                  60

Glu Val Leu Glu Leu Ala Gly Asn Ala Ser Lys Asp Leu Lys Val Lys
65                  70                  75                  80

Arg Ile Thr Pro Arg His Leu Gln Leu Ala Ile Arg Gly Asp Glu Glu
                 85                  90                  95

Leu Asp Ser Leu Ile Lys Ala Thr Ile Ala Gly Gly Val Ile Pro
             100                 105                 110

His Ile His Lys Ser Leu Ile Gly Lys Lys Gly Gln Gln Lys Thr Val
             115                 120                 125

<210> SEQ ID NO 11
<211> LENGTH: 381
<212> TYPE: DNA
<213> ORGANISM: Homo sapiens
<220> FEATURE:
<223> OTHER INFORMATION: histone H2B

<400> SEQUENCE: 11
atgccggatc cagcgaaatc cgctcctgct cccaagaagg gctccaaaaa ggctgttacg      60
aaagtgcaga agaaggacgg caagaagcgc aagcgcagcc gcaaggagag ctactccgtt     120
tacgtgtaca aggtgctgaa gcaggtccac cccgacaccg gcatctcgtc caaggccatg     180
ggcatcatga actccttcgt caacgacatc ttcgagcgca tcgcgggaga ggcgtcccgc     240
ctggcgcact acaacaagcg ctccaccatc acatcccgcg agatccagac ggccgtgcgc     300
ctgctgctgc ccggcgagct ggccaagcac gccgtgtccg agggcaccaa gcggtcacc      360 aagtacacca gctcgaagta a                                              381

<210> SEQ ID NO 12
<211> LENGTH: 126
<212> TYPE: PRT
<213> ORGANISM: Homo sapiens
<220> FEATURE:
<223> OTHER INFORMATION: histone H2B

<400> SEQUENCE: 12

Met Pro Asp Pro Ala Lys Ser Ala Pro Ala Pro Lys Lys Gly Ser Lys
 1               5                  10                  15

Lys Ala Val Thr Lys Val Gln Lys Lys Asp Gly Lys Lys Arg Lys Arg
             20                  25                  30

Ser Arg Lys Glu Ser Tyr Ser Val Tyr Val Tyr Lys Val Leu Lys Gln
         35                  40                  45

Val His Pro Asp Thr Gly Ile Ser Ser Lys Ala Met Gly Ile Met Asn
 50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                 85                  90                  95

Thr Ala Val Arg Leu Leu Leu Pro Gly Glu Leu Ala Lys His Ala Val
             100                 105                 110

Ser Glu Gly Thr Lys Ala Val Thr Lys Tyr Thr Ser Ser Lys
             115                 120                 125

<210> SEQ ID NO 13
<211> LENGTH: 312

```
<212> TYPE: DNA
<213> ORGANISM: Homo sapiens
<220> FEATURE:
<223> OTHER INFORMATION: histone H4

<400> SEQUENCE: 13
atgtccggca gaggaaaggg cggaaaaggc ttaggcaaag ggggcgctaa gcgccaccgc      60
aaggtcttga gagacaacat tcagggcatc accaagcctg ccattcggcg tctagctcgg     120
cgtggcggcg ttaagcggat ctctggcctc atttacgagg agacccgcgg tgtgctgaag     180
gtgttcctgg agaatgtgat tcgggacgca gtcacctaca ccgagcacgc caagcgcaag     240
accgtcacag ccatggatgt ggtgtacgcg ctcaagcgcc aggggcgcac cctgtacggc     300
ttcggaggct ag                                                         312

<210> SEQ ID NO 14
<211> LENGTH: 103
<212> TYPE: PRT
<213> ORGANISM: Homo sapiens
<220> FEATURE:
<223> OTHER INFORMATION: histone H4

<400> SEQUENCE: 14
```

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

```
<210> SEQ ID NO 15
<211> LENGTH: 21
<212> TYPE: DNA
<213> ORGANISM: Artificial Sequence
<220> FEATURE:
<223> OTHER INFORMATION: laboratory-synthesized DNA primer

<400> SEQUENCE: 15
tcaatgtgga gctgaggaaa g                                                21

<210> SEQ ID NO 16
<211> LENGTH: 22
<212> TYPE: DNA
<213> ORGANISM: Artificial Sequence
<220> FEATURE:
<223> OTHER INFORMATION: laboratory-synthesized DNA primer

<400> SEQUENCE: 16
caacagacca atttacagtg cc                                               22

<210> SEQ ID NO 17
<211> LENGTH: 20
<212> TYPE: DNA
<213> ORGANISM: Artificial Sequence
```

```
<220> FEATURE:
<223> OTHER INFORMATION: laboratory-synthesized DNA primer

<400> SEQUENCE: 17
ccctctgcca gttctatgtg                                               20

<210> SEQ ID NO 18
<211> LENGTH: 20
<212> TYPE: DNA
<213> ORGANISM: Artificial Sequence
<220> FEATURE:
<223> OTHER INFORMATION: laboratory-synthesized DNA primer

<400> SEQUENCE: 18
gtagctggcg atgttgaaag                                               20

<210> SEQ ID NO 19
<211> LENGTH: 17
<212> TYPE: DNA
<213> ORGANISM: Artificial Sequence
<220> FEATURE:
<223> OTHER INFORMATION: laboratory-synthesized DNA primer

<400> SEQUENCE: 19
ctgggcctgg actcttc                                                  17

<210> SEQ ID NO 20
<211> LENGTH: 21
<212> TYPE: DNA
<213> ORGANISM: Artificial Sequence
<220> FEATURE:
<223> OTHER INFORMATION: laboratory-synthesized DNA primer

<400> SEQUENCE: 20
cacatcccca aagttaagca c                                             21

<210> SEQ ID NO 21
<211> LENGTH: 19
<212> TYPE: DNA
<213> ORGANISM: Artificial Sequence
<220> FEATURE:
<223> OTHER INFORMATION: laboratory-synthesized DNA primer

<400> SEQUENCE: 21
ttctgtcaga tgggcaagc                                                19

<210> SEQ ID NO 22
<211> LENGTH: 22
<212> TYPE: DNA
<213> ORGANISM: Artificial Sequence
<220> FEATURE:
<223> OTHER INFORMATION: laboratory-synthesized DNA primer

<400> SEQUENCE: 22
ccaaccattc tctataggct cc                                            22

<210> SEQ ID NO 23
<211> LENGTH: 21
<212> TYPE: DNA
<213> ORGANISM: Artificial Sequence
<220> FEATURE:
<223> OTHER INFORMATION: laboratory-synthesized DNA primer

<400> SEQUENCE: 23
ttgaaaccac taagccagga g                                             21
```

```
<210> SEQ ID NO 24
<211> LENGTH: 21
<212> TYPE: DNA
<213> ORGANISM: Artificial Sequence
<220> FEATURE:
<223> OTHER INFORMATION: laboratory-synthesized DNA primer

<400> SEQUENCE: 24
tgttggaata tagggtgctg g                                              21

<210> SEQ ID NO 25
<211> LENGTH: 22
<212> TYPE: DNA
<213> ORGANISM: Artificial Sequence
<220> FEATURE:
<223> OTHER INFORMATION: laboratory-synthesized DNA primer

<400> SEQUENCE: 25
cgtggatggt gtggtctatt ac                                             22

<210> SEQ ID NO 26
<211> LENGTH: 22
<212> TYPE: DNA
<213> ORGANISM: Artificial Sequence
<220> FEATURE:
<223> OTHER INFORMATION: laboratory-synthesized DNA primer

<400> SEQUENCE: 26
cccagaacat tcctcagagt ag                                             22

<210> SEQ ID NO 27
<211> LENGTH: 18
<212> TYPE: DNA
<213> ORGANISM: Artificial Sequence
<220> FEATURE:
<223> OTHER INFORMATION: laboratory-synthesized DNA primer

<400> SEQUENCE: 27
gacagcctcc cacatgac                                                  18

<210> SEQ ID NO 28
<211> LENGTH: 19
<212> TYPE: DNA
<213> ORGANISM: Artificial Sequence
<220> FEATURE:
<223> OTHER INFORMATION: laboratory-synthesized DNA primer

<400> SEQUENCE: 28
gtagtcgcca taccccatg                                                 19

<210> SEQ ID NO 29
<211> LENGTH: 20
<212> TYPE: DNA
<213> ORGANISM: Artificial Sequence
<220> FEATURE:
<223> OTHER INFORMATION: laboratory-synthesized DNA primer

<400> SEQUENCE: 29
ggtaaggctg gaaaggactc                                                20

<210> SEQ ID NO 30
<211> LENGTH: 21
<212> TYPE: DNA
<213> ORGANISM: Artificial Sequence
<220> FEATURE:
<223> OTHER INFORMATION: laboratory-synthesized DNA primer
```

```
<400> SEQUENCE: 30
ttaggtgtcg atgaatacgg c                                          21

<210> SEQ ID NO 31
<211> LENGTH: 21
<212> TYPE: DNA
<213> ORGANISM: Artificial Sequence
<220> FEATURE:
<223> OTHER INFORMATION: laboratory-synthesized DNA primer

<400> SEQUENCE: 31
gaaaaggaca gatgaagctg c                                          21

<210> SEQ ID NO 32
<211> LENGTH: 22
<212> TYPE: DNA
<213> ORGANISM: Artificial Sequence
<220> FEATURE:
<223> OTHER INFORMATION: laboratory-synthesized DNA primer

<400> SEQUENCE: 32
gacacagtac tcttggaagt cc                                         22

<210> SEQ ID NO 33
<211> LENGTH: 24
<212> TYPE: DNA
<213> ORGANISM: Artificial Sequence
<220> FEATURE:
<223> OTHER INFORMATION: laboratory-synthesized DNA primer

<400> SEQUENCE: 33
ttgtgctaga gataaggaag ttgg                                       24

<210> SEQ ID NO 34
<211> LENGTH: 22
<212> TYPE: DNA
<213> ORGANISM: Artificial Sequence
<220> FEATURE:
<223> OTHER INFORMATION: laboratory-synthesized DNA primer

<400> SEQUENCE: 34
tgtgttgata agctctacgg tg                                         22

<210> SEQ ID NO 35
<211> LENGTH: 19
<212> TYPE: DNA
<213> ORGANISM: Artificial Sequence
<220> FEATURE:
<223> OTHER INFORMATION: laboratory-synthesized DNA primer

<400> SEQUENCE: 35
aagtactcga tcaaggcgc                                             19

<210> SEQ ID NO 36
<211> LENGTH: 20
<212> TYPE: DNA
<213> ORGANISM: Artificial Sequence
<220> FEATURE:
<223> OTHER INFORMATION: laboratory-synthesized DNA primer

<400> SEQUENCE: 36
tgagcttgaa ggaaccgttg                                            20

<210> SEQ ID NO 37
```

```
<211> LENGTH: 21
<212> TYPE: DNA
<213> ORGANISM: Artificial Sequence
<220> FEATURE:
<223> OTHER INFORMATION: laboratory-synthesized DNA primer

<400> SEQUENCE: 37
aacagggaga caaaggtgaa g                                              21

<210> SEQ ID NO 38
<211> LENGTH: 20
<212> TYPE: DNA
<213> ORGANISM: Artificial Sequence
<220> FEATURE:
<223> OTHER INFORMATION: laboratory-synthesized DNA primer

<400> SEQUENCE: 38
gaggaacaag gtcaaaagcc                                                20

<210> SEQ ID NO 39
<211> LENGTH: 20
<212> TYPE: DNA
<213> ORGANISM: Artificial Sequence
<220> FEATURE:
<223> OTHER INFORMATION: laboratory-synthesized DNA primer

<400> SEQUENCE: 39
gcgctaagaa aacaccgaag                                                20

<210> SEQ ID NO 40
<211> LENGTH: 20
<212> TYPE: DNA
<213> ORGANISM: Artificial Sequence
<220> FEATURE:
<223> OTHER INFORMATION: laboratory-synthesized DNA primer

<400> SEQUENCE: 40
cttttggcag ctttcttggg                                                20

<210> SEQ ID NO 41
<211> LENGTH: 24
<212> TYPE: DNA
<213> ORGANISM: Artificial Sequence
<220> FEATURE:
<223> OTHER INFORMATION: laboratory-synthesized DNA primer

<400> SEQUENCE: 41
aaagtgcaga agaaggacgg caag                                           24

<210> SEQ ID NO 42
<211> LENGTH: 24
<212> TYPE: DNA
<213> ORGANISM: Artificial Sequence
<220> FEATURE:
<223> OTHER INFORMATION: laboratory-synthesized DNA primer

<400> SEQUENCE: 42
tgacgaagga gttcatgatg ccca                                           24

<210> SEQ ID NO 43
<211> LENGTH: 20
<212> TYPE: DNA
<213> ORGANISM: Artificial Sequence
<220> FEATURE:
<223> OTHER INFORMATION: laboratory-synthesized DNA primer

<400> SEQUENCE: 43
```

```
ctgccaagag tccagctaag                                                   20

<210> SEQ ID NO 44
<211> LENGTH: 21
<212> TYPE: DNA
<213> ORGANISM: Artificial Sequence
<220> FEATURE:
<223> OTHER INFORMATION: laboratory-synthesized DNA primer

<400> SEQUENCE: 44
ctttgccttt gtaaccttcg g                                                 21

<210> SEQ ID NO 45
<211> LENGTH: 20
<212> TYPE: DNA
<213> ORGANISM: Artificial Sequence
<220> FEATURE:
<223> OTHER INFORMATION: laboratory-synthesized DNA primer

<400> SEQUENCE: 45
tggtgttctg aaggtgttcc                                                   20

<210> SEQ ID NO 46
<211> LENGTH: 20
<212> TYPE: DNA
<213> ORGANISM: Artificial Sequence
<220> FEATURE:
<223> OTHER INFORMATION: laboratory-synthesized DNA primer

<400> SEQUENCE: 46
gtaaagagtg cgtccctgtc                                                   20

<210> SEQ ID NO 47
<211> LENGTH: 19
<212> TYPE: DNA
<213> ORGANISM: Artificial Sequence
<220> FEATURE:
<223> OTHER INFORMATION: laboratory-synthesized DNA primer

<400> SEQUENCE: 47
ttgcaaaatg tcgcagctg                                                    19

<210> SEQ ID NO 48
<211> LENGTH: 21
<212> TYPE: DNA
<213> ORGANISM: Artificial Sequence
<220> FEATURE:
<223> OTHER INFORMATION: laboratory-synthesized DNA primer

<400> SEQUENCE: 48
ccccagcttc acagagtatt g                                                 21

<210> SEQ ID NO 49
<211> LENGTH: 21
<212> TYPE: DNA
<213> ORGANISM: Artificial Sequence
<220> FEATURE:
<223> OTHER INFORMATION: laboratory-synthesized DNA primer

<400> SEQUENCE: 49
tgagcgaatc ccaaccataa g                                                 21

<210> SEQ ID NO 50
<211> LENGTH: 24
<212> TYPE: DNA
```

```
<213> ORGANISM: Artificial Sequence
<220> FEATURE:
<223> OTHER INFORMATION: laboratory-synthesized DNA primer

<400> SEQUENCE: 50
aaatcctgtc cacagtgaag gcca                                       24

<210> SEQ ID NO 51
<211> LENGTH: 22
<212> TYPE: DNA
<213> ORGANISM: Artificial Sequence
<220> FEATURE:
<223> OTHER INFORMATION: laboratory-synthesized DNA primer

<400> SEQUENCE: 51
agaaattgct agagaccgag tg                                         22

<210> SEQ ID NO 52
<211> LENGTH: 20
<212> TYPE: DNA
<213> ORGANISM: Artificial Sequence
<220> FEATURE:
<223> OTHER INFORMATION: laboratory-synthesized DNA primer

<400> SEQUENCE: 52
acgcccatct ttatcaccag                                            20

<210> SEQ ID NO 53
<211> LENGTH: 21
<212> TYPE: DNA
<213> ORGANISM: Artificial Sequence
<220> FEATURE:
<223> OTHER INFORMATION: laboratory-synthesized DNA primer

<400> SEQUENCE: 53
gcgagcttaa ttgcgtaatc c                                          21

<210> SEQ ID NO 54
<211> LENGTH: 21
<212> TYPE: DNA
<213> ORGANISM: Artificial Sequence
<220> FEATURE:
<223> OTHER INFORMATION: laboratory-synthesized DNA primer

<400> SEQUENCE: 54
ctgaagatgc ctgtggaaaa c                                          21
```